(12) United States Patent
Reubinoff

(10) Patent No.: US 8,133,730 B2
(45) Date of Patent: Mar. 13, 2012

(54) GENERATION OF NEURAL STEM CELLS FROM UNDIFFERENTIATED HUMAN EMBRYONIC STEM CELLS

(75) Inventor: Benjamin Eithan Reubinoff, Jerusalem (IL)

(73) Assignee: ES Cell International PTE Ltd, Singapore (SG)

( * ) Notice: Subject to any disclaimer, the term of this patent is extended or adjusted under 35 U.S.C. 154(b) by 0 days.

(21) Appl. No.: 12/134,521

(22) Filed: Jun. 6, 2008

(65) Prior Publication Data

US 2009/0004736 A1 Jan. 1, 2009

Related U.S. Application Data

(60) Division of application No. 11/005,518, filed on Dec. 3, 2004, now Pat. No. 7,604,992, which is a continuation of application No. PCT/AU03/00704, filed on Jun. 5, 2003.

(30) Foreign Application Priority Data

| Jun. 5, 2002 | (AU) | ................................. PS2793 |
| Oct. 4, 2002 | (AU) | ................................. 2002951874 |
| Mar. 28, 2003 | (AU) | ................................. 2003901536 |
| Mar. 28, 2003 | (AU) | ................................. 2003901537 |
| May 15, 2003 | (AU) | ................................. 2003902348 |

(51) Int. Cl.
*C12N 5/079* (2010.01)
*C12N 5/22* (2006.01)
*C12N 5/095* (2010.01)

(52) U.S. Cl. .................... 435/377; 435/366; 435/368

(58) Field of Classification Search .................... None
See application file for complete search history.

(56) References Cited

U.S. PATENT DOCUMENTS

| 6,277,820 B1 | 8/2001 | Rosenthal et al. |
| 6,284,539 B1 | 9/2001 | Bowen et al. |
| 6,844,312 B2 | 1/2005 | Weiss et al. |
| 7,294,510 B2 | 11/2007 | Okano et al. |
| 2002/0022267 A1 | 2/2002 | Pera et al. |
| 2002/0039724 A1 | 4/2002 | Carpenter |
| 2002/0151053 A1 | 10/2002 | Carpenter et al. |
| 2002/0164791 A1* | 11/2002 | Van Der Kooy et al. ..... 435/366 |
| 2002/0192817 A1 | 12/2002 | Weiss et al. |
| 2003/0036195 A1 | 2/2003 | Studer et al. |
| 2003/0103949 A1 | 6/2003 | Carpenter et al. |
| 2004/0247571 A1 | 12/2004 | Meijer et al. |
| 2005/0255589 A1 | 11/2005 | Reubinoff |

FOREIGN PATENT DOCUMENTS

| GB | 2 407 821 A | 5/2005 |
| GB | 2407821 | 5/2005 |
| GB | 2 427 616 A | 1/2007 |
| GB | 2427616 | 1/2007 |
| WO | 0027995 | 5/2000 |
| WO | WO 00/27995 | 5/2000 |
| WO | WO 00/66713 | 11/2000 |
| WO | 0168815 | 8/2001 |
| WO | WO 01/68815 | 8/2001 |
| WO | 0183715 | 11/2001 |
| WO | 0188104 | 11/2001 |
| WO | WO 01/82946 | 11/2001 |
| WO | WO 01/83715 | 11/2001 |
| WO | WO 01/88104 | 11/2001 |
| WO | 0198463 | 12/2001 |
| WO | WO 01/98463 | 12/2001 |
| WO | 0226941 | 4/2002 |
| WO | WO 02/26941 | 4/2002 |
| WO | 02081663 | 10/2002 |
| WO | WO 02/081663 | 10/2002 |
| WO | WO 02/083877 | 10/2002 |
| WO | WO 02/086106 | 10/2002 |
| WO | 03000868 | 1/2003 |
| WO | WO 03/000868 | 1/2003 |
| WO | WO 03/104444 | 12/2003 |

OTHER PUBLICATIONS

Gage et al, Proceedings of the National Academy of Sciences, USA. 1995, vol. 92, pp. 11879-11883.*
Wang et al. Biochemicla and Biophysical Research Communication, 2005, vol. 330, pp. 937-942.*
Itsykson et al. Molecular Cell Neuroscience, 2005, vol. 30, pp. 24-36.*
Ben-Hur T. et al., "Transplantation of Human Embryonic Stem Cell-Derived Neural Progenitors Improves Behavioral Deficit in Parkinsonian Rats", Stem Cells, 22(7):1246-1255 (2004), XP-009054362.
Reubinoff B.E. et al., "Neural Progenitors from Human Embryonic Stem Cells", Nature Biotechnology, 19 (12):1134-1140 (2001), XP-002971362.
Lee S.H. et al., "Efficient Generation of Midbrain and Hindbrain Neurons from Mouse Embryonic Stem Cells", Nature Biotechnology, 18:675-679 (2000), XP-000941668.
Ye W. et al., "FGF and Shh Signals Control Dopaminergic and Serotonergic Cell Fate in the Anterior Neural Plate", Cell, 93:755-766 (1998).
Tanaka A. et al., "Extensive Neuronal Localization and Neurotrophic Function of Fibroblast Growth Factor 8 in the Nervous System", Brain Research, 912(2):105-115 (2001).
Lee S.M.K et al. "Evidence that FGF8 Signalling from the Midbrain-Hindbrain Junction Regulates Growth and Polarity in the Developing Midbrain", Development, 124(5):959-969 (1997).

(Continued)

*Primary Examiner* — Bridget E Bunner
*Assistant Examiner* — Fozia M Hamud

(57) ABSTRACT

The present invention relates to the generation of neural cells from undifferentiated human embryonic stem cells. In particular it relates to directing the differentiation of human ES cells into neural progenitors and neural cells and the production of functioning neural cells and/or neural cells of a specific type. The invention also includes the use of these cells for the treatment of neurological conditions such as Parkinson's disease.

9 Claims, 34 Drawing Sheets

(14 of 34 Drawing Sheet(s) Filed in Color)

OTHER PUBLICATIONS

Bartlett P.F., "Regulation and Potential of Neural Stem Cells", Cell Biology International, 24(12):924 (2000).
Bartlett P.F. et al., "Regulation of Neural Stem Cell Differentiation in the Forebrain", Immunology & Cell Biology, 76 (5):414-418 (1998).
Lacovitti L. et al., "The Differentiation of Dopamine Neurons from Stem/Precursor Cells in Culture and In Vivo", Society for Neuroscience Abstracts 26, Abstract No. 312-21 & Biosis Abstract PREV200100088079 (2000).
Ford-Perriss M. et al., "Fibroblast Growth Factors in the Developing Central Nervous System", Clinical and Experimental Pharmacology and Physiology, 28(7):493-503 (2001).
Reubinoff, B. E., et al., "Embryonic stem cell lines from human blastocysts: somatic differentiation in vitro", Nature Biotechnology 18(4):399-404, (2000).
Lillien L., et al., "BMP and FGF regulate the development of EGF-responsive neural progenitor cells", Development 127:4993-5005, (2000).
Schuldiner M., et al. "Effects of eight growth factors on the differentiation of cells derived from human embryonic stem cells", Proc. Natl. Acad. Sci USA 97(21):11307-11312, (2000).
Wagner, et al., Nature Biotechnology, 17:653-659, (1999).
Rolletchek, et al., Mech. Development, 105:93-104, (2001).
Sonntag, et al., European Journal of Neuroscience, 19:1141-1152, (2004).
Smidt, et al., Nature Neuroscience, 3(4):337-341, (2000).
Ju, et al., Proc Nat'l Acad Sci USA, 88(7):2658-2662, (1991).
Kruse, et al. EMBO J., 11(9):3237-3244, (1992).
Communication Pursuant to Article 94(3) EPC Dated Oct. 22, 2008 From the European Patent Office Re.: Application No. 03724662.6.
Pera et al. "Human Embryonic Stem Cells", *Journal of Cell Science*, XP002209790, 113: 5-10 (2000).
Examiner's Report Dated Feb. 19, 2009 From the Australian Government, IP Australia Re.: Application No. 2003229132.
Invitation to Pay Additional Fees Dated Jun. 25, 2003 From the International Searching Authority Re.: Application No. PCT/AU03/00704.
Notice of Allowance Dated Mar. 23, 2009 From the US Patent and Trademark Office Re.: U.S. Appl. No. 11/005,518.
Official Action Dated Jul. 2, 2008 From the US Patent and Trademark Office Re.: U.S. Appl. No. 11/005,518.
Official Action Dated Jun. 27, 2007 From the US Patent and Trademark Office Re.: U.S. Appl. No. 11/005,518.
Official Action Dated Nov. 29, 2006 From the US Patent and Trademark Office Re.: U.S. Appl. No. 11/005,518.
Response Dated Jan. 28, 2008 to Official Action of Sep. 27, 2007 From the US Patent and Trademark Office Re.: U.S. Appl. No. 11/005,518.
Response Dated Mar. 28, 2007 to Official Action of Nov. 29, 2006 From the US Patent and Trademark Office Re.: U.S. Appl. No. 11/005,518.
Response Dated Dec. 31, 2008 to Official Action of Jul. 2, 2008 From the US Patent and Trademark Office Re.: U.S. Appl. No. 11/005,518.
Communication Pursuant to Article 94(3) EPC Dated Oct. 29, 2009 From the European Patent Office Re.: Applicaiton No. 03724662.6.
Communication Pursuant to Article 96(2) EPC Dated Aug. 20, 2007 From the European Patent Office Re.: Application No. 03724662.6.
Response Dated Feb. 22, 2010 to Communication Pursuant to Article 94(3) EPC of Oct. 29, 2009 From the European Patent Office Re.: Application No. 03724662.6.
Robertson "NIH Sacrifies Commercial Rights in WiCell Deal", Nature Biotechnology, 19: 1001, Nov. 2001.
Response Dated Mar. 31, 2011 to Summons to Attend Oral Proceedings Pursuant to Rule 115(1) EPC of Jan. 20, 2011 From the European Patent Office Re. Application No. 03724662.6.
Summons to Attend Oral Proceedings Pursuant to Rule 115(1) EPC Dated Jan. 20, 2011 From the European Patent Office Re. Application No. 03724662.6.
European Search Report and the European Search Opinion Dated Jan. 31, 2011 From the European Patent Office Re. Application No. 10010476.9.

Mehler et al. "Developmental Changes in Progenitor Cell Responsiveness to Bone Morphogenetic Proteins Differentially Modulate Progressive CNS Lineage Fate", Developmental Neuroscience, XP009074411, 22(1/02): 74-85, 2000. Abstract, Figs.1, 2, 4.
Tropepe et al. "Direct Neural Fate Specification From Embryonic Stem Cells: A Primitive Mammalian Neural Stem Cell Stage Acquired Through a Default Mechanism", Neuron, XP002202327, 30(1): 65-78, Apr. 1, 2001. p. 69, col. 2, § 2.
Zhang et al. "In Vitro Differentiation of Transplantable Neural Precursors From Human Embryonic Stem Cells", Nature Biotechnology, XP002971361, 19(12): 1129-1133, Dec. 1, 2001. Abstract, Figs. 1, 4.
Requisition by the Examiner Dated Dec. 29, 2010 From the Canadian Intellectual Property Office Re. Application No. 2,488,429.
Response Dated Sep. 5, 2011 to Examiner's Report of Jul. 28, 2011 From the Australian Government, IP Australia Re.: Application No. 2009213101.
Combined Search and Examination Report Under Sections 17 & 18(3) Dated Oct. 26, 2006 From the Patent Office of the United Kingdom Re.: Application No. GB0617406.4.
Communication Pursuant to Article 96(2) EPC Dated Feb. 3, 2006 From the European Patent Office Re.: Application No. 03724662.6.
European Search Report and the European Search Opinion Dated Jun. 9, 2011 From the European Patent Office Re. Application No. 10011875.1.
Examination Report Under Section 18(3) Dated Feb. 2, 2007 From the Patent Office of the United Kingdom Re.: Application No. GB0428149.9.
Examination Report Under Section 18(3) Dated Dec. 23, 2005 From the Patent Office of the United Kingdom Re.: Application No. GB0428149.9.
Further Search Report Under Section 17 Dated Sep. 6, 2006 From the Patent Office of the United Kingdom Re.: Application No. GB0428149.9.
International Preliminary Examination Report Dated Sep. 30, 2004 From the International Preliminary Examining Authority Re.: Application No. PCT/AU2003/000704.
International Search Report Dated Aug. 6, 2003 From the International Searching Authority Re.: Application No. PCT/AU03/00704.
Official Action Dated Mar. 9, 2006 From the US Patent and Trademark Office Re.: U.S. Appl. No. 11/005,518.
Official Action Dated Sep. 27, 2007 From the US Patent and Trademark Office Re.: U.S. Appl. No. 11/005,518.
Search and Examination Report Under Sections 17 & 18(3) Dated Sep. 7, 2006 From the Patent Office of the United Kingdom Re.: Application No. GB0428149.9.
Search Report Under Section 17 Dated Oct. 25, 2006 From the Patent Office of the United Kingdom Re.: Application No. GB0617406.4.
Supplementary European Search Report Dated Oct. 6, 2005 From the European Patent Office Re.: Application No. 03724662.6.
Written Opinion Dated Oct. 27, 2003 From the International Preliminary Examining Authority Re.: Application No. PCT/AU03/00704.
Bartlett "Regulation and Potential of Neural Stem Cells", Cell Biology International, 24(12): 924, 2000.
Bartlett et al. "Regulation of Neural Stem Cell Differentiation in the Forebrain", Immunology & Cell Biology, 76(5): 414-418, 1998. p. 417, r-h §.
Ben-Hur et al. "Transplantation of Human Embryonic Stem Cell-Derived Neural Progenitors Improves Behavioral Deficit in Parkinsonian Rats", Stem Cells, 22(7): 1246-1255, 2004.
Blits et al. "AAV-Mediated Overexpressed of GDNF and BDNF Rescues Mononeurons Following Avulsion and Reimplantation of Rat Lumbar Ventral Roots", Abstracts of the Annual Meeting of the Society for Neuroscience, XP002962774, 27(2): 2116, Nov. 1, 2001. Abstract.
Feng et al. "Differential Effects of GDNF and BDNF on Cultures Ventral Mesencephalic Neurons", Molecular Brain Research, XP009148973, 66(1-2): 62- 70, Mar. 20, 1999. p. 67, col.2, § 1, Figs. 2, 3.
Ford-Perriss et al. "Fibroblast Growth Factors in the Developing Central Nervous System", Clinical Analytical and Experimental Pharmacology and Physiology, 28(7): 493-503, 2001. Table 1, p. 496.

Iacovitti et al. "Differentiation of Human Dopamine Neurons From An Embryonic Carcinomal Stem Cell Line", Brain Research, 912: 99-104, 2001.

Iacovitti et al. "The Differentiation of Dopamine Neurons From Stem/Precursor Cells in Culture and In Vivo", Society for Neuroscience Abstracts 26, Abstract No. 312-21 & Biosis Abstract PREV200100088079, 2000.

Ju et al. "Conversion of the Interleukin 1 Receptor Antagonist Into An Agonist by Site-Specific Mutagenesis", Proc. Natl. Acad. Sci. USA, 88: 2658-2662, 1991.

Kruse et al. "Conversion of Human Interleukin-4 Into A High Affinity Antagonist by A Single Amino Acid Replacement", The EMBO Journal, 11(9): 3237-3244, 1992.

Lee et al. "Efficient Generation of Midbrain and Hindbrain Neurons From Mouse Embryonic Stem Cells", Nature Biotechnology, 18: 675-679, 2000.

Lee et al. "Evidence That FGF8 Signalling From the Midbrain-Hindbrain Junction Regulates Growth and Polarity in the Developing Midbrain", Development, 124(5): 959-969, 1997. pp. 966-967.

Lillien et al. "BMP and FGF Regulate the Development of EGF-Responsove Neural Progenitor Cells", Development, 127(22): 4993-5005, 2000.

Ramsden et al. "The Aetiology of Idiopathic Parkinson's Disease", Journal of Chinese Pathology: Molecular Pathology, XP002983397, 54(6): 369-380, Dec. 2001. p. 369, col.2, § 2, Table 1.

Reubinoff et al. "Embryonic Stem Cell Lines From Human Blastocysts: Somatic Differentiation In Vitro", Nature Biotechnology, 18: 399-404, 2000.

Reubinoff et al. "Neural Progenitors From Human Embryonic Stem Cells", Nature Biotechnology, XP002971362, 19(12): 1134-1140, Dec. 2001.

Rolletschek et al. "Differentiation of Embryonic Stem Cell-Derived Dopaminergic Neurons Is Enhanced by Survival-Promoting Factors", Mechanisms of Development, XP002955960, 105: 93-104, Jul. 1, 2001. p. 97, col. 2, § 1—p. 100.

Schuldiner et al. "Effects of Eight Growth Factors on the Differentiation of Cells Derived From Human Embryonic Stem Cells", Proc. Natl. Acad. Sci. USA, 97(21): 11307-11312, 2000.

Smidt et al. "A Second Independent Pathway for Development of Mesencephalic Dopaminergic Neurons Requires Lmx 1b", Nature Neuroscience, XP002430683, 3(4): 337-341, Apr. 2000.

Sonntag et al. "Temporally Induced Nurr1 Can Induce A Non-Neuronal Dopaminergic Cell Type in Embryonic Stem Cell Differentiation", European Journal of Neuroscience, 19: 1141-1152, 2004.

Tanaka et al. "Extensive Neuronal Localization and Neurotrophic Function of Fibroblast Growth Factor 8 in the Nervous System", Brain Research, 912(2): 105-115, 2001.

Vejsada et al. "Synergistic But Transient Rescue Effects of BDNF and GDNF on Axotomized Neonatal Motoneurons", Neuroscience, XP000984885, 84(1): 129-139, Feb. 3, 1998.

Wagner et al. "Induction of a Midbrain Dopaminergic Phenotype in Nurr1-Overexpressing Neural Stem Cell by Type 1 Astrocytes", Nature Biotechnology, XP002154887, 17(7): 653-659, Jul. 1999. Figs.1, 3, 5-7.

Ye et al. "FGF and Shh Signals Control Dopaminergic and Serotonergic Cell Fate in the Anterior Neural Plate", Cell, 93: 755-766, 1998.

Zurn et al. "Sustained Delivery of GDNF: Towards A Treatment for Parkinson's Disease", Brain Research Reviews, XP009148972, 36(2-3): 222-229, Oct. 2001. pp. 224-228.

Response Dated Jun. 22, 2011 to Requisition by the Examiner of Dec. 29, 2010 From the Canadian Intellectual Property Office Re. Application No. 2,488,429.

Examiner's Report Dated Jul. 28, 2011 From the Australian Government, IP Australia Re.: Application No. 2009213101.

* cited by examiner

% represents the number of stained cells with a specific antibody from the total of 200 cells, within 4 independent experiments.

* $p < 0.01$ vs. NPM+FGF2

A

B

C

D

E

1 FGF8 (200ng/ml) & SHH (1μg/ml) & ascorbic acid (AA) (800μM/ml)
2 FGF8 (200ng/ml) & AA (800μM/ml)
3 FGF17 (200ng/ml) & AA (800μM/ml)
4 FGF17 (100ng/ml) & AA (400μM/ml)
5 FGF8 (100ng/ml) & FGF17 (100ng/ml) & AA (400μM/ml)
6 AA (800μM/ml)
7 SHH (1μg/ml) & AA (800μM/ml)

1 FGF1 (200ng/ml), IBMX (0.25mM), forskolin (50μM), TPA (200nM), dopamine (20μM), ascorbic acid (AA) (400μM)
2 FGF1 (100ng/ml), IBMX (0.25mM), forskolin (50μM), TPA (200nM), dopamine (20μM), AA (400μM)
3 FGF8 (100ng/ml), IBMX (0.25mM), forskolin (50μM), TPA (200nM), dopamine (20μM), AA (400μM)
4 FGF8 (200ng/ml), IBMX (0.25mM), forskolin (50μM), TPA (200nM), dopamine (20μM), AA (400μM)
5 IBMX (0.25mM), forskolin (50μM), TPA (200nM), dopamine (20μM), AA (400μM)
6 Control DMSO, AA (400μM)

% Represents the percentage of TH positive cells from the total number of β-tubulinIII positive cells.

n=1

HNS: n=16
Control: n=12
*p<0.05 as compared to 2weeks and to the corresponding control group Transplanted, n=11; control, n=10
* p=0.00037 as compared to control animals at 12 weeks
p=0.0036 as compared to baseline rotations at 2 weeks stepping Transplanted, n=11, mean = 17+/-3.5;
Control, n=10, mean = 2.65+/-2
* P=0.0026 as compared to control placing Transplanted, n=11, mean = 31.3+/-5.6;
Control, n=10, mean=5.4+/-2.66
** P=0.0007 as compared to control

B

X100

A

X100

100X

X200

Fig. 31A   Fig. 31B   Fig. 31C
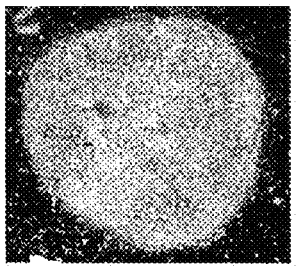 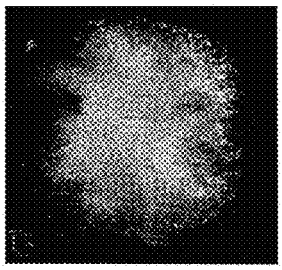 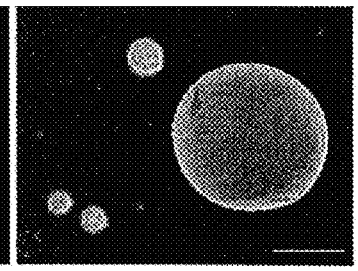
Fig. 31D   Fig. 31E   Fig. 31F
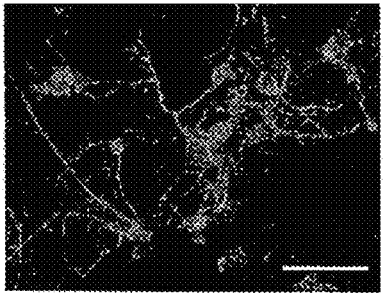 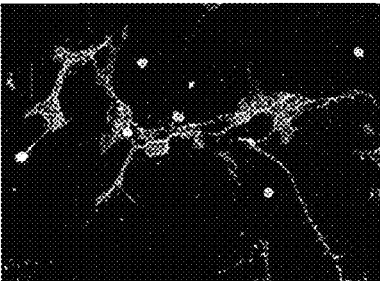 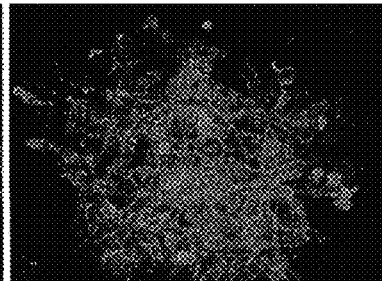
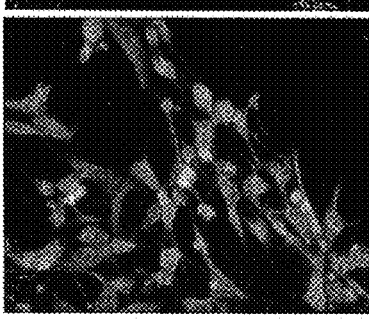 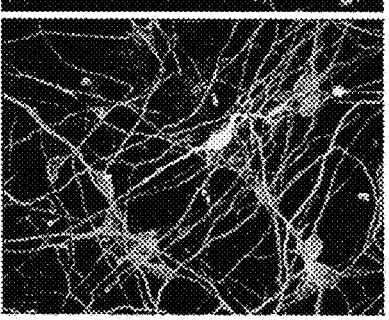 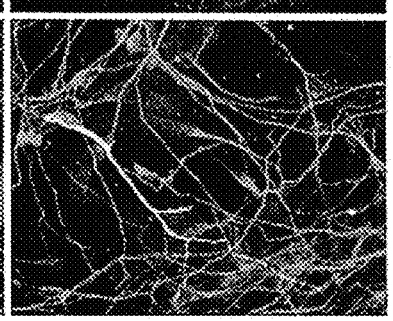
Fig. 31G   Fig. 31H   Fig. 31I

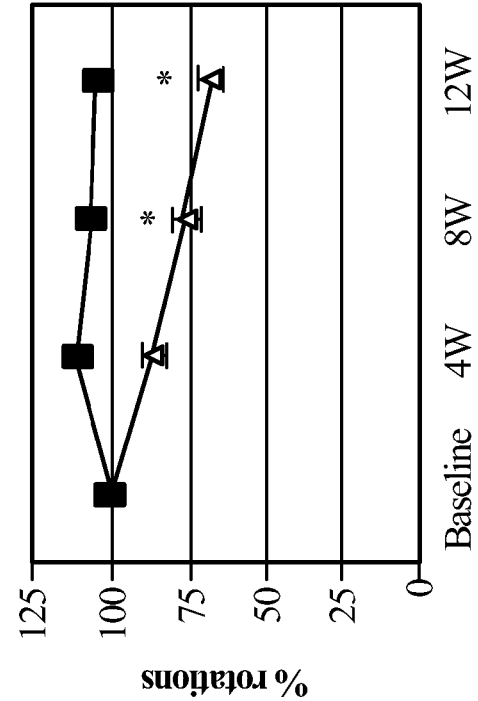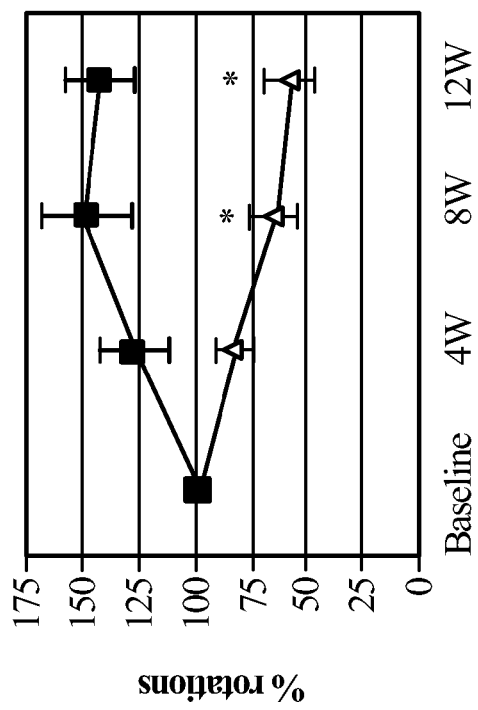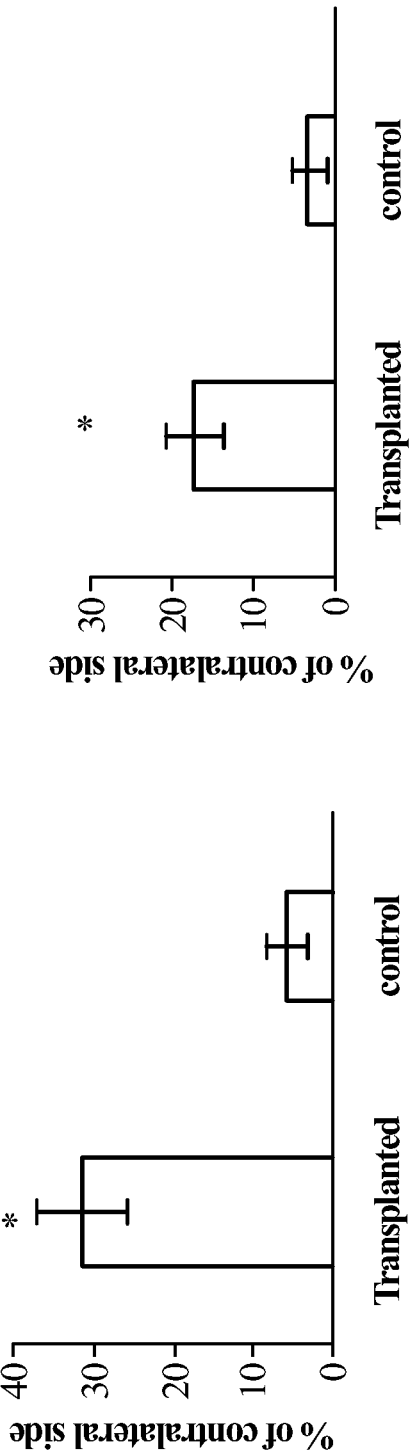
Fig. 35A
Fig. 35B
Fig. 35C
Fig. 35D

GENERATION OF NEURAL STEM CELLS FROM UNDIFFERENTIATED HUMAN EMBRYONIC STEM CELLS

CROSS REFERENCE TO RELATED APPLICATION

This application is a divisional of U.S. Ser. No. 11/005,518, filed on Dec. 3, 2004, which is a continuation of International Application No. PCT AU03/00704, filed Jun. 5, 2003.

FIELD OF THE INVENTION

The present invention relates to the generation of neural cells from undifferentiated human embryonic stem cells. In particular it relates to directing the differentiation of human ES cells into neural progenitors and neural cells and the production of functioning neural cells and/or neural cells of a specific type. The invention also includes the use of these cells for the treatment of neurological conditions such as Parkinson's disease.

BACKGROUND OF THE INVENTION

Embryonic stem (ES) cell lines are derived from the pluripotent cells of the early embryo. These cell lines, potentially, can maintain a normal karyotype through an infinite life span in vitro and their pluripotent stem cells can differentiate into any cell type. ES cell lines derived from human blastocysts allow the study of the cellular and molecular biology of early human development, functional genomics, generation of differentiated cells from the stem cells for use in transplantation or drug discovery and screening in vitro.

The mammalian nervous system is a derivative of the ectodermal germ layer of the post-implantation embryo. During the process of axis formation, it is thought that inductive signals elaborated by several regions of the embryo (the anterior visceral endoderm and the early gastrula organizer) induce the pluripotent cells of the epiblast to assume an anterior neural fate. The molecular identity of the factors elaborated by these issues which direct neurogenesis is unknown, but there is strong evidence from lower vertebrates that antagonists of the Wnt and BMP families of signalling molecules may be involved.

Embryonic stem cells are pluripotent cells which are thought to correspond to the epiblast of the pre-implantation embryo. Mouse ES cells are able to give rise to neural tissue in vitro either spontaneously or during embryoid body formation. The neural tissue often forms in these circumstances in amongst a mixture of a range of cell types.

However, differentiation to a specific neural cell population is required to realize many of the potential applications of ES cells in regenerative medicine of the central nervous system and neuroscience. Alteration of the conditions of culture, or subsequent selection of neural cells from this mixture, has been used in the mouse system to produce relatively pure populations of neural progenitor cells from differentiating cultures of mouse ES cells. These neural progenitors gave rise to the neuronal and glial lineages in-vitro. Transplantation experiments have demonstrated the potential of mouse ES derived neural cells to participate in brain development and to correct various deficits in animal model systems.

Human ES cells have been demonstrated to give rise to neural progenitor cells in vitro and have further demonstrated the capability of the progenitors to differentiate in vitro into mature neurons. In Reubinoff et al, 2000, 2001 PCT/AU99/00990, PCT/AU01/00278 and PCT/AU01/00735 methods are described that allow the derivation of highly enriched (>95%) expandable populations of proliferating neural progenitors from human ES cells. The neural progenitors could be induced to differentiate in vitro into astrocyte, oligodendrocyte and mature neurons. Transplantation experiments demonstrated the potential of the neural progenitors to integrate extensively into the developing host mouse brain, to respond to local host cues, and to construct the neuronal and glial lineages in vivo (Reubinoff et al., 2001, PCT/AU01/00278).

To derive the neural progenitors, mixed somatic differentiation was induced by prolonged culture of undifferentiated human ES cells without replacement of the mouse embryonic fibroblast feeder layer (Reubinoff et al 2000, 2001 PCT/AU99/00990, PCT/AU01/00278). Under these culture conditions, distinct areas comprised of small piled, tightly packed cells that do not express markers of undifferentiated ES cells or early neuroectodermal progenitors were formed among many other cell types. When these areas were mechanically removed and further cultured in defined media that promote the propagation of neural progenitors, they gave rise to the highly enriched preparations of the neural progenitors.

Recently, others have also reported the derivation of neural progenitors from human ES cells (Zhang et al., 2001, Carpenter et al., 2001). However, these authors induced non-specific mixed differentiation of human ES cells by the formation of embryoid bodies (EBs). Following plating of the EBs and culture in defined medium supplemented with mitogens, enrichment for neural progenitors was accomplished by cell sorting or selective separation following enzymatic digestion. Directed differentiation of human ES cells into neural progenitors and further into specific types of neural cells was not reported by these authors.

Directed differentiation of human ES cells into neural progenitors and further on into specific types of neural cells may be highly valuable for basic and applied studies of CNS development and disease. Controlled differentiation of human ES cells into the neural lineage will allow experimental dissection of the events during early development of the nervous system, and the identification of new genes and polypeptide factors which may have a therapeutic potential such as induction of regenerative processes. Additional pharmaceutical applications may include the creation of new assays for toxicology and drug discovery, such as high-throughput screens for neuroprotective compounds. Controlled generation of neural progenitors and specific types of neurons or glia cells from human ES cells in vitro may serve as an unlimited donor source of cells for tissue reconstruction and for the delivery and expression of genes in the nervous system.

Directed differentiation of human ES cells into neural progenitors, has been demonstrated with the bone morphogenetic protein antagonist noggin in Pera et al., 2001 and PCT/AU01/00735. Treatment of undifferentiated human ES cell colonies that were cultured on feeders with noggin blocked differentiation into extra embryonic endoderm and uniformly directed the differentiation into a novel cell type ("noggin cells"). Noggin cells are similar in terms of morphology and lack of expression of markers of undifferentiated stem cells or neural progenitors to the small piled, tightly packed cells that were obtained within a mixture of other cell types in high density cultures.

When noggin cells were transferred to defined culture conditions they gave rise to neural progenitors, neurons and glial cells.

A major application of human ES cells may be their potential to serve as a renewable unlimited donor source of cells for transplantation. However, the potential use of human ES cell derived neural cells in regenerative medicine will depend on their capability to restore function. So far the potential of human ES cell derived neural cells to restore function after transplantation has not been demonstrated.

In the mouse, ES cell derived progeny may be functional. Transplantation of low doses of undifferentiated mouse ES cells into the rat striatum results in their differentiation into dopaminergic neurons and restoration of cerebral function and behavior in animal model of Parkinson's disease (Bjorklund et al 2002). Nevertheless, it should be noted that teratoma tumors were observed in 5 of 22 transplanted animals and in 6 grafted rats no surviving ES cells were found. Teratoma formation and the relatively low survival rate post transplantation preclude the clinical utilization of this approach.

Parkinson's disease is the second most common neurodegenerative disorder affecting over one million patients in the USA. Pharmacological treatments of the disorder, mainly with L-dopa, have limited long term success and are associated with serious motor side effects. Transplantation of dopaminergic neurons (DA neurons) is an alternative approach that potentially may overcome the drawbacks of pharmacological treatments (Lindvall 1997). Clinical trials of transplantation of fetal derived DA neurons into Parkinson's patients show clinical benefits in some patients (Bjorklund and Lindvall 2000; Freed et al., 2001). Nevertheless, the ethical and practical problems of obtaining sufficient fetal donor tissue severely limit widespread application of this mode of therapy. In vitro production of transplantable dopaminergic cells at a large scale could circumvent this drawback. A potential source for the unlimited generation of transplantable dopaminergic neurons in vitro is embryonic stem (ES) cell lines.

The potential of ES cells to serve as an unlimited donor source of dopaminergic neurons (DA) has been demonstrated in the mouse ES cell system (Lee at al 2000, Kawasaki at al 2000).

Furthermore, functional recovery following transplantation of mouse ES cell-derived DA neurons into an animal model of Parkinson's disease was recently demonstrated (Kim et al., 2002). However, it is known in the art of biology that murine and human ES cells are different in many aspects. Accordingly, methods that are efficient with mouse ES cells may be unsuitable for human pluripotent stem cells. For example, the cytokine leukemia inhibitory factor (LIF) can support undifferentiated proliferation of mouse ES cells (Robertson E 1987) while it has no effect on human ES cells (Reubinoff et al., 2000).

FGF8 and SHH signals control dopaminergic cell fate in the anterior neural plate. In the mouse, expansion of mouse ES cell derived neural progenitors in the presence of FGF8 and/or SHH significantly increases the generation of DA neurons (Lee et al 2000). The combination of SHH and FGF8 fails to induce significant dopaminergic differentiation of neurons that are derived from human EC cells (NT2/hNT, Stull and Lacovitti 2001). This further enhances the differences between human and mouse. Human EC cells resemble human ES cells (Pera M F 2000), and their lack of response may suggest that pluripotent stem cells from a human origin as opposed to their mouse counterpart do not respond to the SHH/FGF8 combination.

Human ES cells can spontaneously differentiate into tyrosine hydroxylase (TH) producing neurons (PCT/AU01/00278, Reubinoff et al., 2001). However, there has been no demonstrated control for the production of dopaminergic neurons at high yields from human ES cells and more importantly the directed differentiation toward a cell type which has the potential for transplantation and treatment of neurological conditions.

Accordingly, it would be desirable to direct the differentiation of human ES cells toward a useful cell type and to generate the cell type in high yield to improve the chances of successful transplantation.

Therefore, it is an object to overcome some of these practical problems and problems of the prior art.

SUMMARY OF THE INVENTION

In a first aspect of the present invention there is provided a method of directing the fate of undifferentiated hES cells towards neural progenitor cells in vitro said method including the steps of:
  culturing undifferentiated human ES cells in a defined serum free medium that contains FGF-2 and an antagonist of bone morphogenic proteins (BMP).

In this method, the differentiation of human ES cells is directed into a neural fate and differentiation towards other lineages is eliminated.

In another aspect of the present invention there is provided a non-committed culture of neural progenitor cells prepared by this method as well as isolated non-committed neural progenitor cell derived from this method.

In yet another aspect of the present invention there is provided a method of directing neural fate in a human embryonic stem (hES) cell in vitro said method comprising the steps of:
  obtaining a neural progenitor cell from a hES cell culture; and
  culturing the neural progenitor cell in the presence of a neural fate inducer selected from the group including at least one of Fibroblast Growth Factor (FGF), Sonic Hedgehog Protein (SHH), cAMP inducers, Protein Kinase C (PKC) inducers, dopamine and ascorbic acid (AA) or any combination thereof.

The present method provides for a controlled differentiation of neural progenitors, preferably towards a transplantable neural cell that establishes in a predetermined region of the body. Highly enriched preparations of these cells may be obtained by the methods described herein. The newly derived cells have improved transplantability and are more potent in vivo.

This improved potency translates to improved survival and/or function of the differentiated cells upon transplantation.

In another aspect of the present invention there is provided a method of directing neural fate in a human embryonic stem (hES) cell in vitro said method comprising the steps of:
  obtaining a neural progenitor cell from a hES cell culture; and
  inducing an overexpression of Nurr 1 and/or Lmx1b in the hES cell.

Without being limited by theory, applicants propose that the overexpression of the Nurr1 and/or Lmx1b gene can direct the differentiation of hES cells toward a neural fate and DA neurons. Applicants have shown that the hES cells that have differentiated toward the neural fate show an over-expression of the Nurr1 gene. The expression is maintained during differentiation into neurons that co-express Nurr1 and TH.

The Nurr 1 and/or Lmx 1b expression may be induced by any methods available to the skilled addressee. Preferably, the gene(s) are introduced by genetic modification. The gene(s)

may be introduced by a suitable vector under the influence of an inducer such that when differentiation is to be effected, expression of the gene may be induced by introduction of the inducer to the cell culture.

In another aspect of the invention, there is provided a method of enhancing the survival of transplanted DA neurons said method comprising obtaining a neural progenitor cell from a hES cell culture or a cell differentiated from the neural progenitor; and inducing an expression of GDNF and/or BDNF in the neural progenitor cell or a cell differentiated from the neural progenitor.

Without being limited by theory, Applicants propose that a forced expression of GDNF and/or BDNF by the transplanted hES cells or their neural progeny may enhance the survival of transplanted DA neurones. Preferably the expression is an over-expression above a level that is naturally present.

The neural progenitors may be according to the neural progenitors described above. They may be genetically modified to include vectors that express GDNF and/or BDNF and which may be under the influence of an inducer that can be switched on at an appropriate time to enhance the survival of the transplanted cell.

In yet another aspect of the present invention there is provided a genetically modified hES cell that has been prepared by the methods described above. Preferably, the cell can differentiate to a glial cell and can preferably be directed to differentiate upon forced expression of the Nurr1 and/or Lmx 1b gene and/or the GDNF and/or BDNF survival factors.

The present invention also contemplates transgenic animals having the modified genes.

In a further embodiment, the invention includes methods of treating neural conditions using the genetically modified hES cell, said method comprising transplanting the genetically modified hES cell and inducing the expression of the Nurr1 and/or Lmx 1b gene and/or the GDNF and/or BDNF survival factors.

The method describes "directing neural fate". This term as used herein means to guide the differentiation and development of neural progenitors preferably toward a midbrain fate, or toward neuronal cell types, preferably neurons that show characteristics typical of midbrain neurons. The method may be used to generate any neural progenitor or neuronal subtype including but not limited to hES derived motor neurons, GABAergic, glutamerigic, cholinergic, dopaminergic and serotonergic neurons. The method preferably directs a midbrain neural fate to the neural progenitors derived from hES cells. More preferably the neural progenitor cell is committed to a midbrain fate, tyrosine-hydroxylase (TH) positive (TH$^+$) cell or doparminergic cell.

In a preferred aspect of the present invention there is provided a method of directing midbrain fate to a hES cell in vitro, said method comprising the steps of:

obtaining a neural progenitor cell from a hES cell culture; and culturing the neural progenitor cell in the presence of a midbrain fate inducer selected from the group including any one of FGF-1, FGF-8, FGF-17, SHH, AA, cAMP inducers, PKC inducers and dopamine or any combination thereof.

It is most preferred that the midbrain fate inducer is a combination of FGF-1, FGF-8, FGF-17, SHH, IBMX, forskolin, PMA/TPA and dopamine. Various other combinations may be useful including the combination of:
(i) FGF-8 and SHH, IBMX, forskolin, PMA/TPA and dopamine; or
(ii) FGF-17 and SHH, IBMX, forskolin, PMA/TPA and dopamine; or
(iii) FGF-1, and IBMX, forskolin, PMA/TPA and dopamine; or
(iv) FGF-8 alone; or
(v) FGF-17 alone; or
(vi) IBMX, forskolin, PMA/TPA, and dopamine.

In a further preferred embodiment, the method further includes culturing the neural progenitor in the presence of ascorbic acid (AA) or an analogue thereof.

In an even further preferred embodiment, the method further includes culturing the neural progenitor in the presence of NT4 or equivalent thereof such as NT3.

In yet an even further preferred embodiment, the method includes the further step of:

culturing the neural progenitor cells on poly-D-lysine and laminin.

The neural progenitor may also be in the form of neurospheres.

In another aspect of the present invention there is provided a cell culture comprising neural progenitors committed to a neural fate, preferably a midbrain fate. Preferably the neural progenitors are in aggregates or sphere structures.

More preferably when these aggregates are induced to differentiate at least 30% of them give rise to a significant number (>50) of TH+ neurons. The proportion of clumps containing TH+ cells may increase to at least 60% when the midbrain fate of the progenitors is enhanced by midbrain inducers as detailed above.

Preferably, the neural progenitors with a midbrain fate induced by exposure to midbrain fate inducers express mRNA of key genes in the development of midbrain and dopaminergic neurons, and give rise to TH$^+$ neurons or dopaminergic neurons.

In another aspect of the present invention, there is provided an isolated human neural progenitor cell having a committed neural fate more preferably a committed midbrain fate. Preferably the cell can differentiate into a TH$^+$ neuron or a dopaminergic neuron. Most preferably, the cell is prepared by methods described herein and isolated from a culture of differentiated hES cells that have been induced to differentiate toward a midbrain fate by the use of midbrain fate inducers described herein.

In another aspect of the present invention, there is provided an isolated human neuronal cell having a committed neural fate, more preferably to a committed midbrain fate. Preferably the cell is TH$^+$ neuron or a dopaminergic neuron. Most preferably, the cell is prepared by methods described herein and isolated from a culture of differentiated hES cells that have been induced to differentiate toward a midbrain fate by the use of midbrain fate inducers described herein.

In another aspect of the present invention there is provided a human neural fate inducer composition for inducing neural fate in a cultured hES cell, said composition comprising a neural fate inducer selected from the group including Fibroblast Growth Factor (FGF), ascorbic acid (AA), Sonic Hedgehog Protein (SHH), cAMP inducers, Protein Kinase C (PKC) inducers and dopamine or any combination thereof.

In yet another aspect of the present invention, there is provided a method of treating a neurological condition in an animal, said method comprising administering an effective amount of an in vitro derived neural progenitor cell to the animal. Preferably, the neural progenitor is derived from an undifferentiated hES cell and is not committed to a neural fate. More preferably the neural progenitor cells have a committed neural fate. Most preferably, the neural progenitors are committed to a midbrain fate.

The commitment of the neural progenitors to a midbrain fate may be determined by demonstrating that the neural progenitors express key genes in the development of midbrain and dopaminergic neurons in vivo.

In a preferred embodiment, the neurological condition is Parkinson's disease.

FIGURES

The patent or application file contains at least one drawing executed in color. Copies of this patent or patent application publication with color drawing(s) will be provided by the Office upon request and payment of the necessary fee.

FIG. 1 shows dark field images of hES colonies treated with noggin two weeks after passage. (A) A colony mainly comprised of areas of small tight cells (B) A colony with presumably neural rosettes.

FIG. 2 shows characterization of cells within areas that are presumably neural rosettes. Fluorescent images of immunostaining for the markers (A) N-CAM and (B) nestin. A very high proportion of the cells express these markers.

FIG. 3 shows phase contrast micrograph of neurospheres at various times after derivation. The spheres gradually acquired in culture a round uniform appearance. Spheres generated from noggin treated colonies at 15 (A) and 27 (B) days after derivation. Spheres at 1 (C) and 7 (D) days after transfer of hES cell clumps to neural progenitor medium supplemented with noggin.

FIG. 4 shows characterization of the phenotype of cells within spheres three weeks after transfer of hES cell clumps into neural progenitor medium with or without noggin. The proportion of cells that express markers of neuroectoderm, endoderm and mesoderm was evaluated by immunostaining. A high percentage of the cells within the spheres express early neural markers. Noggin treatment reduced in a dose dependent manner the percentage of cells expressing markers of endoderm and mesoderm.

Figure 10:
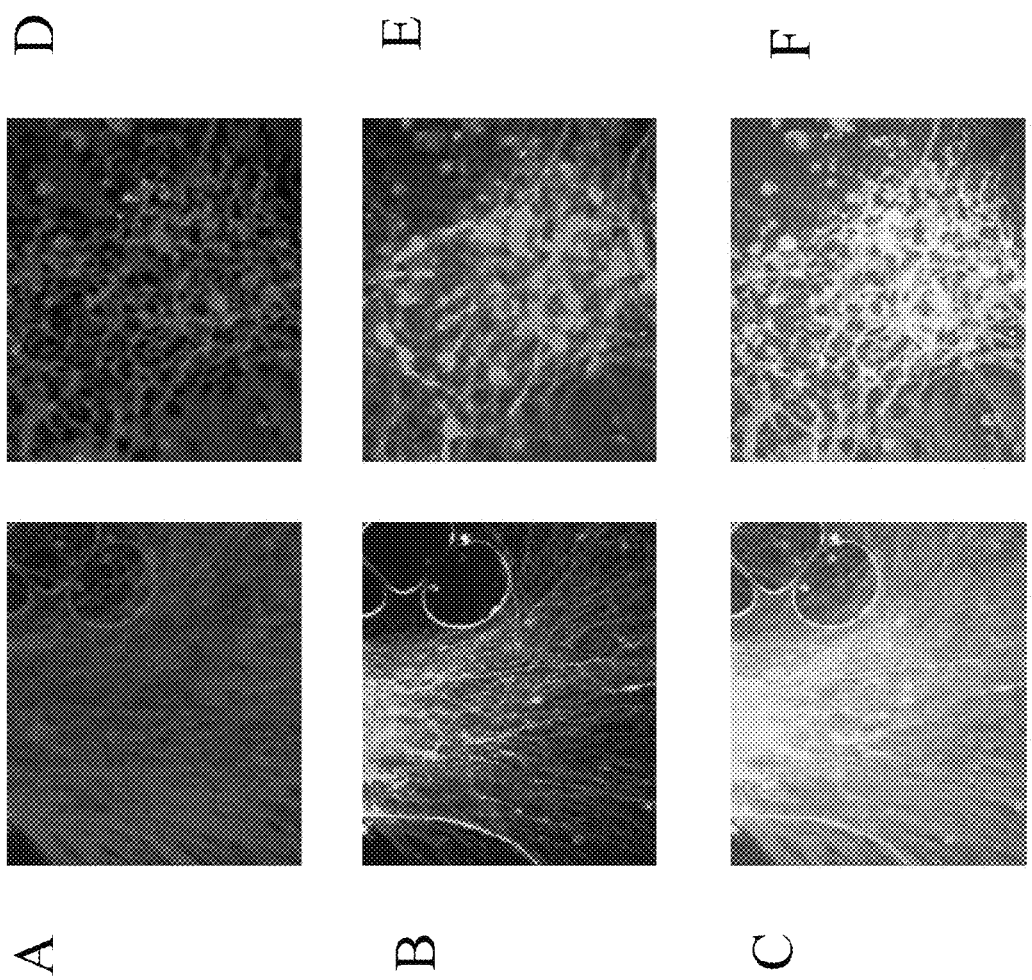

FIG. 10 shows fluorescent images of differentiated clumps of neural cells after treatment with FGF8, SHH and AA and plating on laminin in the presence of AA. A large proportion of the cells express the neuronal marker β-tubulin type III (A, D red). A significant number of the cells are immunoreactive with anti TH (B, E, green). Images of double staining for both markers show that TH+ cells coexpress β-tubulin type III (C, F, yellow)

Figure 11:
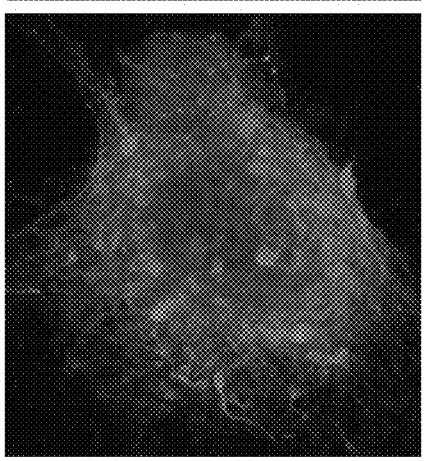
Figure 11:
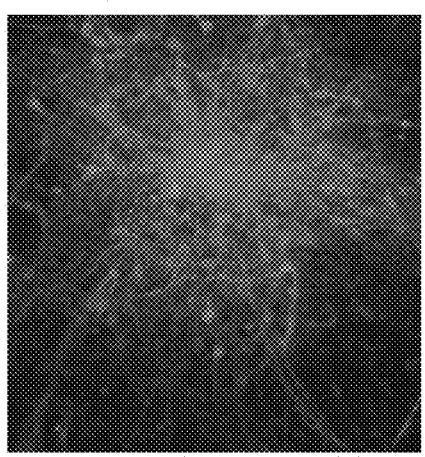
Figure 11:
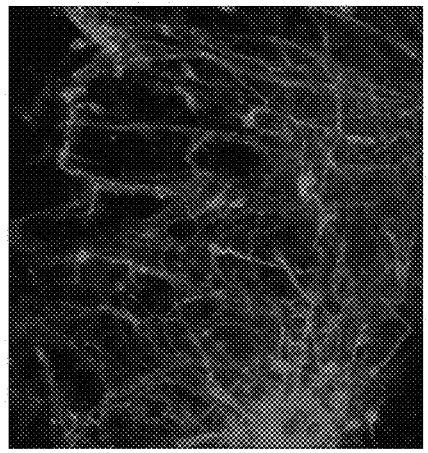
Figure 11:
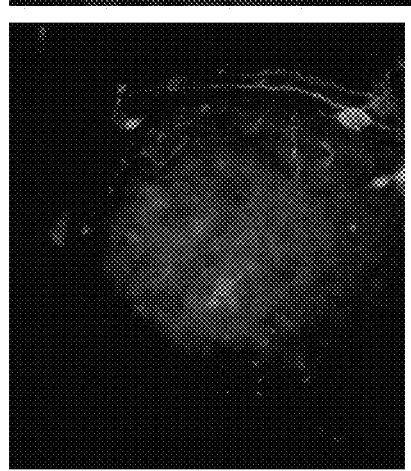
Figure 11:
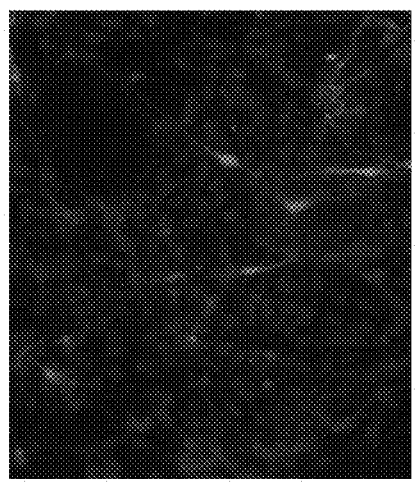

FIG. 11 shows fluorescent images of differentiated clumps of neural progenitors after treatment with FGF17 and AA. A significant proportion of the cells are immunoreactive with anti TH (A-C) while sparse TH+ cells are observed within non-treated lumps (D, E).

Figure 12:
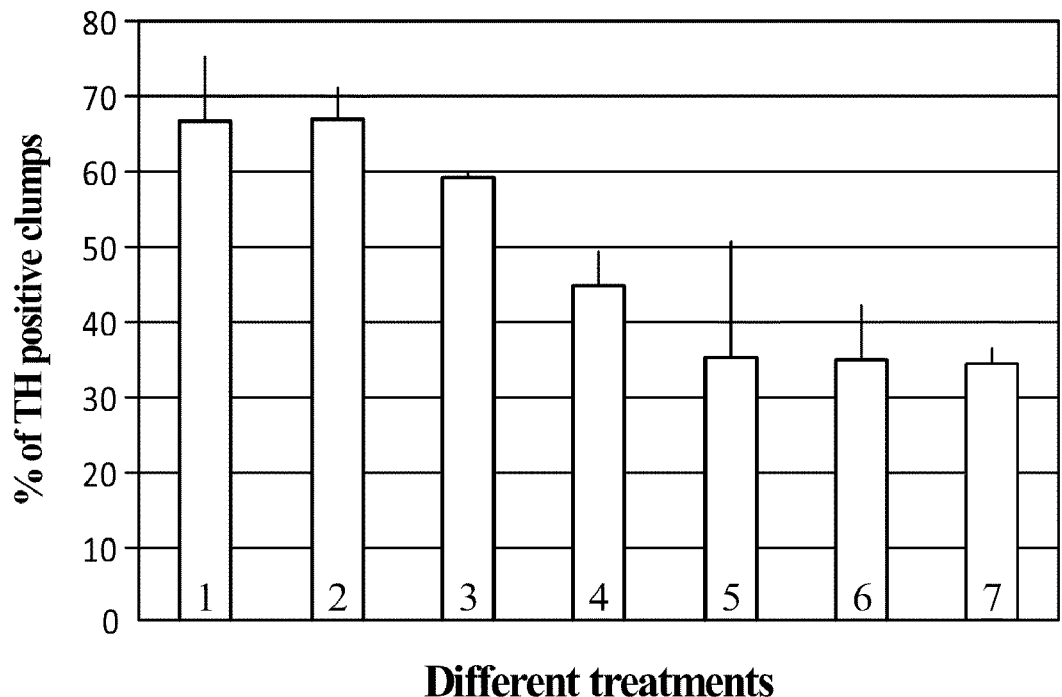

FIG. 12 shows the effect of various combinations of external factors on the proportion of TH+ clumps. Clumps with >50 TH+ cells were scored as TH+ ones. Each bar represents 2-3 experiments. 50-150 clumps were scored in each experiment.

Figure 13:
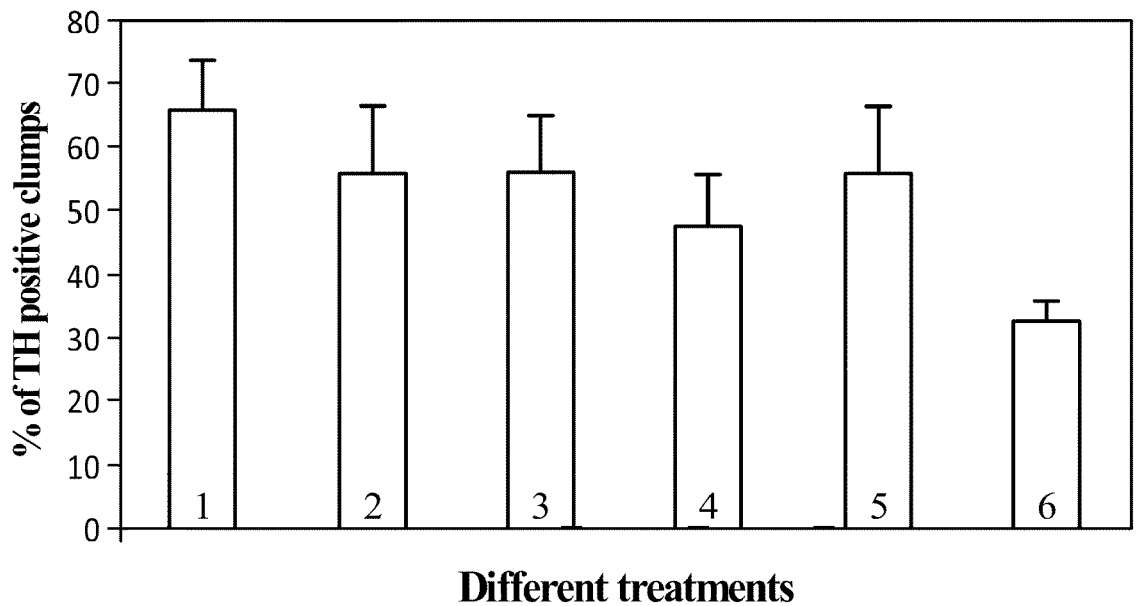

FIG. 13 shows the effect of treatment with FGF-1, IBMX, forskolin, PMA (TPA), dopamine and AA on the generation of TH+ clumps. Clumps with >50 TH+ cells were scored as TH+ ones. Each bar represents the scoring of 65-200 clumps.

Figure 14:
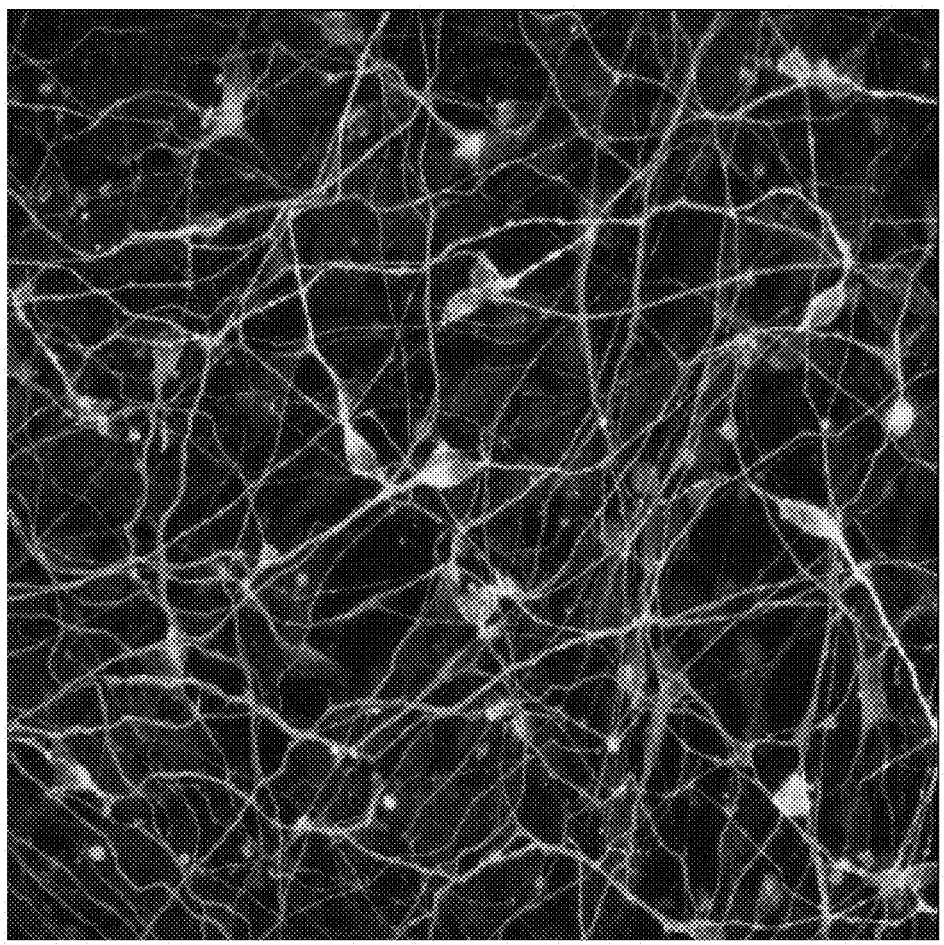

FIG. 14 shows a confocal microscopy image of double immunostaining for TH (green) and β-tubulin type III (red). Neurospheres that were propagated for 5 weeks, were plated on laminin and allowed to differentiate for a week in the presence of ascorbic acid. The image is a projection of multiple confocal microscopy images of consecutive planes through the differentiating clumps of neural cells.

Figure 15:
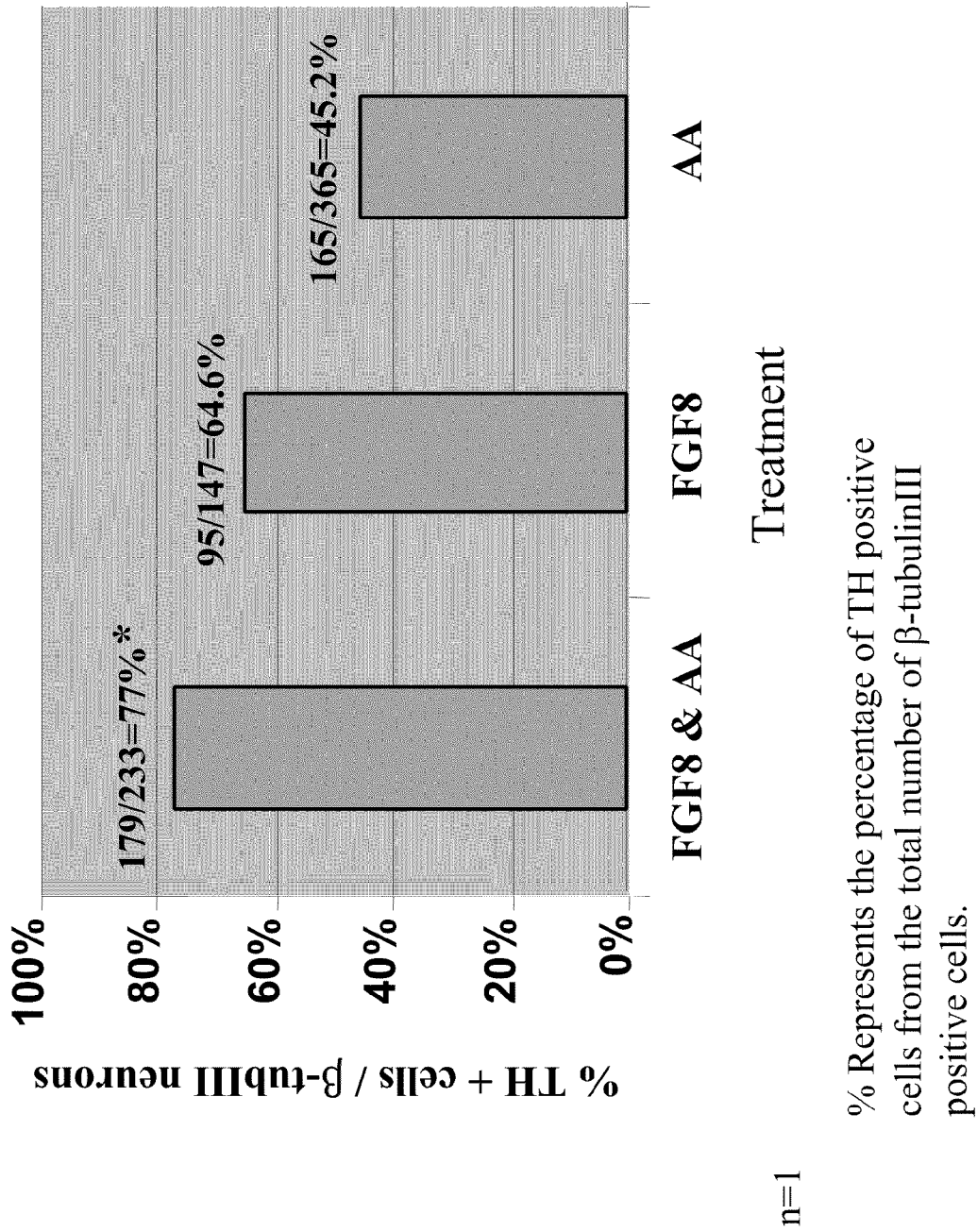

FIG. 15 shows the percentage of neurons expressing TH following treatment with FGF8 and AA. Neural spheres were plated on laminin in the absence of mitogens and treated with AA, FGF8 or both AA and FGF8 for a week. The neural spheres were then further cultured for an additional week in the presence of AA. Each bar represents confocal imaging analysis of 150-300 cell bodies for the expression of TH and β-tubulin III within 10-15 random fields.

Figure 16:
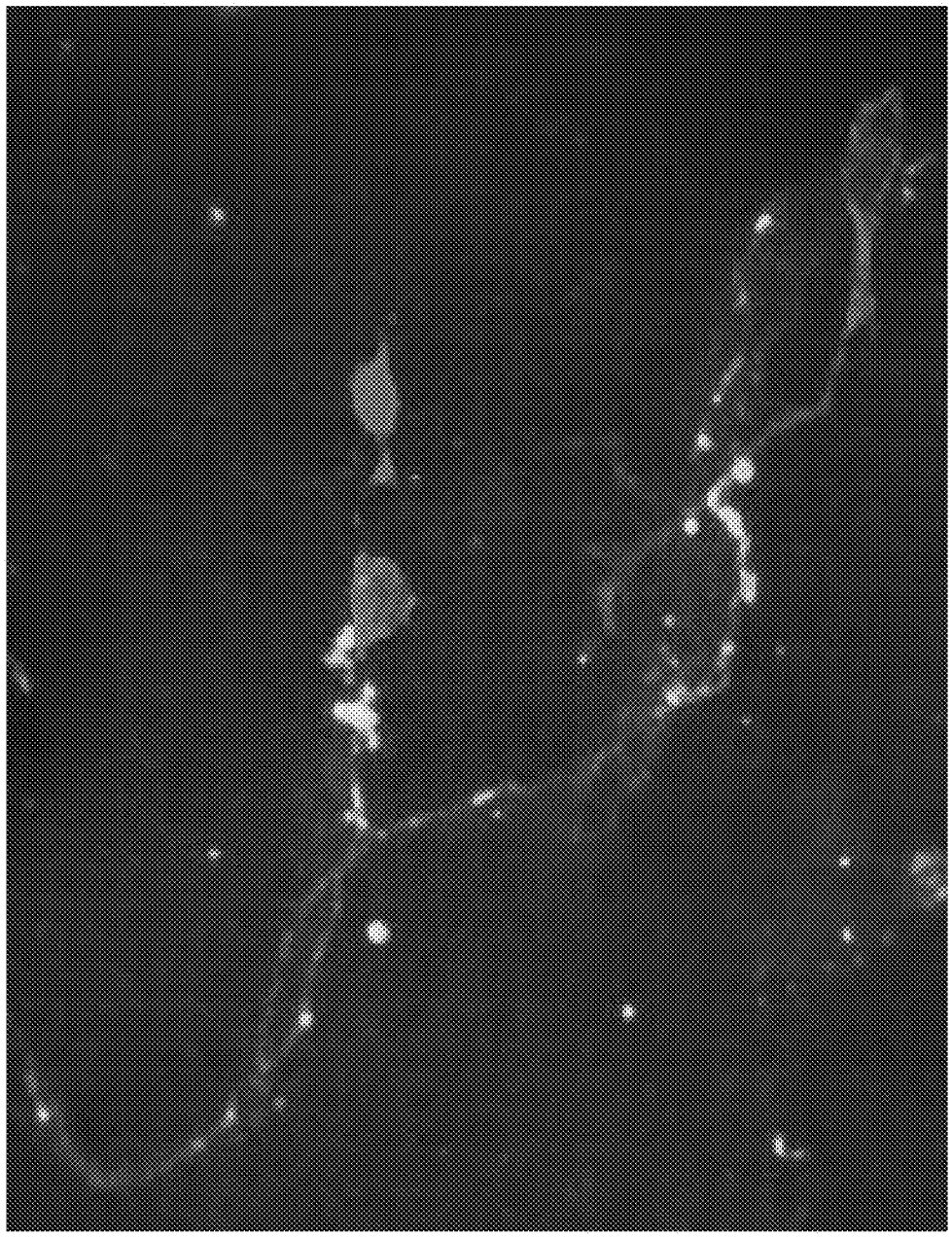

FIG. 16 shows indirect immunofluorescence images of differentiated neurons decorated with anti TH and anti DAT antibodies.

Figure 17:
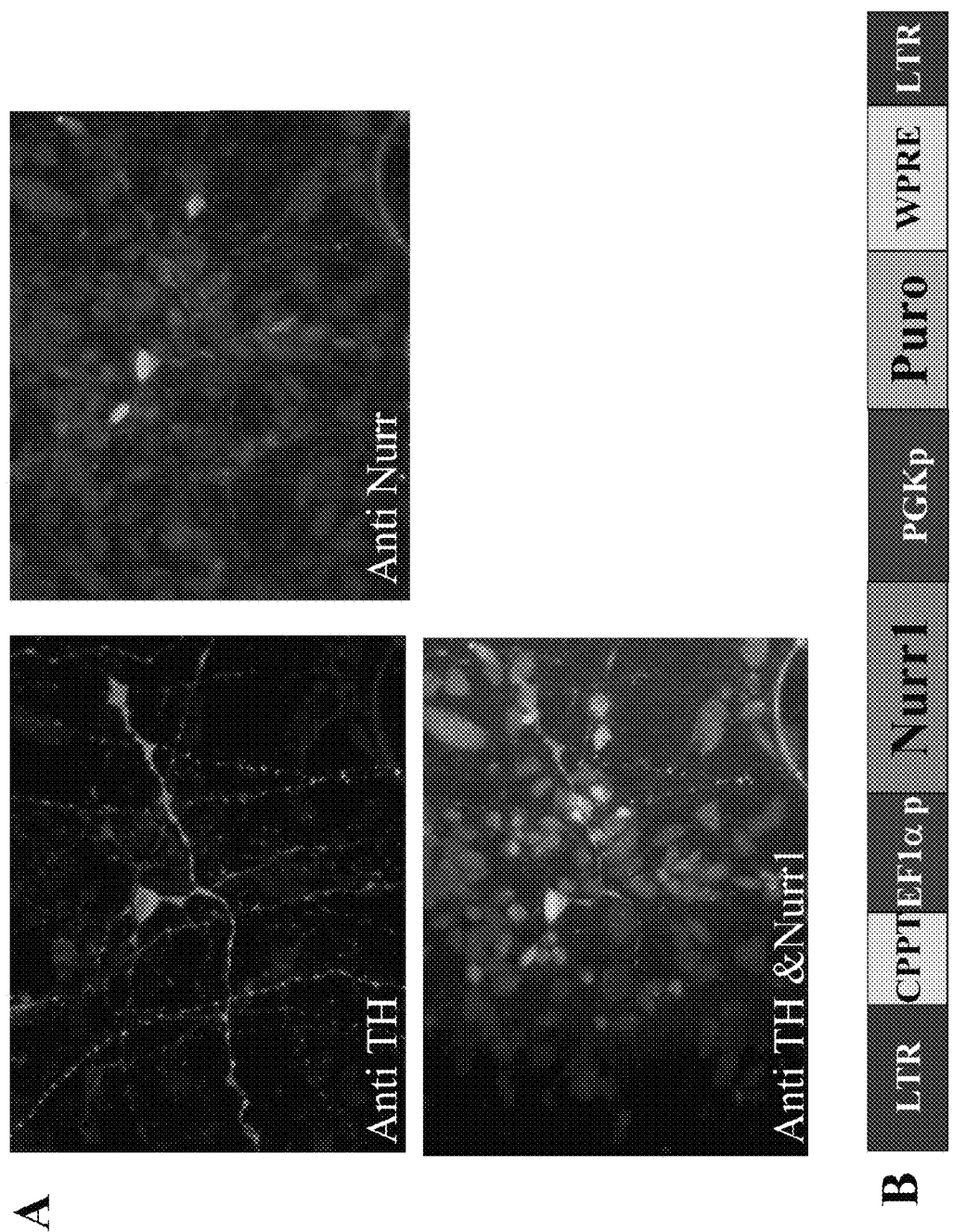

FIG. 17 shows indirect immunofluorescence images of a differentiated neuron coexpressing Nurr1 and TH (A). The neuron was developed from transduced hES cells over-expressing Nurr1. Schematic presentation of the lentiviral vector that was used to force the expression of Nurr1 is presented in B.

Figure 18:
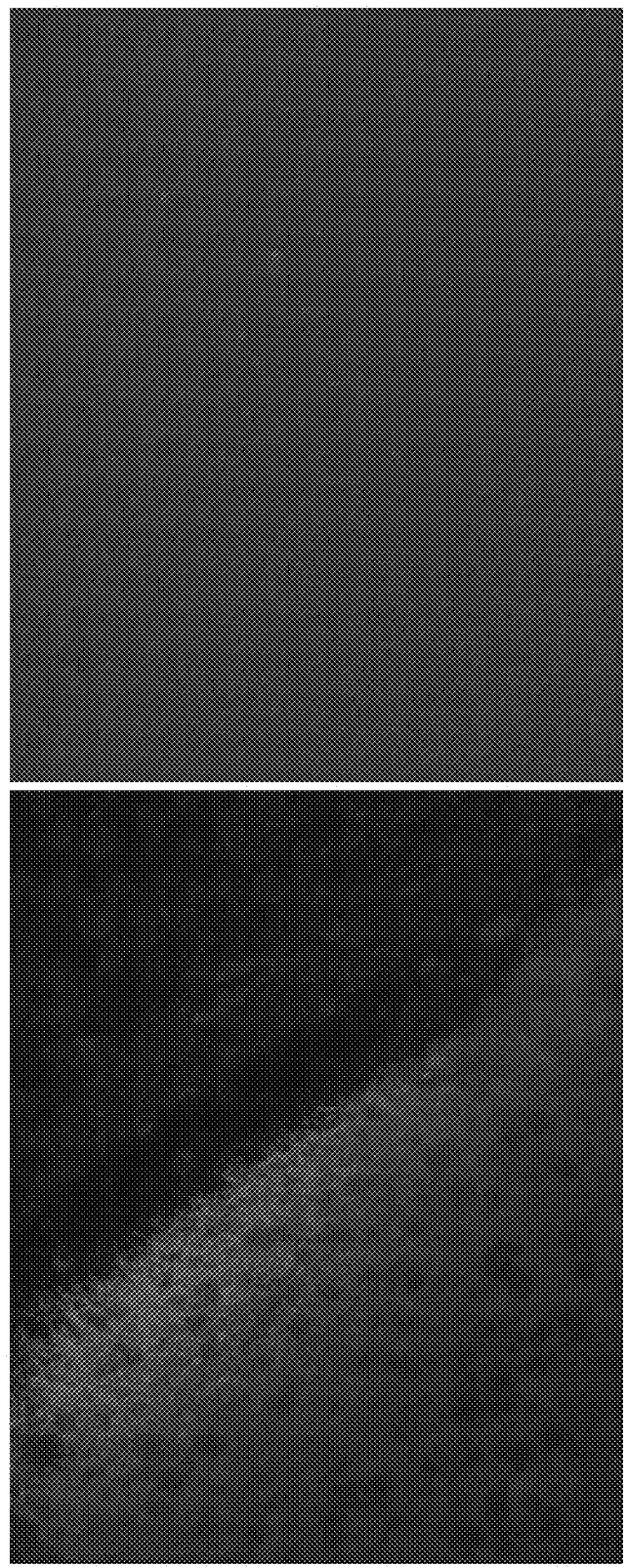

FIG. 18 shows indirect immunofluorescent analysis of TH expression in the 6-OH dopamine lesioned rat striatum and in the intact striatum of contralateral side.

Figure 19:
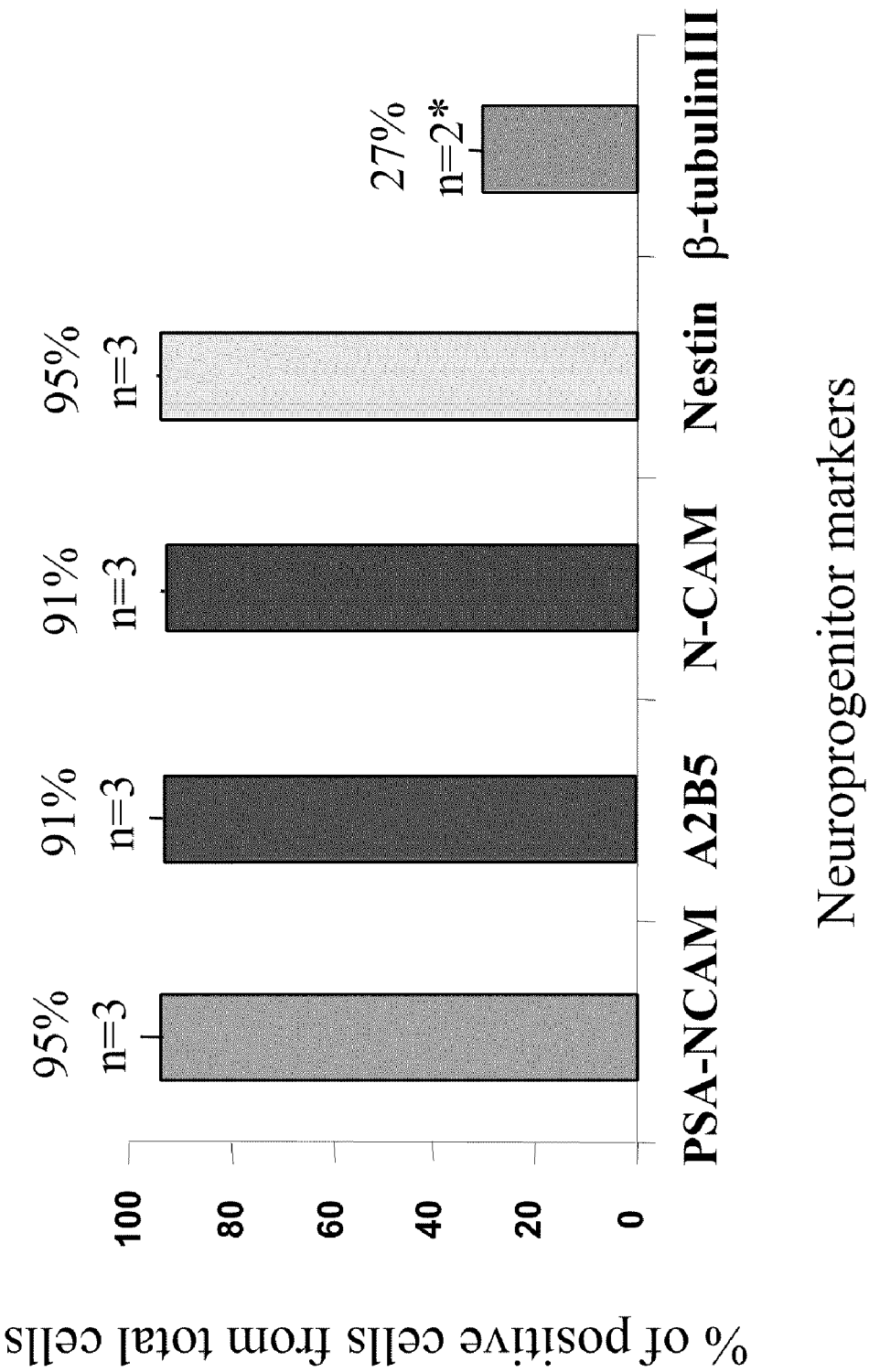

FIG. 19 shows the percentage of cells expressing neural progenitor markers within spheres prior to transplantation. Progenitor cells were analyzed by indirect immunofluorescence for the expression of markers 12-24 h after disaggregating of spheres and plating on an adhesive substrate. 93-94% of the progenitors expressed the early neural markers and 27% expressed the neuronal marker β-tubulin type III. The bars represent results from three independent experiments.

Figure 20:
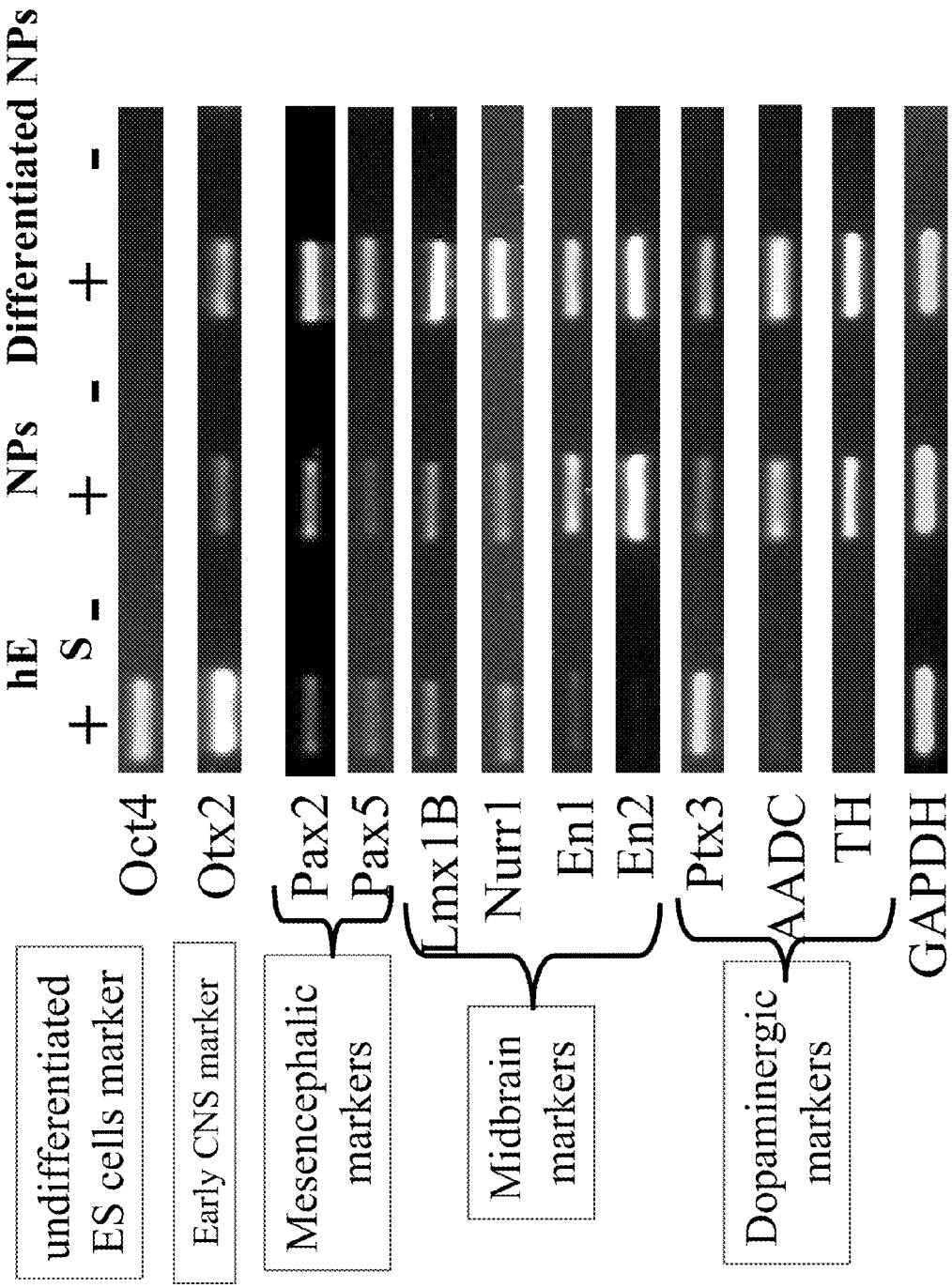

FIG. 20 shows RT-PCR analysis of expression of regulatory genes of development of ES cells, early CNS, midbrain and dopaminergic neuron by neural progenitors and their differentiated progeny. The symbols + and − indicate whether the PCR reaction was done with or without the addition of reverse transcriptase. HES—mainly undifferentiated hES cell colonies; NPs—neural progenitors after 6 weeks in culture and prior to transplantation.

Figure 21:
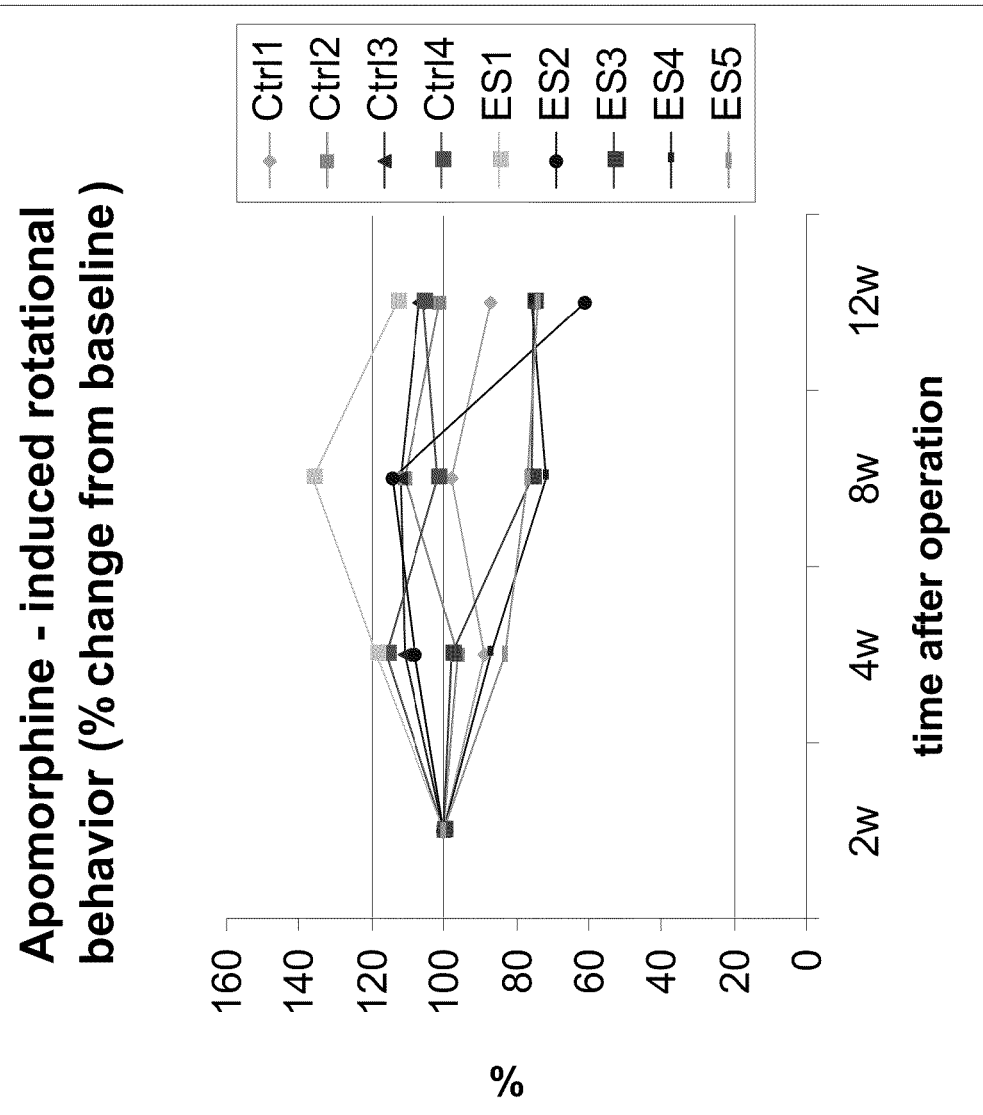

FIG. 21 shows apomorphine-induced rotational behavior in individual sham operated and human neurosphere transplanted Parkinsonian rats. Data is given as percent change in comparison to each rat rotational behavior at 2 weeks after transplantation. At this time point the rats exhibited the full effect of the 6-hydroxydopamine lesions as determined by apomorphine induced rotational behavior. At 12 weeks, all sham-transplanted rats (Ctrl 1-4) showed no difference in rotational behavior as compared to baseline. In 4 out of 5 human neurosphere transplanted rats (ES 2-5) there was a significant decrease in rotational behavior.

Figure 22:
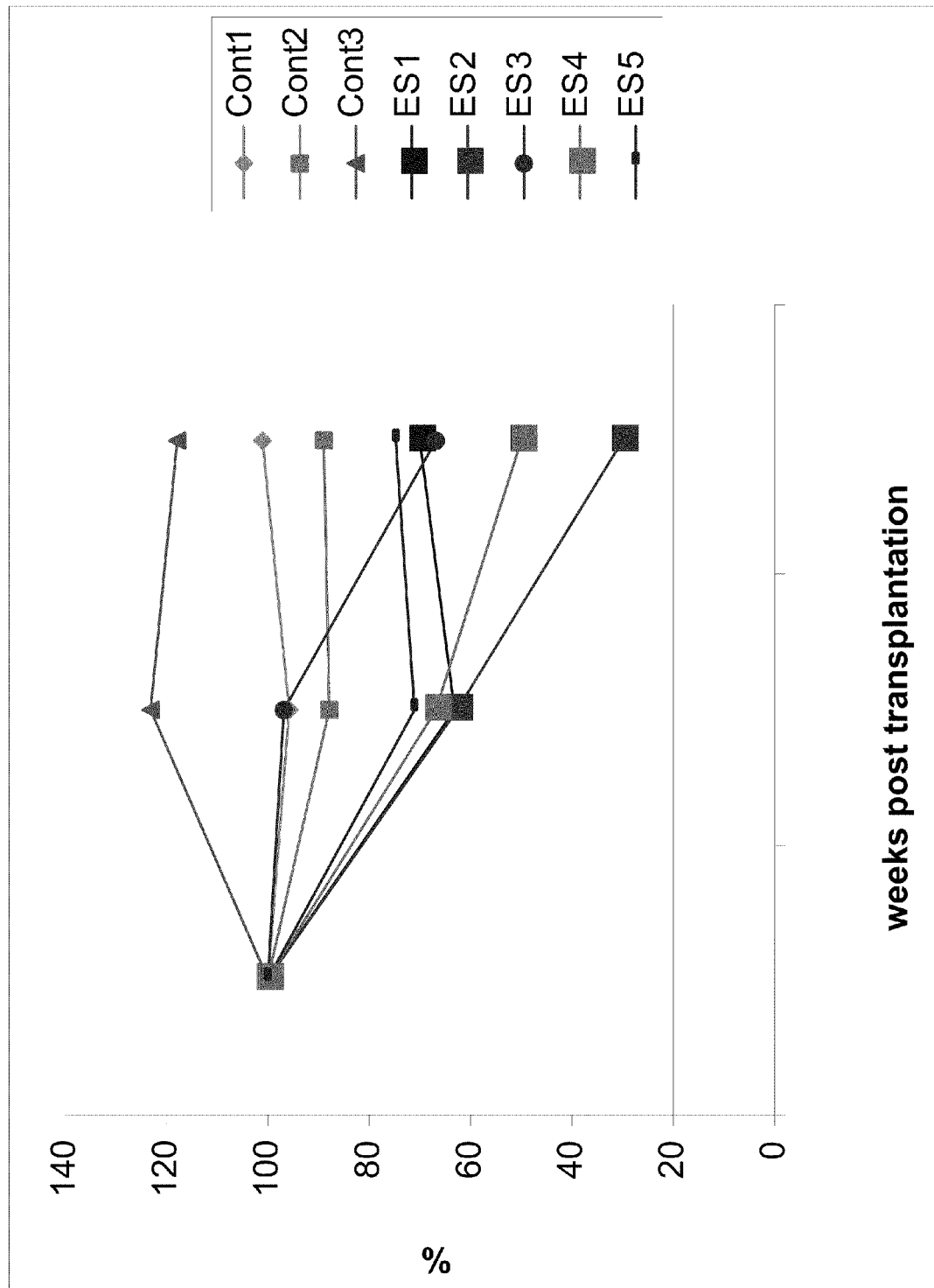

FIG. 22 shows apomorphine-induced rotational behavior in individual sham operated and human neurosphere transplanted Parkinsonian rats. In this experiment, neurospheres that were passaged for 5 weeks prior to transplantation were used. Data is given as percent change in comparison to each rat rotational behavior at 2 weeks after transplantation. At this time point the rats exhibited the full effect of the 6-hydroxydopamine lesions as determined by apomorphine induced rotational behavior. At 8 weeks, all sham-transplanted rats (Ctrl 1-3) showed no difference in rotational behavior as compared to baseline. In all 5 human neurosphere transplanted rats (ES 1-5) there was a significant decrease in rotational behavior.

Figure 23:
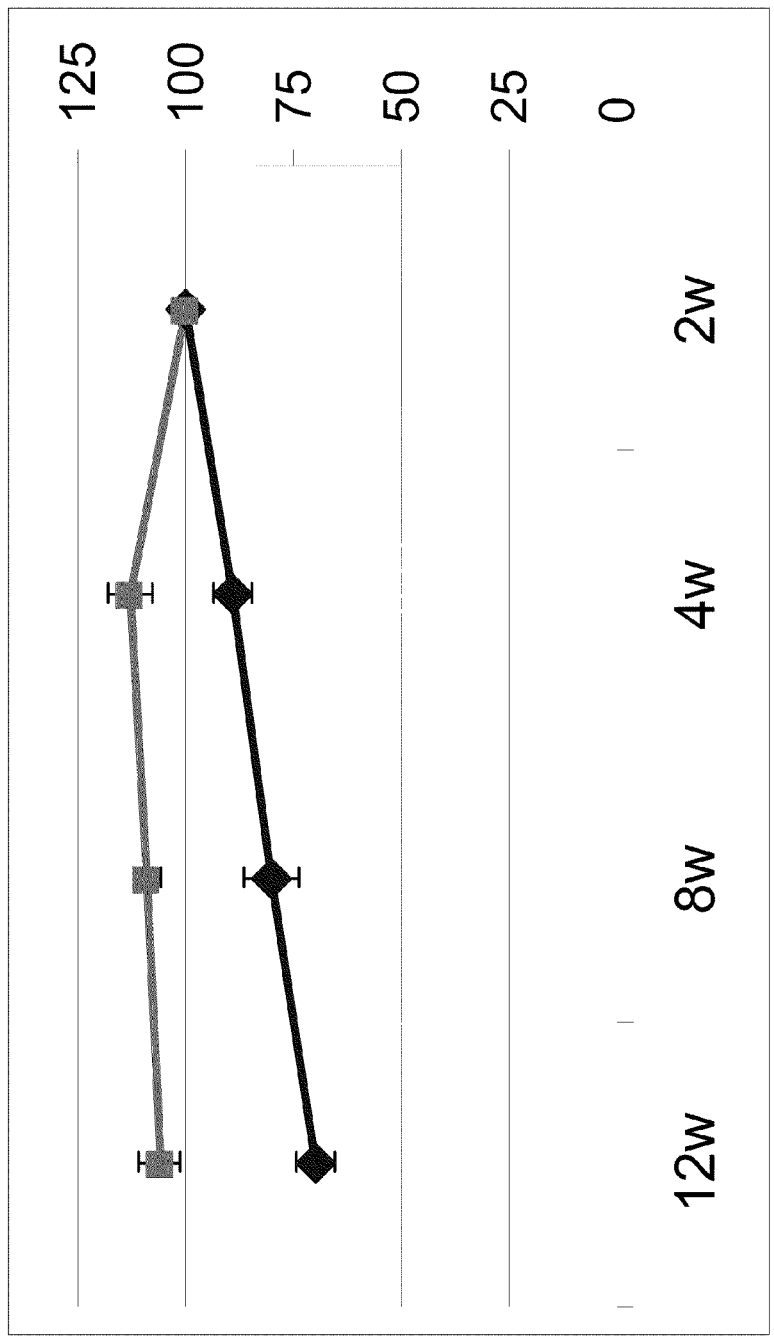

FIG. 23 shows apomorphine-induced rotational behavior in sham operated and human neurosphere transplanted Parkinsonian rats. At 2, 4, 8 and 12 weeks after transplantation, the severity of the disease was scored and compared between hES cell-transplanted (♦; n=16) and vehicle-transplanted (□; n=12) animals by quantification of rotational behavior in reaction to apomorphine.

Data is presented as percent change (mean±SEM) in comparison to rotational behavior at 2 weeks after transplantation. At this time point, the rats exhibited the full effect of the 6-OH-DA lesions. A significant decrease in rotational behavior was observed in transplanted animals (70% of baseline versus 105% in controls, at 12 weeks after transplantation, $p<0.05$, student t-test).

Figure 24:
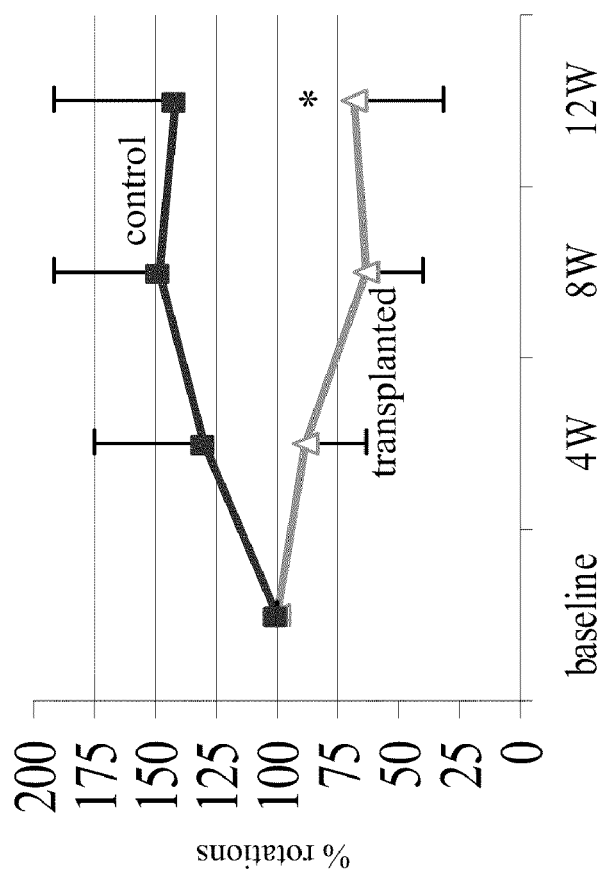

FIG. 24 shows rotational behavior in response to amphetamine. The number of amphetamine-induced rotations was significantly lower in neural sphere-transplanted animals (n=11) compared to sham operated control animals (n=10) ($P<0.004$, student t-test).

Figure 25:
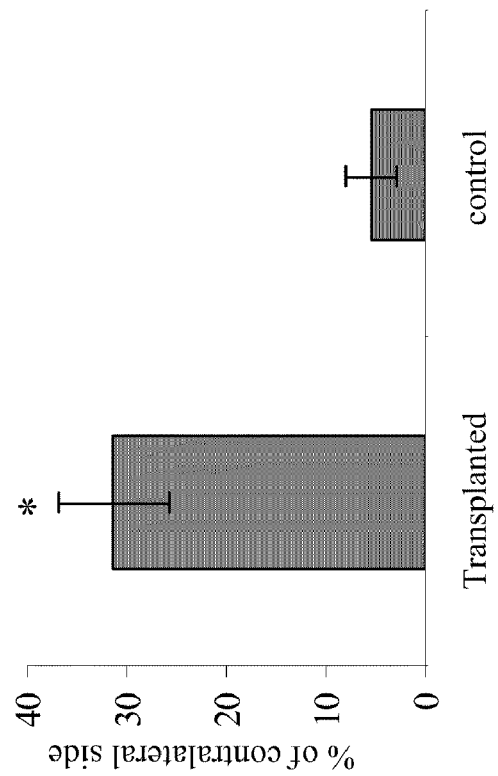

FIG. 25 shows the results of non-pharmacological behavioral evaluation of hES cell-transplanted rats. In both stepping adjustments and forelimb placing non-pharmacological tests there is a significant increase in mobility after stem cell therapy ($p<0.003$, student t test).

Figure 26:
Figure 26:
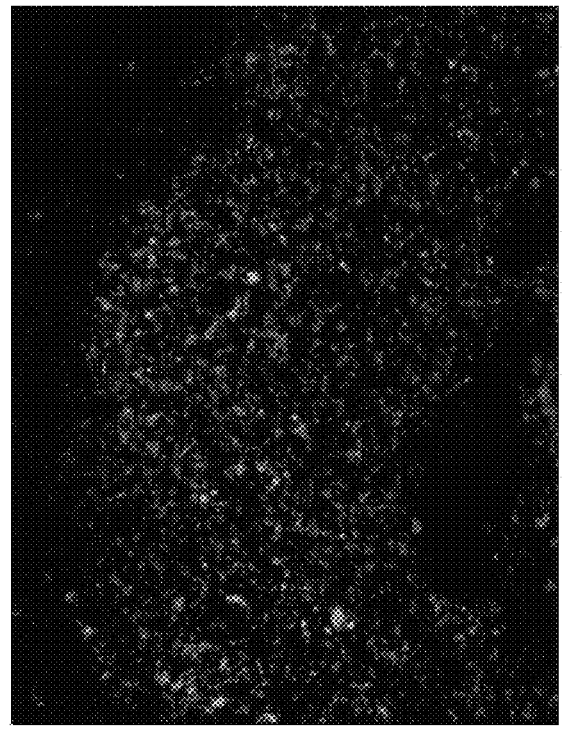

FIG. 26 shows fluorescent images of a trail of human cells, identified by a human specific anti-mitochondrial antibody along the transplantation tract in the Parkinsonian rat striatum, at 24 hour post transplantation (A) and 1 month post transplantation (B). Arrows indicate areas of recipient striatum, near the transplantation tract, without anti-mitochondria+ cells.

Figure 27:
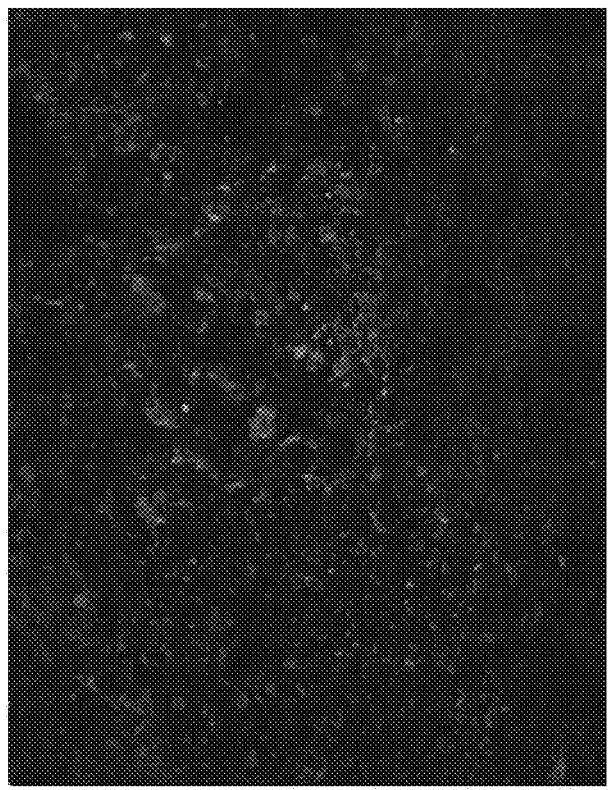
Figure 27:

FIG. 27 shows fluorescent images of the stratum and the injection tracts after immuno-staining for the neural progenitor marker nestin. Many of the transplanted human cells are in a progenitor state, as indicated by expression of the intermediate filament protein nestin.

Figure 28:
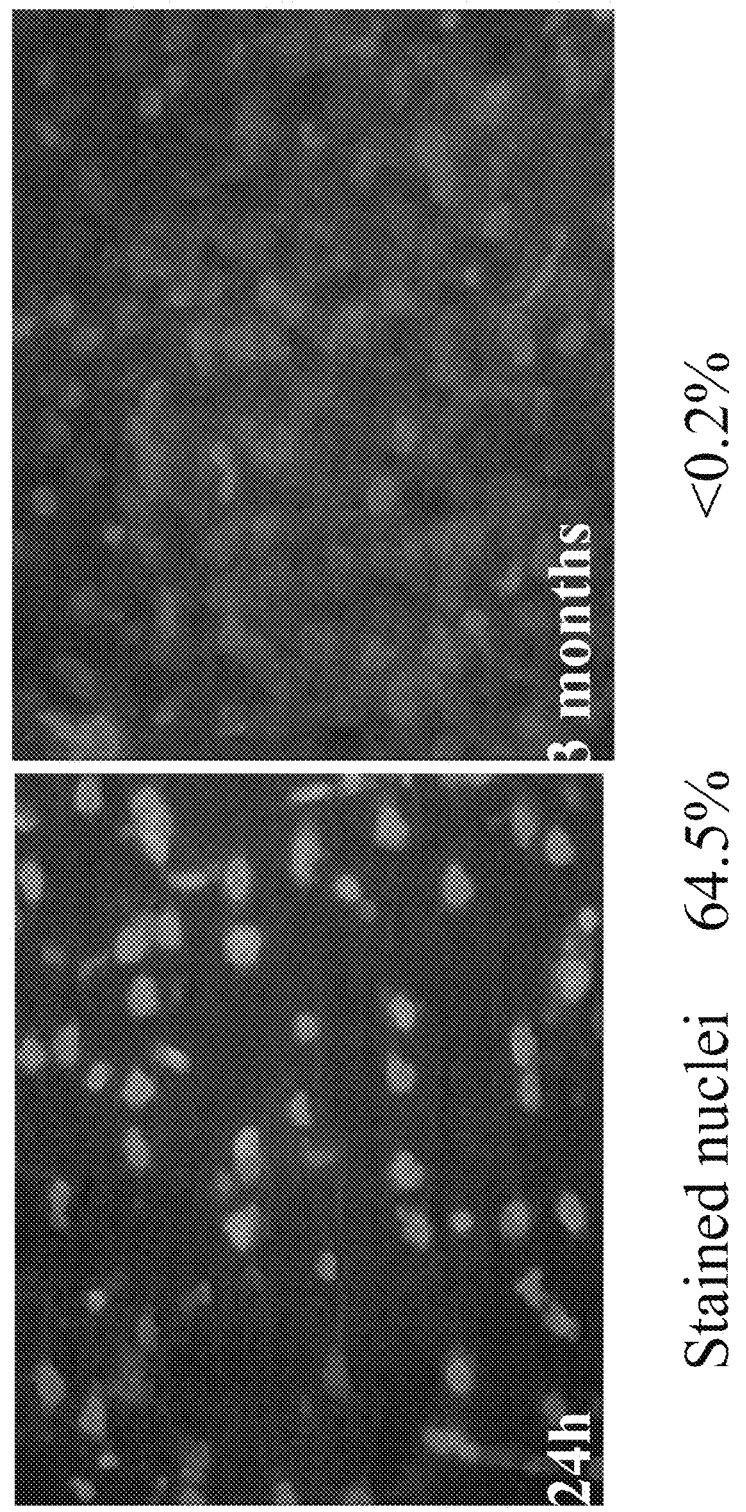

FIG. 28 shows anti PCNA immunostaining of cells within the neural progenitor grafts. At 24 hours after transplantation the majority of cells expressed PCNA (red), while sporadic expression was observed after 12 weeks. Nuclei were stained with DAPI (blue).

Figure 29:
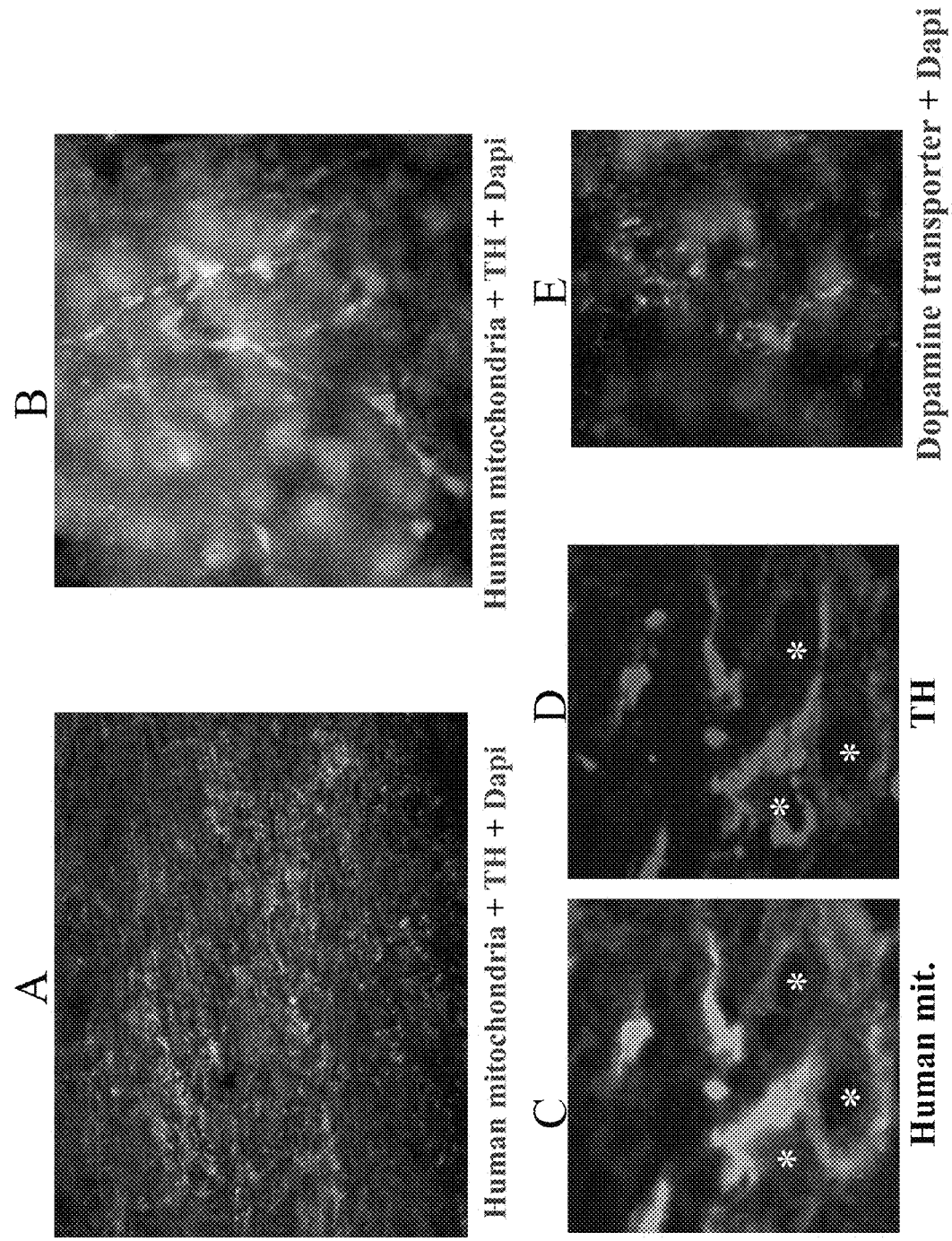

FIG. 29 shows fluorescent images of transplanted human cells expressing TH and DAT. (A-D) Double immuno-fluorescent staining demonstrating TH+ cells (red) that are immunoreactive with the anti-human specific mitochondria antibodies (green) within the graft of human neural cells 3 months after transplantation. (A) Low magnification image demonstrating TH+ cells predominantly in the edges of the trail of engrafted cells. (B) High magnification image of the TH+ cells within the graft (nuclei are counterstained with DAPI ((blue). (C-D) Confocal microscopy images of single cells that are co-expressing human mitochondrial antigen (C) and TH (D, nuclei are indicated by asterisks). Cells immunoreactive with anti-human DAT (green), within the lesioned striatum, are demonstrated in (E) (nuclei are counterstained with DAPI (blue)).

Figure 30:
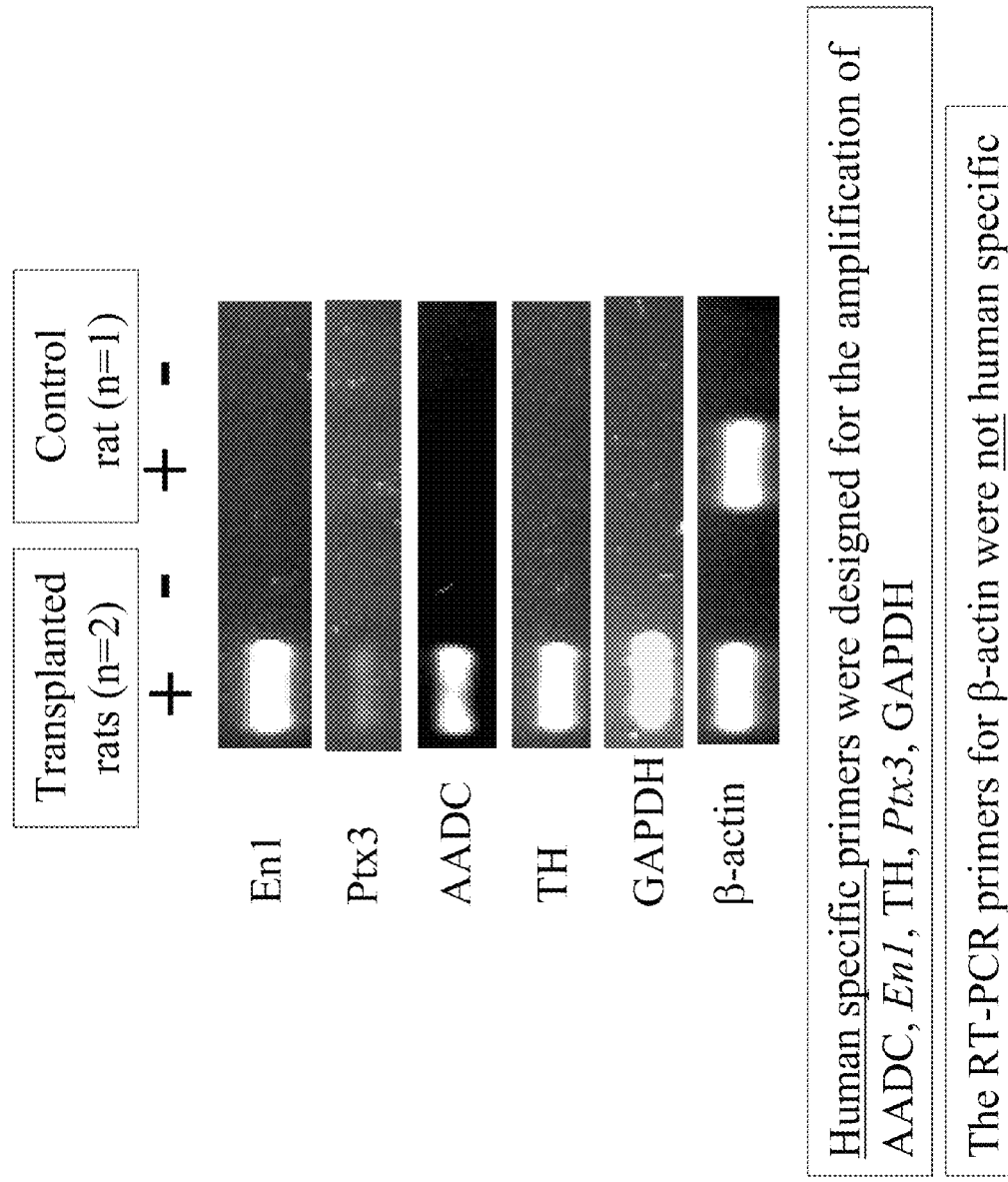

FIG. 30 shows RT-PCR analysis of expression of human specific midbrain and dopamine neuron markers within brain samples from the area of the graft. The human specific transcripts were expressed in stem cell transplanted animals (n=2) while they were not detected in a control vehicle transplanted animal.

Figure 31:
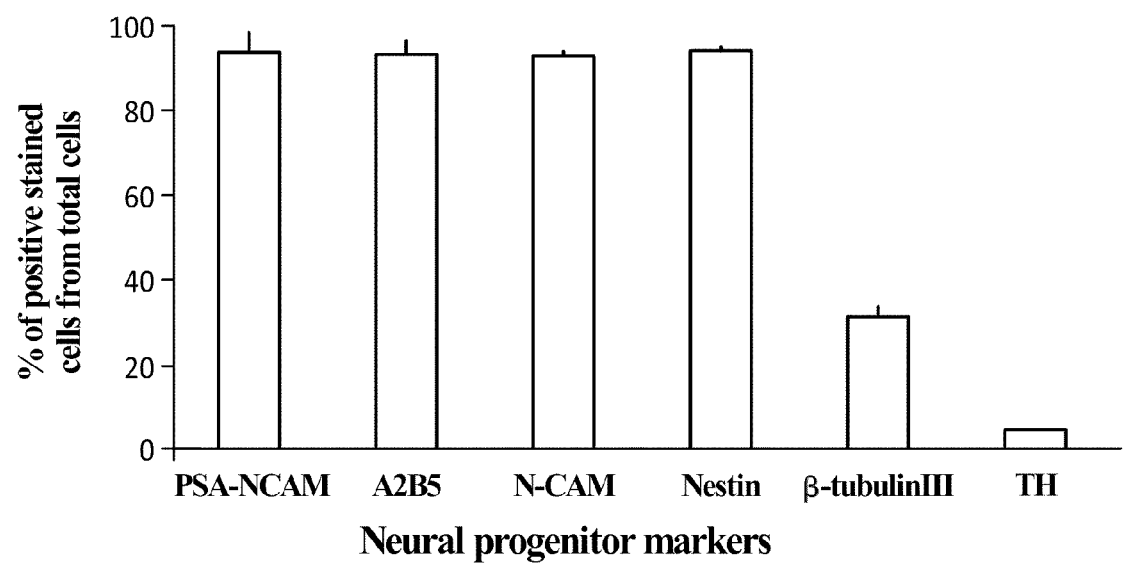

FIG. 31 shows the derivation and characterization of spheres. Dark field stereo-microscope images of an undifferentiated hES cell colony one week after passage (A), noggin treated colony at two weeks after passage (B), and hES cell derived spheres (C). Indirect immunofluorescence staining of the progenitor cells, 12 hours after disaggregating of spheres and plating on adhesive substrate, for PSA-NCAM (D), A2B5 (E), N-CAM (F), and nestin (G), demonstrated that >90% of the progenitors within the spheres expressed markers of neural progenitors (J). Following spontaneous differentiation, 30% of the progenitors differentiated into neurons and were immunoreactive with β-tubulin III (J, H and I (red)). Double immunolabeling showed that 0.5% and 1% of the cells co-expressed β-tubulin III (red) and TH (green, H) or serotonin (green, I).

Figure 32:
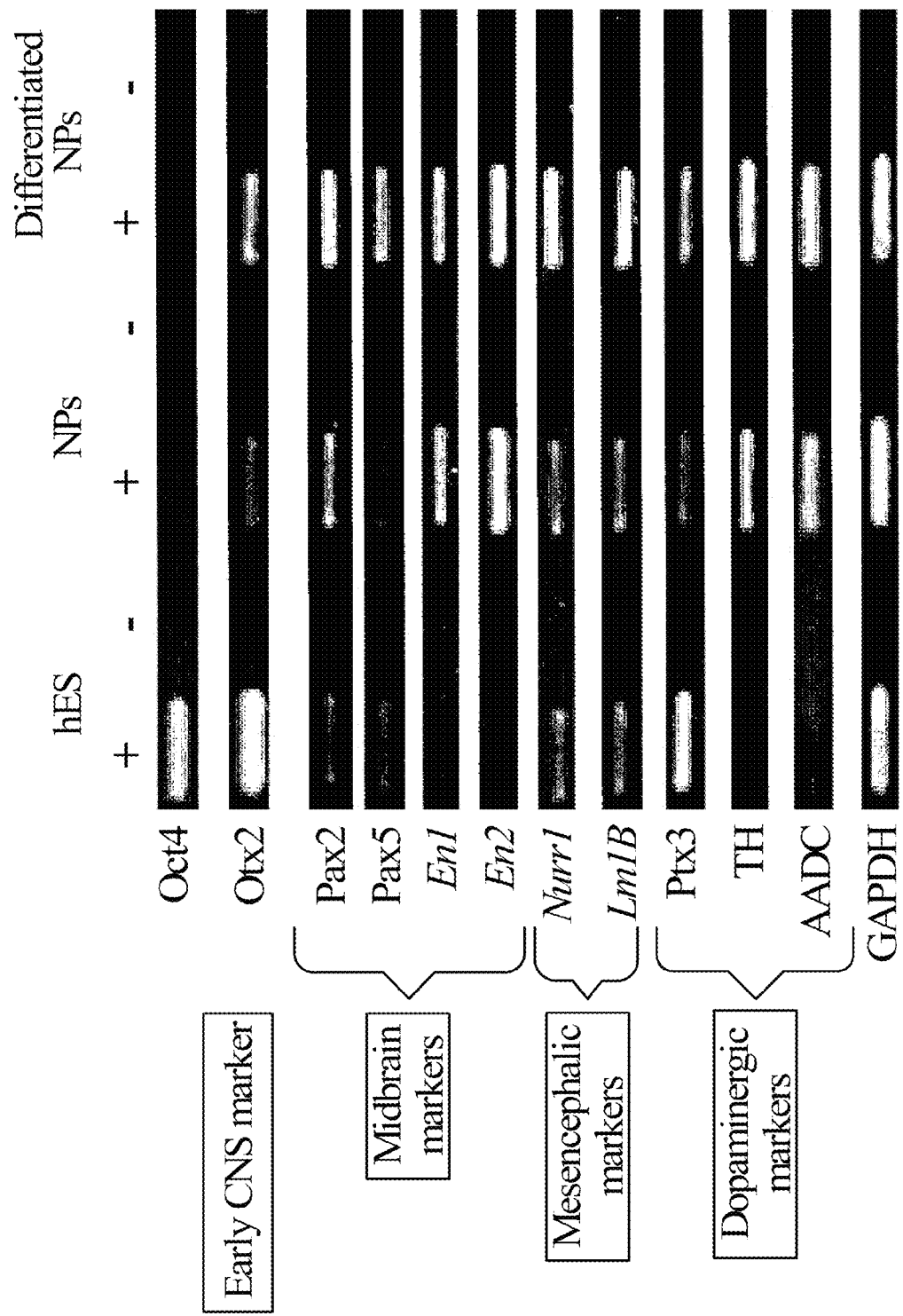

FIG. 32 shows human ES cell-derived NPs express key regulatory genes of midbrain development. Semi-quantitative RT-PCR analysis demonstrated the expression of transcripts of key regulatory genes in midbrain and dopaminergic neurons development as well as markers of dopaminergic neurons within cultures of both undifferentiated and differentiated NPs. Transcripts of OCT4, which is a marker of undifferentiated hES cells were not expressed by the NPs. The symbols + and − indicate whether the PCR reaction was done with or without the addition of reverse transcriptase.

Figure 33:
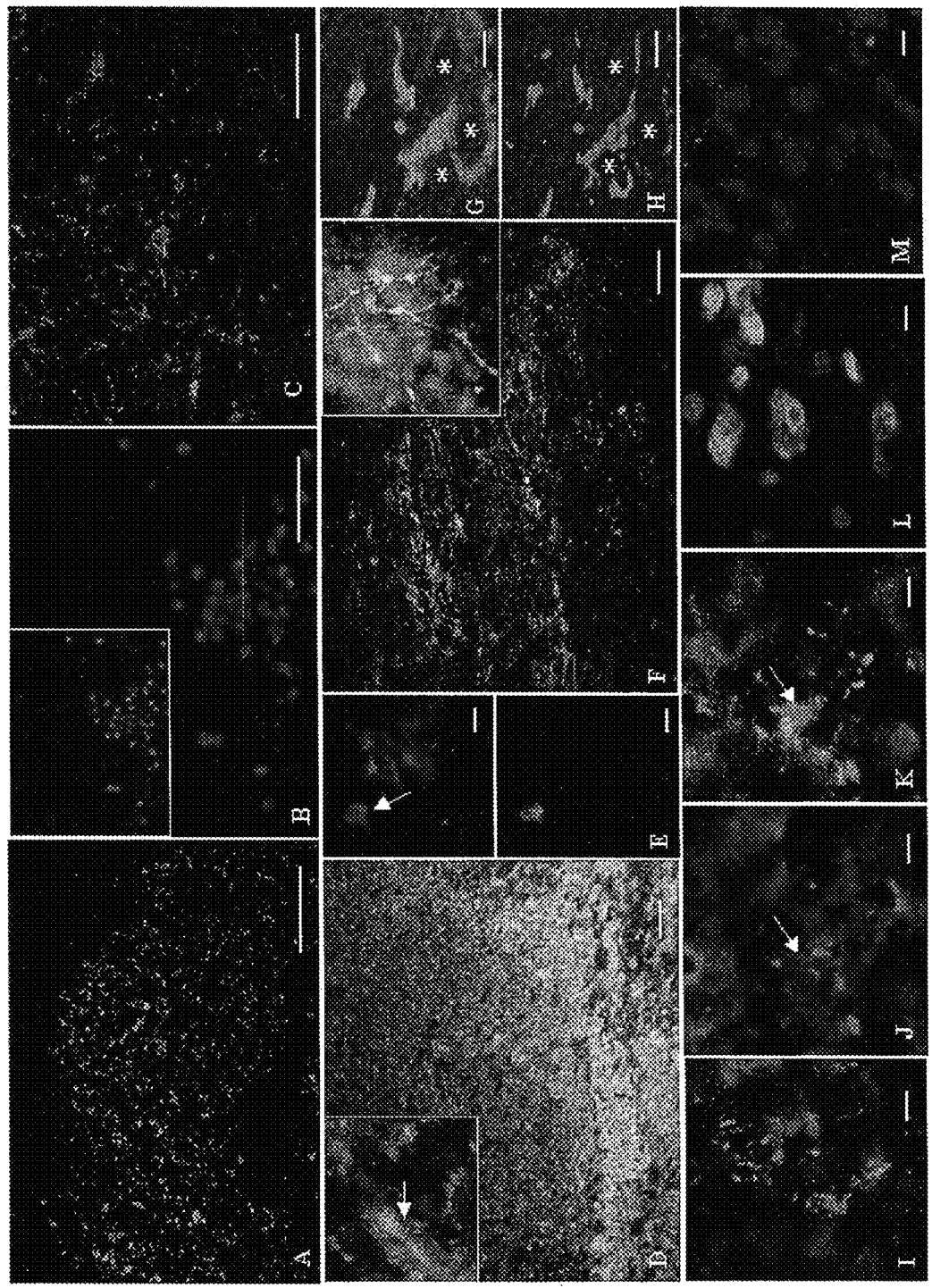

FIG. 33 shows immunohistochemical characterization of transplanted hES-derived neural cells in the brain. Transplanted cells were identified by human-specific antibodies. Staining with human specific anti-mitochondria antibody (A, green) showed the linear graft within the striatum. The human origin of the graft was confirmed by staining with a human-specific anti ribonuclear protein antibody (B, red), that was localized to the cell nuclei (insert, counterstain with Dapi in blue). At 24 hr post transplantation there was high expression of nestin in the graft (C). At 12 weeks post transplantation there were graft-derived neurons in the rat brains, as indicated by double stainings for human specific markers and neuronal markers. Low power field of slides double stained with human mitochondria (D, green) and neurofilament (D, red) showed that the majority of transplant did not stain with the neuronal marker. There were some neurofilament+ human cells (D, insert), especially near the interface with the rat brain tissue. Also, there were human RNP+ cells (E, red) that co-labelled with the neuronal marker NeuN+ (E, green). The generation of dopaminergic neurons by the graft was indicated by the presence of TH+ fibers (F, red) within the human mitochondria+ graft (F, green; insert as high power field). Con-focal microscopy confirmed the presence of human mitochondria+ cells (G) co-staining for TH (H). Generation of dopaminergic neurons was confirmed by staining with antibodies directed against human dopamine transporter (I). Also, there were human mitochondria+ cells (J) that co-labelled with V-MAT (K). At 24 hours post transplantation the majority of transplanted cells expressed the proliferative marker PCNA (L, in red over a blue Dapi counterstain). At 12 weeks almost no PCNA+ cells were found (M, blue dapi counterstain without red PCNA stain). Space bars: A-D, F, 50 µm; E, G-M, 10 µm.

Figure 34:
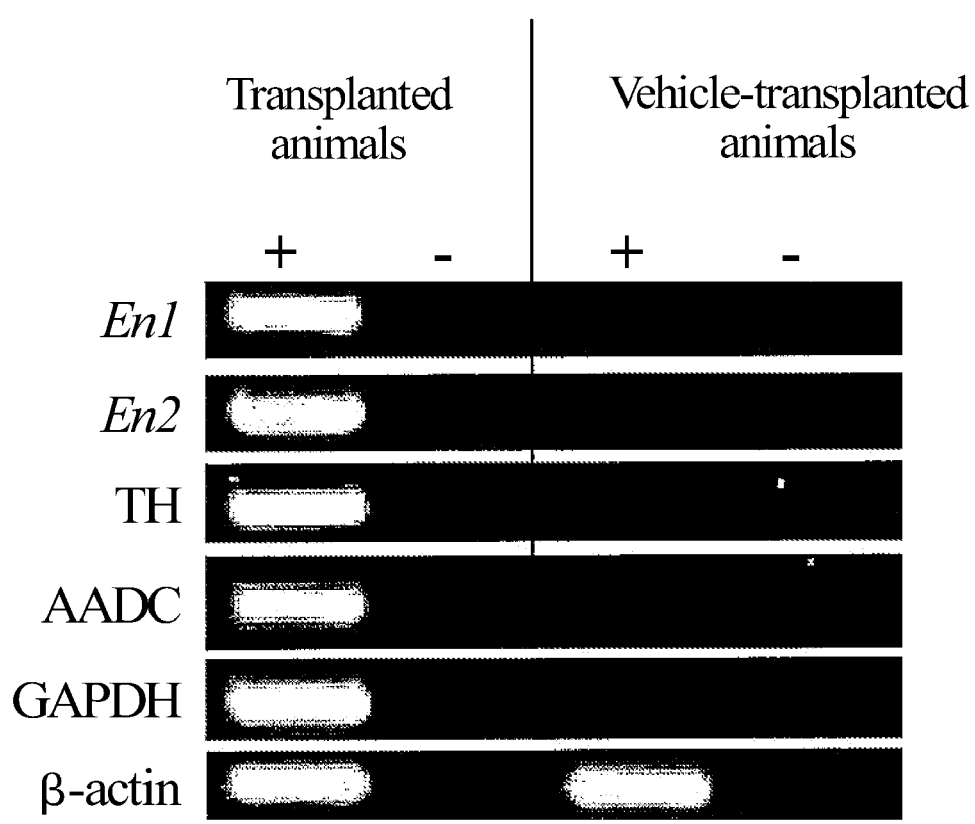

FIG. 34 shows RT-PCR analysis of striata samples from sphere and vehicle grafted animals for the expression of human-specific transcripts of midbrain and dopaminergic neuron markers. The human-specific transcripts were expressed only by animals (n=3 animals) that received hES-derived NPs and were not detected in animals that received sham operation (n=2 animals). Human-specific primers were used to detect transcripts of En1, En2, TH, AADC and GAPDH. The β-actin primers were not human specific. The symbols + and – indicate whether the PCR reaction was done with or without the addition of reverse transcriptase.

FIG. 35 shows transplantation of hES cell-derived neural spheres improves motor function in Parkinsonian rats. The number of d-amphetamine or apomorphine-induced rotations was calculated individually for each rat as percentage of its performance at baseline. For each time point the value represents the mean±SE percent rotations. Rotational behavior that was induced by d-amphetamine (A) and apomorphine (B) decreased significantly in transplanted animals as compared to baseline and to control rats. *$p<0.05$ as compared to baseline and to controls for the pharmacological tests and to the control group for the non-pharmacological tests. Stepping (C, p=0.0012) and placing (D, p=0.0003) also improved significantly in transplanted rats as compared to controls.

DESCRIPTION OF THE INVENTION

In a first aspect of the present invention there is provided a method of directing the fate of human embryonic stem cells towards neural progenitor cells in vitro said method including the steps of:

culturing undifferentiated human ES cells in a defined serum free medium that contains FGF-2 and an antagonist of bone morphogenic proteins (BMP).

In this method, the differentiation of human ES cells is directed into a neural progenitor and differentiation towards other lineages is substantially eliminated. These neural progenitors are not committed at this stage and have the potential to become committed if placed under conditions to induce commitment.

The direction of the differentiation is influenced by the use of the defined serum free media in particular by the presence of FGF-2 and the BMP antagonist. The present invention provides a method of inducing neural progenitor cells from undifferentiated hES cells such that the process that directs neural progenitor cells is augmented toward a neural lineage whereas other lineages are eliminated or less prominent.

Preferably the BMP antagonist is selected from the group including a direct antagonist such as fetuin, noggin, chordin, gremlin, follistatin, Cerberus, amnionless, DAN or the ectodomain of BMRIA (a BMP receptor protein), or ligand binding domains from other BMP receptors. Preferably the BMP antagonist is noggin.

As previously described in the applicants own application PCT/AU01/00735, noggin used in combination with hES stem cells produces a neural progenitor culture. However, the culture is a mixture of neural progenitors and other cell types. This aspect of the present invention refines the differentiation to neural progenitors and neural cell types by the use of defined medium conditions which preferably includes the use of FGF-2 with or without noggin.

In another aspect of the present invention there is provided a cell culture comprising neural progenitor cells differentiated from hES cells and wherein the neural progenitors are non-committed to a neural fate. These cultures have the potential to commit to a neural fate.

In another aspect of the present invention, there is provided an isolated neural progenitor cell differentiated from a hES cell and wherein said neural progenitor is not committed to a neural fate. This cell type has the potential to commit to a neural fate.

The neural progenitor cells prepared by this process may be non-committed neural progenitors that are not committed to any particular type of neural cell such as but not limited to neuronal and glial cell types. These cells may be used, as described below and induced to commit to a neural fate and neuronal cell type preferably including a midbrain cell type. Preferably these cells have a potential to commit to a neural fate.

The characteristics and phenotype of cells following differentiation and propagation in culture may be analyzed for the expression of the early neural markers such as, but not limited to nestin, A2B5, N-CAM, PSA-NCAM and β-tubulin III. The analysis may be conducted at a suitable time to monitor the progression of the cells through the differentiation process. The cells may be analyzed after 3 to 6 weeks of culture in NPM supplemented with FGF2.

The percentage of cells expressing early neural markers increases over time, preferably over three weeks in culture in NPM+FGF2 in comparison to KO medium. Noggin treatment further significantly increases the percentage of cells expressing the neural markers. Preferably the early neural markers including nestin, PSA-NCAM, A2B5 and NCAM are increased. Preferably at least 75% of the cells in any culture expresses the early neural cell markers after culture with an antagonist of bone morphogenic proteins (BMP). Preferably the antagonist of bone morphogenic proteins (BMP) is noggin. Preferably, at least 95 to 100% of the cells show an increase in expression of the neural markers.

More preferably, A2B5 expression is increased to at least about 95% of the cells in culture; and NCAM expression is increased to at least about 73% of the cells in culture, more preferably the expression is increased to at least about 90%. After an additional 3 weeks of culture in NPM+FGF2 the percentage of cells expressing most of the neural markers may stabilize. The major effect of an additional 3 week culture period may increase the percentage of cells expressing NCAM in the noggin treated clumps.

These cells also show a reduction in the expression of non-neural markers such as but not limited to the endodermal marker alpha-fetal protein, the endodermal marker HNF3α or the epidermal marker keratin-14. Other markers showing reduction in expression include laminin and low molecular weight cytokeratin; muscle actin, smooth muscle actin and desmin At the RNA level, RT-PCR analysis may be used to confirm that in the noggin treated clumps the expression of the endodermal marker alpha-fetal protein, the endodermal marker HNF3α or the epidermal marker keratin-14 is reduced. Preferably these markers are significantly reduced at approximately 3 weeks and preferably undetectable at 6 weeks.

The cells may also be distinguished by their overexpression of Nurr-1. More preferably the cells co-express Nurr-1 and TH. The expression of Nurr-1 may be maintained during differentiation into neurons particularly those co-expressing Nurr-1 and TH.

Preferably, the neural progenitors are obtained from undifferentiated hES cells that are directed to differentiate into neural cells by culture in suspension preferably as clumps in defined serum free culture medium preferably neural progenitor media (NPM) in the absence of feeders. The NPM may be supplemented with FGF-2, with/without EGF and/or LIF.

The NPM may contain DMEM/F12 (1:1), B27 supplementation (1:50), glutamine 2 mM, penicillin 50 u/ml and streptomycin 50 µg/ml (Gibco), and supplemented with 20 ng/ml fibroblast growth factor 2 (FGF2) with or without 20 ng/ml human recombinant epidermal growth factor (EGF), and 10 ng/ml human recombinant LIF (R & D Systems, Inc., Minneapolis, Minn.).

The cells may be cultured in suspension and may be exposed to noggin in the range of 350-700 ng/ml.

FGF-2 is used to promote proliferation and prevent the differentiation of the undifferentiated non-committed hES cell derived neural progenitors in the presence of noggin. A suitable FGF-2 concentration is approximately 20 ng/ml.

In another aspect of the present invention, there is provided a cultured undifferentiated ES cell which is committed to differentiate to a neural progenitor.

In another aspect of the present invention there is provided a method of directing neural fate in a human embryonic stem (hES) cell in vitro said method comprising the steps of:
  obtaining a neural progenitor cell from a hES cell culture; and
  culturing the neural progenitor cell in the presence of a neural fate inducer selected from the group including at least one of Fibroblast Growth Factor (FGF), Sonic Hedgehog Protein (SHH), cAMP inducers, Protein Kinase C (PKC) inducers, dopamine and ascorbic acid (AA) or any combination thereof.

The present method provides for a controlled differentiation of neural progenitors, preferably towards a transplantable neural cell that establishes in a predetermined region of the body. Highly enriched preparations of these cells may be obtained by the methods described herein. The newly derived cells have improved transplantability and are more potent in vivo. This improved potency translates to improved survival and/or function of the differentiated cells upon transplantation.

The method describes "directing neural fate". This term as used herein means to guide the differentiation and development of neural progenitors preferably toward a midbrain fate, or toward neuronal cell types, preferably neurons that show characteristics typical of midbrain neurons. The method may be used to generate any neural progenitor or neuronal subtype including but not limited to hES derived GABAergic, glutamergic, cholinergic, motor neurons, dopaminergic and serotonergic neurons. The method preferably directs a midbrain neural fate to the neural progenitors derived from hES cells.

More preferably the neural cell is a neural progenitor cell committed to a midbrain fate, tyrosine-hydroxylase (TH) positive (TH$^+$) cell or dopaminergic cell.

Throughout the description and claims of this specification, the word "comprise" and variations of the word, such as "comprising" and "comprises", is not intended to exclude other additives, components, integers or steps.

The neural progenitor cells may be obtained by any means that provides these cells from a culture of hES cells preferably an undifferentiated culture of hES cells. The hES cells may be spontaneously differentiated or induced to differentiate preferably as described in the applicant's own applications namely PCT/AU01/00278 and PCT/AU01/00735, the contents of which are incorporated herein.

Preferably, the neural progenitor cells are non-committed hES cell derived neural progenitors that have not been committed to any particular neural cell type or fate.

In a further preferred embodiment, the neural progenitor cells are obtained herein from a hES cell culture treated with noggin or other inhibitors or antagonists of bone morphogenic proteins (BMP). The use of noggin directs the undifferentiated hES cell within colonies that are cultured on feeders into areas comprised of small fight cells and areas with neural rosettes. Dissection of these areas and transferal into defined serum free culture conditions may produce characteristic preparations of proliferating neural progenitors. The serum free culture conditions may include media which may be neural progenitor growth medium (NPM) supplemented with fibroblast growth factor (FGF) preferably FGF-2, with/without epidermal growth factor (EGF) and/or leukaemia inhibitory factor (LIF) A typical NPM may contain DMEM/F12 (1:1), B27 supplementation (1:50), glutamine 2 mM, penicillin 50 u/ml and streptomycin 50 µg/ml (Gibco), and supplemented with 20 ng/ml human recombinant epidermal growth factor (EGF), and 20 ng/ml fibroblast growth factor 2 (FGF2) (R & D Systems, Inc., Minneapolis, Minn.).

In a further preferred embodiment the neural progenitors are obtained from undifferentiated hES cells that are directed to differentiate into neural cells by culture in suspension preferably as clumps in defined serum free culture medium preferably NPM in the absence of feeders. The NPM may be supplemented with FGF-2, with/without EGF and/or LIF.

In an even further preferred embodiment the undifferentiated hES cells that are cultured in suspension as above, are also treated with noggin. Noggin may be used in a range of 350-700 ng/ml. The addition of noggin further promotes the differentiation towards the neural lineage and into neural progenitors, while it reduces the differentiation into non-neural lineages. These cultures provide neurospheres comprising neural progenitors that may be used to differentiate toward a neural cell line with a committed neural fate when cultured in the presence of the neural fate inducers.

During the culturing of the hES cells and differentiation towards neural progenitors, these cells may be cultured in the presence of FGF, with/without EGF and/or LIF. Preferably the FGF is FGF-2. A suitable concentration of FGF-2 is approximately 20 ng/ml. EGF may be added in the form of naturally produced or recombinantly produced EGF, more preferably human EGF is more suitable for hES cells. A suitable concentration for EGF is approximately 20 ng/ml. LIF may be added to promote proliferation of neural progenitors during induction of differentiation when noggin is presented to the cells simultaneously. Under these conditions NPM may be supplemented with FGF-2 and LIF. LIF is preferably a human LIF and suitably used in a concentration of approximately 10 ng/ml.

In another aspect of the invention there is provided a method to block differentiation of hES cells towards non-neural lineages. Exposure of hES cells cultured in NPM to noggin blocks the differentiation to non-neural lineages, preferably mesoderm, endoderm (probably extraembryonic) and epidermal lineages.

Additional culture of the spheres in NPM+FGF2 without noggin further eliminates non neural cells, preferably endodermal (probably extraembryonic) epidermal and mesodermal cells. This is evidenced by the reduction of the expression of non-neural markers.

In another aspect of the present invention there is provided a method of directing neural fate in a human embryonic stem (hES) cell in vitro said method comprising the steps of:

obtaining a neural progenitor cell from a hES cell culture; and inducing an overexpression of Nurr 1 and/or Lmx1b in the hES cell.

Without being limited by theory, applicants propose that the overexpression of the Nurr1 and/or Lmx1b gene can direct the differentiation of hES cells toward a neural fate and DA neurons. Applicants have shown that the hES cells that have differentiated toward the neural fate show an over-expression of the Nurr1 gene. The expression is maintained during differentiation into neurons that co-express Nurr1 and TH.

The Nurr 1 and/or Lmx 1b expression may be induced by any methods available to the skilled addressee. Preferably, the gene(s) are introduced by genetic modification. The gene(s) may be introduced by a suitable vector under the influence of an inducer such that when differentiation is to be effected, expression of the gene may be induced by introduction of the inducer to the cell culture. Preferably the cells are genetically modified using the lentiviral vector transduction system as described in PCT/AU02/0175.

In another aspect of the invention, there is provided a method of enhancing the survival of transplanted DA neurons said method comprising obtaining a neural progenitor cell from a hES cell culture;

inducing an expression of GDNF and/or BDNF in the neural progenitor cell or a cell differentiated from the neural progenitor.

Without being limited by theory, Applicants propose that a forced expression of GDNF and/or BDNF by the transplanted hES cells or their neural progeny may enhance the survival of transplanted DA neurones. Preferably the expression is an over-expression above a level that is naturally present.

The neural progenitors may be according to the neural progenitors described above. They may be genetically modified to include vectors that express GDNF and/or BDNF and which may be under the influence of an inducer that can be switched on at an appropriate time to enhance the survival of the transplanted cell. The timing may coincide with a period that improves the survival of the cell. Preferably, the GDNF and/or BDNF is induced when the cells are transplanted. However, these factors may be induced during the differentiation stage to enhance their survival.

Differentiated and transplantable hES cells of the present invention may be modified to express Nurr1 and/or Lmx 1b along with GDNF and/or BDNF to provide enhanced survival of transplanted hES cells.

Preferably, the cells differentiate to glial cells. Preferentially, the cells are transplanted as hES cells capable of differentiation and the differentiation is induced in vivo in the presence of the induced genes Nurr1 and/or Lmx 1b. Further induction of the survival factors GDNF and/or BDNF may also be present in vivo.

In yet another aspect of the present invention there is provided a genetically modified hES cell that has been prepared by the methods described above. Preferably, the cell can differentiate to a glial cell and can preferably be directed to differentiate upon forced expression of the Nurr1 and/or Lmx 1b gene and/or the GDNF and/or BDNF survival factors.

The present invention also contemplates transgenic animals having the modified genes.

In a further embodiment, the invention includes methods of treating neural conditions using the genetically modified hES cell, said method comprising transplanting the genetically modified hES cell and inducing the expression of the Nurr1 and/or Lmx 1b gene and/or the GDNF and/or BDNF survival factors.

The neural progenitor cells are cultured in the presence of neural fate inducers to induce them to differentiate toward a specific neural progenitor cell preferably committed to a midbrain fate or a neural or neuronal cell type preferably with a committed midbrain fate.

The term "neural fate inducer" is any substance that can direct the neural progenitor toward a neural cell type such as, but not limited to a progenitor of a specific neural fate such as but not limited to midbrain fate, midbrain neurons and any neuronal cell type selected from the group including hES derived GABAergic, glutamerigic, cholinergic, dopaminergic, serotonergic and motor neurons. The substance(s) also promotes survival of neurons such as to promote growth, function, augment activity of functioning cells, enhance synthesis of neurotransmitter substances, enhance activity of naturally occurring nerve growth promoting factors, prevent degeneration of neurons, induce regrowth whilst directing the cell toward a neural fate and enhancing survival of the differentiated neural cell.

The term "FGF" as used herein may include, but is not limited to, FGF-1, FGF-2, FGF-6, FGF-8, FGF-9, FGF-98 and FGF-17, or any biologically active fragment or mutein thereof. Preferably for the induction of human neurons from hES cells, it is preferable to use FGF-1, FGF-8 or FGF-17 alone or in combination. The FGF may derive from any animal, preferably mammalian, more preferably human. Natural or recombinantly produced FGF, preferably FGF-1, FGF-8 or FGF-17 may be used.

Biologically active variants of FGF are also encompassed by the method of the present invention. Such variants should retain FGF activities, particularly the ability to bind to FGF receptor sites.

FGF activity may be measured using standard FGF bioassays, which are known radioreceptor assays using membranes, a bioassay that measures the ability of the molecule to enhance incorporation of tritiated thymidine, in a dose-dependent manner, into the DNA of cells, and the like. Preferably, the variant has at least the same activity as the native molecule.

The biologically active variants can be FGF analogues or derivatives. The term "analogue" as used herein is an analogue of either FGF or an FGF fragment that includes a native FGF sequence and structure having one or more amino acid substitutions, insertions, or deletions. Analogues having one or more peptoid sequences (peptide mimic sequences) are also included. The term "derivative" as used herein is any suitable modification of FGF, FGF fragments, or their respective analogues, such as glycosylation, phosphorylation, or other additions of foreign moieties, so long as the FGF activity is retained. Methods for making FGF fragments, analogues, and derivatives are available in the art.

In addition to the above described FGFs, the method of the present invention can also employ an active mutein or variant thereof. By the term active mutein, as used in conjunction with an FGF, is meant to include a mutated form of the naturally occurring FGF. FGF muteins or variants will generally have at least 70%, preferably 80%, more preferably 85%, even more preferably 90% to 95% or more, and most preferably 98% or more amino acid sequence identity to the amino acid sequence of the reference FGF molecule. A mutein or variant may, for example, differ by as few as 1 to 10 amino acid residues, such as 6-10, as few as 4, 3, 2 or even 1 amino acid residue providing the FGF activity is maintained.

A new member of the FGF family, FGF 17, was recently discovered (Hoshikawa et al., 1998). Like FGF8 it is predominantly expressed in the developing CNS in the midline region of the forebrain and the midbrain-hindbrain junction.

In addition it is expressed in additional distinct expression domains (Xu et al., 1999, Heikinheimo et al., 1994, Crossley et al., 1995). FGF-8 is expressed earlier then FGF-17, whose expression persists a little longer (Xu et al., 2000). While these factors may have a functional relationship in patterning some areas of the brain, the role of FGF-17 in CNS development or its effect on ES cell differentiation is unknown.

"Sonic Hedgehog Protein" (SHH) refers to any sonic hedgehog protein derived from any animal, and functional fragments thereof.

"cAMP Inducers" as used herein, may be selected from any compound that induces cAMP activity either directly by forskolin or NPA (R(−)-propylnorapomorphine a D2 receptor agonist of PKA, increases cAMP) or indirectly by inhibiting phosphodiesterase by Isobutyl-methoylxanthine (IBMX) or by compounds with IBMX like activity such as cAMP-specific Ro 20-1724, Rolipram, or Etazolate but more preferably selected from the group including Isobutyl-methoylxanthine (IBMX), or forskolin used alone or in combination.

"Protein Kinase C (PKC) Inducers" as used herein may be phorbol myristate acetate or phorobol 12-myristate 13-acetate which is a specific activator of PKC group A ($\alpha,\beta I,\beta II,\chi$) and PKC group B ($\delta,\epsilon,\eta,\theta$) or tumor promoter activity (TPA). However, any substance that induces isozyme specific PKC either directly or indirectly is included in the scope of the present invention.

"Dopamine" as used herein includes naturally or synthetically produced dopamine or any functional equivalent or analogue thereof. "Functional equivalents or analogues" are those compounds that have the same activity as naturally produced dopamine that is produced by the adrenal medulla.

Dopamine, along with epinephrine, norepinephrine, and serotonin, belongs to a chemical family referred to "monoamines". Within the family of monoamines, epinephrine, norepinephrine, and dopamine are derived from the amino acid tyrosine and form a subfamily called the catecholamines. Frequently, tyrosine hydroxylase (TH), the rate-limiting enzyme for the biosynthesis of dopamine, is used as a marker to identify dopaminergic neurons.

In a preferred aspect of the present invention there is provided a method of directing midbrain fate to a hES cell in vitro, said method comprising the steps of:
  obtaining a neural progenitor cell from a hES cell culture; and
  culturing the neural progenitor cell in the presence of a midbrain fate inducer selected from the group including any one of FGF-1, FGF-8, FGF-17, SHH, AA, cAMP inducers, PKC inducers and dopamine or any combination thereof.

The neural progenitor may be presented as clumps or clusters of cells, neurospheres or single cells. Clumps or clusters may comprise any numbers of cells preferably providing the cells can be exposed to the neural fate inducers. However, cells on the outer of the clumps may be induced toward a neural fate. Preferably the clumps or neurospheres comprise up to 3000 cells per clump, more preferably the clumps comprise 2000-3000 cells per clump. The neural progenitors may be presented to the inducers either in suspension or adherent cultures, preferably the cells are adherent to poly-D-lysine and laminin.

The use of the specific midbrain fate inducers causes the differentiation to be directed to midbrain cells rather than neural cells of other brain regions.

The neural cells may be cultured in the presence of FGF-2 with or without EGF and/or LIF. When culturing in the presence of the midbrain fate inducers, FGF-2 and EGF and/or LIF may be removed from the medium so that the progenitors are more readily directed to take a midbrain fate by treatment with the midbrain fate inducers.

FGF selected from the group including FGF-1, FGF-8 and FGF-17 is used as a midbrain fate inducer. These factors are preferably used in combination with other midbrain fate inducers at a concentration of approximately 100-200 ng/ml.

SHH is preferably used in combination with other midbrain inducers at a concentration of about 0.5-1 µg/ml.

cAMP inducers such as IBMX or forskolin may be used at a concentration of about 0.25 mM and 50 µM respectively in combination with other midbrain inducers.

The PKC inducers PMA/TPA may be used in the concentration of 200 nM and dopamine may be used at a concentration of about 20 µM in combination with other midbrain inducers.

It is most preferred that the midbrain fate inducer is a combination of FGF-1, FGF-8, FGF-17, SHH, IBMX, forskolin, PMA/TPA and dopamine. Various other combinations may be useful including the combination of:
(i) FGF-8 and SHH, IBMX, forskolin, PMA/TPA and dopamine; or
(ii) FGF-17 and SHH, IBMX, forskolin, PMA/TPA and dopamine; or
(iii) FGF-1, and IBMX, forskolin, PMA/TPA and dopamine; or
(iv) FGF-8 alone; or
(v) FGF-17 alone; or
(vi) IBMX, forskolin, PMA/TPA, and dopamine.

Preferably, FGF-8 and FGF-1 are used in a concentration of about 200 ng/ml.

In a further preferred embodiment, the method further includes culturing the neural progenitor in the presence of ascorbic acid (AA) or an analogue thereof.

The addition of AA or an analogue thereof to the cells in the presence of the midbrain fate inducers improves the survival of the cells and further directs the differentiation toward TH$^+$ cells. Furthermore, TH production/expression may be increased. AA or an analogue thereof may be added together with or following exposure of the cells to midbrain fate inducers. Addition of AA or an analogue thereof at the time of removal of FGF-2 and EGF may improve TH$^+$ generation. The AA or an analogue thereof is supplemented to the medium, preferably NPM in the presence or absence of FGF-2 and EGF and/or LIF. AA or an analogue thereof may be used at a concentration of approximately 400-800 µM.

AA or an analogue thereof may be used with any one or combination of FGF-1, FGF-8 or FGF-17 with or without other midbrain inducers.

In an even further preferred embodiment, the method further includes culturing the neural progenitor in the presence of NT4 or equivalent thereof such as NT3.

The term "equivalent thereof" as used herein means a sequence or molecule which functions in a similar way but may have deletions, additions or substitutions that do not substantially change the activity or function of the sequence or molecule.

NT4 is a survival factor like AA. If added at the stage of AA addition, the proportion of TH$^+$ neurons can be increased. NT4 may be used at a concentration of about 20 ng/ml.

In yet an even further preferred embodiment, the method includes the further step of:
  culturing the neural progenitor cells on poly-D-lysine and laminin.

This additional step will induce further differentiation into neurons. The neural progenitors, having been exposed to midbrain inducers, AA with or without NT4 may be disaggregated at this stage and plated on poly-D-lysine and laminin. Generally, the concentration of poly-D-lysine is in the range of about 5 to 15 µg/ml preferably 10 µg/ml and laminin is in the range of about 1 to 10 µg/ml, preferably, 4 µg/ml.

The cells may continue to be cultured in NPM supplemented with AA with or without NT4.

Progression of differentiation throughout the process of the method from undifferentiated ES cells to uncommitted neural progenitors, committed neural progenitors, and specific types of differentiated neural cells may be followed by monitoring the expression of marker genes of various cell types or key genes in the development in vivo of undifferentiated ES cells, differentiated cells from various lineages, the CNS, specific areas of the CNS, and various types of differentiated neural cells. The expression of key genes may be monitored at the protein or mRNA level. RT-PCR, semi-quantitative RT-PCR, real time RT-PCR micro and macro arrays or any other method may be used to monitor the expression of mRNA.

Preferably, total RNA is extracted from undifferentiated hES cells; differentiated hES cells; neurospheres at various time points along propagation and following differentiation. RT-PCR is then used to monitor the expression of key genes and markers including: transcriptional markers for undifferentiated hES cells (Oct4); markers of endoderm probably of extra embryonic origin ($\alpha$FP and HNF3$\alpha$); mesoderm marker (CD34); epidermal marker (keratin 14). Early CNS (central nervous system) marker (Otx2); Mesencephalic markers (Pax5, Pax2, wnt1); midbrain markers (Nurr1, Lmx1b, En1. and En2) and markers of the dopaminergic pathway (AADC, TH, Ptx3).

Progression of differentiation throughout the process of the method may be monitored also by physical assessment of morphology (ascertained by the trained eye) or by analysis of marker expression at the protein level. Early expression neural markers such as but not limited to N-CAM, A2B5, PSA-NCAM and nestin can help to assess progression toward neural progenitors. The markers $\beta$-tubulin III, light chain neuro filaments are expressed by early neurons while heavy chain neurofilaments, MAP-2ab, synaptophysin and neurotransmitors are expressed by mature neurons.

Additionally, measurement of $TH^+$ may serve as a marker to identify dopaminergic neurons. Other markers of dopaminergic neurons are aromatic-L-amino acid decarboxylase (AADC) and dopamine transporter (DAT). Dopaminergic neurons as opposed to norepinephric neurons lack the expression of dopamine $\beta$ hydroxylase (DBH). The production and secretion of dopamine (measured by RP-HPLC) is a definitive marker of dopaminergic neurons. Electrophysiological methods may be further used to characterize the maturity and function of TH+ neurons.

In another aspect of the present invention there is provided a cell culture comprising neural progenitors with a committed fate, preferably a midbrain fate. Preferably the neural progenitors are in aggregates or sphere structures. More preferably when these aggregates are induced to differentiate at least 30% of them give rise to a significant number (>50) of TH+ neurons. The proportion of clumps containing TH+ cells may increase to at least 60% when the midbrain fate of the progenitors is enhanced by midbrain inducers as detailed above.

In a preferred aspect the cell culture of committed neural progenitors capable of specific neural fate are generated from undifferentiated hES derived neural progenitor ells cultured under defined culture conditions of defined media.

The neural progenitors that are differentiated from undifferentiated hES cells following noggin treatment and specific culture conditions have the potential to give rise to multiple lineages but they also have the potential to further differentiate to cells having a neural fate, preferably a midbrain fate.

The present invention generates cultures of neural progenitors and isolated neural progenitors with a neural fate, preferably a midbrain fate. The neural fate inducers (except the survival factor AA) are removed from the medium at the time of differentiation from progenitors into neurons and still TH+ neurons are obtained. This indicates that the progenitors are committed to a midbrain fate and will give rise to TH+ neurons in the absence of neural fate or midbrain fate inducers. Without being limited by theory, it is considered that the production of progenitors committed to a midbrain fate is important since transplantation of committed progenitors may be more effective than differentiated neurons since they may have a better survival potential after transplantation and may have a higher potential to integrate and interact with the host brain. The committed progenitors may be identified by their potential to differentiate into TH+ neurons without any treatment with midbrain inducers.

In another preferred aspect of the present invention there is provided a cell culture comprising clumps of differentiated hES cells and wherein at least 30% of the clumps include a significant number (>50) of neurons with a midbrain fate. The proportion of clumps containing TH+ cells may increase to at least 60%.

In another preferred aspect of the invention there is provided a cell culture comprising clumps of differentiated hES cells and wherein at least 30% of the neurons ($\beta$-tubulin III+ cells) are expressing TH. The proportion of neurons expressing TH may increase to at least 60%.

In a further preferred aspect there is provided a cell culture comprising a population of differentiated hES cells wherein the population is substantially neural progenitors having a midbrain fate. More preferably, the population comprises neural progenitors that can give rise upon differentiation to neurons that are $TH^+$ or dopaminergic. Most preferably, the cell culture is prepared by the methods described herein.

In an even further preferred aspect there is provided a cell culture comprising a population of differentiated hES cells wherein the population is substantially neurons having a midbrain fate. More preferably, the population comprises neurons that are $TH^+$ or dopaminergic. Most preferably, the cell culture is prepared by the methods described herein.

Preferably, the neural progenitors with a midbrain fate induced by exposure to midbrain fate inducers give rise to $TH^+$ neurons or dopaminergic neurons. Preferably the cells have improved transplant ability and function in-vivo wherein improvement is over differentiated hES cells that have differentiated spontaneously into non-committed neural progenitor cells.

Preferably, the cells are functional in vivo and more preferably the cells are functional in vivo and have the ability to transplant and repopulate by proliferation and differentiation.

By "functional" it is meant to include that the neurons can show nerve growth, be active by enhancing neurotransmitters and by synaptically active and influence motor, sensor cognitive autonomous or any other type of behavior that results from nerve function.

In another aspect of the present invention, there is provided an isolated human neural progenitor cell having a committed neural fate, more preferably a committed midbrain fate. Preferably the cell can differentiate into a $TH^+$ neuron or a dopaminergic neuron. Most preferably, the cell is prepared by methods described herein and isolated from a culture of differentiated hES cells that have been induced to differentiate toward a midbrain fate by the use of midbrain fate inducers described herein.

In another aspect of the present invention, there is provided an isolated human neuronal cell having a committed neural fate, more preferably a committed midbrain fate. Preferably the cell is TH⁺ neuron or a dopaminergic neuron. Most preferably, the cell is prepared by methods described herein and isolated from a culture of differentiated hES cells that have been induced to differentiate toward a midbrain fate by the use of midbrain fate inducers described herein.

In another aspect of the present invention there is provided a human neural fate inducer for inducing neural fate in a cultured hES cell and blocking non-neural lineages. The inducer is selected from the group of BMP antagonists including but not limited to fetuin, noggin, chordin, gremlin, follistatin, Cerberus, amnionless, DAN or the ectodomain of BMRIA (a BMP receptor protein), or ligand binding domains from other BMP receptors more preferably the inducer is noggin.

In another aspect of the present invention there is provided a human neural fate inducer composition for inducing neural fate in a cultured hES cell, said composition comprising a neural fate inducer selected from the group including Fibroblast Growth Factor (FGF), ascorbic acid (AA), Sonic Hedgehog Protein (SHH), cAMP inducers, Protein Kinase C (PKC) inducers and dopamine or any combination thereof.

Preferably the composition is a human midbrain neural fate inducer, more preferably the composition is a human midbrain neural progenitor inducer more preferably a TH⁺ cell inducer, and even more preferably a dopamine producing neuron inducer.

Preferably the FGF is selected from the group including FGF-1, FGF-8 or FGF-17.

Preferably the "cAMP Inducers" are selected from any compound that induces cAMP activity either directly by forskolin or NPA (R(−)-propylnorapomorphine, a D2 receptor agonist of PKA, increases cAMP) or indirectly by inhibiting phosphodiesterase IBMX like activity by cAMP-specific Ro 20-1724, Rolipram, Etazolate but more preferably selected from the group including Isobutyl-methoylxanthine (IBMX), or forskolin used alone or in combination.

The "Protein Kinase C (PKC) Inducers" may be phorbol myristale acetate (PMA Phorobol 12-myristate 13-acetate is a specific activator of PKC group A $\alpha,\beta I,\beta II,\chi$) and PKC group B ($\delta,\epsilon,\eta,\theta$)) or tumor promoter activity. However, any substance that induces isozyme specific PKC either directly or indirectly is included in the scope of the present invention.

"Dopamine" may include naturally or synthetically produced dopamine or any functional equivalent or analogue thereof.

In yet another aspect of the present invention, there is provided a method of treating a neurological condition in an animal, said method comprising administering an effective amount of in vitro derived neural progenitor cell to the animal.

Preferably, the cells are neural progenitors that have the potential to give rise to multiple lineages and have been derived from undifferentiated hES cell. Preferably, the neural progenitors are committed to a neural fate, more preferably, a midbrain fate. Most preferably, the neural progenitors have been derived from the methods described herein.

The present method can be employed to deliver agents or neural cells to the brain for diagnosis, treatment or prevention of disorders or diseases of the CNS, brain, and/or spinal cord and or peripheral and or autonomic nervous system. These disorders can be neurologic or psychiatric disorders. These disorders or diseases include brain disease such as Alzheimer's disease, Parkinson's disease, Lewy body dementia, multiple sclerosis, epilepsy, cerebellar ataxia, progressive supranuclear palsy, multi-system atrophies, spino-cerebelar degenerations, optic nerve and retinal diseases including retinal and macular degeneration and retinitis pigmentosa, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and other lipid storage and genetic brain diseases and/or schizophrenia. The method can also be employed in subjects suffering from or at risk for nerve damage from cerebrovascular disorders such as stroke in the brain or spinal cord, from CNS infections including meningitis and HIV from tumors of the brain and spinal cord, or from a prion disease. The method can also be employed to deliver agents to counter CNS disorders resulting from ordinary aging (eg anosmia or loss of the general chemical sense), brain injury, or spinal cord injury. The method can also be employed to treat diseases of the peripheral and autonomic nervous systems including but not limited to hereditary neuropathies, inflammatory neuropathies and traumatic neuropathies.

The present method can be employed to deliver agents to the brain for diagnosis, treatment or prevention of neurodegenerative disorders by genetically modifying the hES cells.

The term "treatment" is used in its most broadest sense to include prophylatic (ie preventative) treatment as well as treatments designed to ameliorate the effects of the neurological condition.

An "effective amount" of agent or of hES cells or neural progenitors is an amount sufficient to prevent, treat, reduce and/or ameliorate the symptoms and/or underlying causes of any of the above disorders or diseases. In some instances, an "effective amount" is sufficient to eliminate the symptoms of these disease and, perhaps, overcome the disease itself. When applied to cells, ie effective amount is an amount sufficient to generate cells to prevent, treat, reduce or ameliorate the symptoms.

The in vitro hES derived neural cells or neural progenitors are those cells that are either non-committed but are inclined to differentiate toward a neural progenitor cell type or have an induced committed neural fate, preferably neural progenitors more preferably neural progenitors with a committed midbrain fate, or differentiated TH⁺ or dopaminergic neurons. The cells may be identified by neuronal markers such as DAT, RMP and VMAT2. These markers may be identified in the progenitors or the transplanted cells which have been transplanted. Most preferably, these cells are produced by the methods described herein.

In a preferred embodiment, the neurological condition is Parkinson's disease.

Parkinson's disease (PD) is characterized by the progressive loss in function of dopaminergic neurons. The progressive loss of dopaminergic function interferes with the normal working of the neuronal circuitry necessary for motor control so that patients with PD show characteristic motor disturbances such as akinesia, rigidity and rest tremor. Other symptoms include pain, impaired olfaction, alterations of personality and depression.

According to the invention, neural progenitors or midbrain committed neural progenitors or dopaminergic neuronal cells are generated using the cell culturing methods described above. These cells are then administered to the brain of the patient in need thereof to produce dopamine and restore behavioral deficits in the patient. Preferably, the cells are administered to the basal ganglia of the patient.

The principal therapeutic target in the brain for Parkinson's is the basal ganglia. Other potential sites are substantia nigra which extends forward over the dorsal surface of the basis peduncle from the rostral border of the pans toward the sub-thalamic nucleus. In addition therapeutic target areas are also the locus ceruleus which is located in the rostral pons region and the ventral tegmental area which is located dorsomedial to the substantia nigra.

According to the invention, the cells are administered to the patient's or animal's brain. The cells may be implanted within the parenchyma of the brain, as well as in spaces containing cerebrospinal fluids, such as the sub-arachnoid space or ventricles. The cells may be also implanted into sites outside the central nervous system such as but not limited to the peripheral and autonomic nerve and ganglia. "Central nervous system" is meant to include all structures within the dura mater.

Typically, the neural cells are administered by injection into the brain of the patient. Injections can generally be made with a sterilized syringe. The exact size needle will depend on the species being treated, the needle should not be bigger than 1 mm diameter in any species. Those of skill in the art are familiar with techniques for administering cells to the brain of a patient.

After the neural cells including but not limited to non-committed neural progenitors, committed neural progenitors, neuronal cells of various types are formed according to the cell culturing method previously described, the cells are suspended in a physiologically compatible carrier. As used herein, the term "physiologically compatible carrier" refers to a carrier that is compatible with the other ingredients of the formulation and not deleterious to the recipient thereof. Those of skill in the art are familiar with physiologically compatible carriers. Examples of suitable carriers include cell culture medium (eg, Eagle's minimal essential media), phosphate buffered saline, and Hank's balanced salt solution +/- glucose (HBSS).

The volume of cell suspension administered to a patient will vary depending on the site of implantation, treatment goal and amount of cells in solution. Typically the amount of cells administered to a patient will be a "therapeutically effective amount". As used herein, a therapeutically effective amount refers to the number of transplanted cells which are required to effect treatment of the particular disorder. For example, where the treatment is for Parkinson's disease, transplantation of a therapeutically effective amount of cells will typically produce a reduction in the amount and/or severity of the symptoms associated with that disorder, eg, rigidity, akinesia and gait disorder.

It is estimated that a severe Parkinson's patient will need at least about 100,000 surviving dopamine cells per grafted side to have a substantial beneficial effect from the transplantation. As cell survival is low in brain tissue transplantional in general (5-10%) an estimated 1-4 million dopaminergic neurons should be transplanted. It is estimated that a lower number of neural progenitors committed to give rise to dopaminergic neurons will be required to produce a similar therapeutic response.

Examples of the procedures used in the present invention will now be more fully described. It should be understood, however, that the following description is illustrative only and should not be taken in any way as a restriction on the generality of the invention described above.

EXAMPLES

Example 1

Directed Differentiation of hES Cells into Highly Enriched Cultures of Neural Progenitors A. Induction of Differentiation on Feeders with Noggin Coupled with Manipulation of Culture Conditions.

Figure 1:
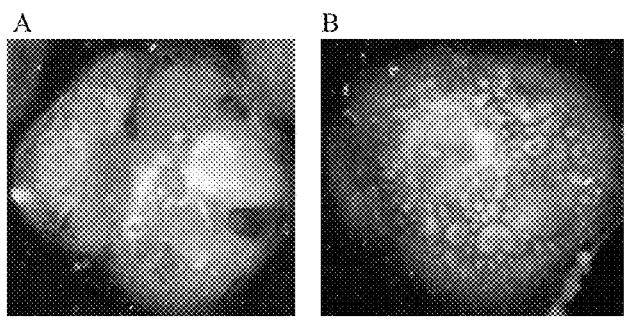

To derive enriched preparations of neural progenitors, differentiation of human ES cells was directed into neural fate by transfer of undifferentiated hES cell clumps onto fresh feeders and culture in a modified hES cell medium with reduced serum concentration and in the presence of the BMP antagonist noggin. Specifically, human ES cells (HES-1 cell line, Reubinoff et al 2000, PCT/AU99/00990) with a stable normal (46XX) karyotype were cultured on mitomycin C mitotically inactivated mouse embryonic fibroblast feeder layer in gelatine coated tissue culture dishes as previously described (Reubinoff et al., 2000 PCT/AU99/00990 and PCT/AU01/00278). To induce differentiation, at the usual passage, clumps of undifferentiated ES cells were plated on fresh feeders and cultured in the usual hES medium supplemented with 10% serum (instead of 20%) and 500 ng/ml of noggin (R&D systems). Noggin (500 ng/ml) was further added to the medium every other day throughout a 6-8 day culture period (3-4 administrations). After 6-8 days, noggin was omitted and the cells were further cultured in the modified medium with 10% serum for additional 4-6 days. At this time about 12-14 days, about 70% of the colonies differentiated mostly into areas that were comprised of tightly packed small cells with a uniform grey opaque appearance under dark field stereo microscope (FIG. 1a, PCT/AU01/00278, PCT/AU01/00735). Other colonies differentiated into areas with structures that could resemble primitive neural rosettes (FIG. 1b).

Clumps of about 150 cells were mechanically isolated by using the razor-sharp edge of a micro glass pipette or a razor blade from the grey opaque areas and replated in serum-free medium supplemented with human recombinant FGF-2 and EGF. Specifically, the clusters of cells were transferred to plastic tissue culture dishes containing neural progenitors growth medium (NPM) that consisted of DMEM/F12 (1:1), B27 supplementation (1:50), glutamine 2 mM, penicillin 50 u/ml and streptomycin 50 µg/ml (Gibco), and supplemented with 20 ng/ml human recombinant epidermal growth factor (EGF), and 20 ng/ml fibroblast growth factor 2 (FGF2) (R & D Systems, Inc., Minneapolis, Minn.). Under these culture conditions the clumps formed free floating spherical structures within 24 hours and sequential propagation and expansion of the sphere cultures was possible as previously described (Reubinoff at al., 2001, PCT/AU01/00278) for prolonged periods (6 months).

Figure 3:
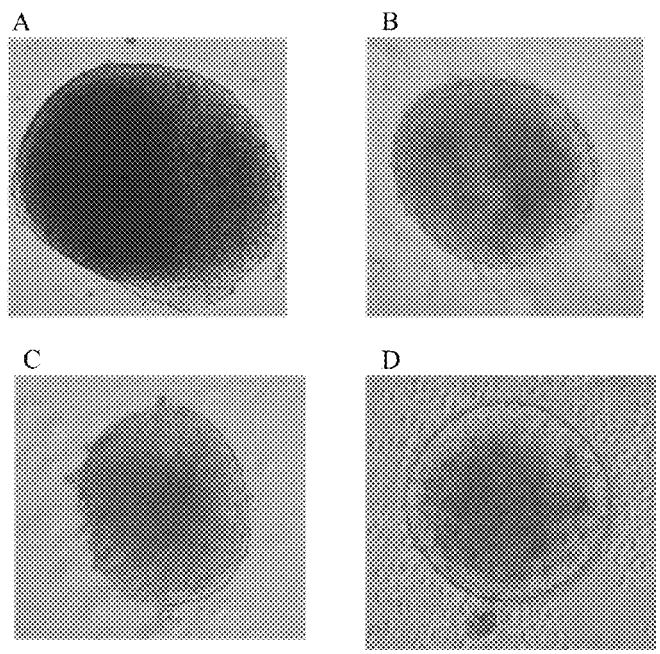

During the initial weeks in culture, the spheres gradually acquired a uniform morphology (FIG. 3 A,B). A detailed analysis of marker expression by the cell within the spheres was conducted at 3-4, 8 and 12 weeks after derivation. The spheres were disaggregated into single cells that were plated, fixed and analyzed by fluorescent immunohistochemistry for the expression of the early neural markers N-CAM, A2B5, PSA-NCAM and nestin. A high proportion of the cells expressed these markers (N-CAM 83±4% A2B5 84±4%, nestin 69±6% PSA-NCAM 74±2%) and the level of expression was stable during the 12 weeks period.

Figure 2:
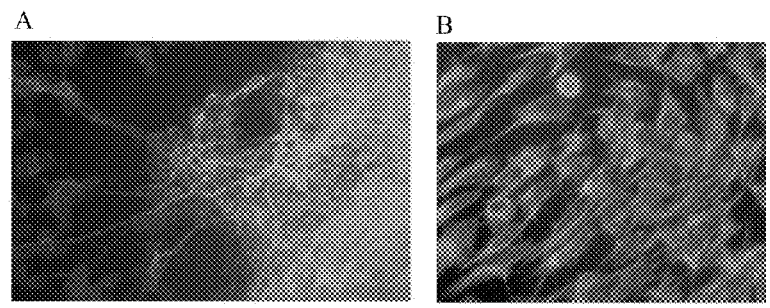

The phenotype of cells within the areas with structures that could resemble primitive neural rosettes (FIG. 1b) was also analyzed. These areas were mechanically dissected, and disaggregated. The cells were plated on laminin and cultured in NPM for two days. Immunophenotyping at that point revealed that 95-100% of the cells expressed N-CAM (FIG. 2A) and nestin (FIG. 2B).

B. Induction of Differentiation by Culture of ES Cell Aggregates in Serum Free Conditions in the Presence of Noggin and FGF2.

In an alternative approach, undifferentiated human ES cell clumps of about 200 cells were transferred into NPM and cultured in suspension in the presence of noggin (350 and 700 ng/ml) for approximately 3 weeks. To further induce neural differentiation, proliferation and prevent the differentiation of neural progenitors the medium was also supplemented with human recombinant FGF-2 (20 ng/ml). LIF (10 ng/ml) was also included in the medium in early experiments. The media was replaced twice a week. Under these culture conditions the clumps of hES cells turned into round spheres within 7 days (FIG. 3 C,D).

To evaluate the effect of these culture conditions, we have evaluated the phenotype of cells within clumps following three weeks of culture. We have examined two concentrations of noggin (350 and 700 ng/ml) in comparison to culture in NPM supplemented with FGF2 in the absence of noggin. The clusters were disaggregated into single cells or small clumps that were plated, cultured for 4 hours on laminin, fixed and analyzed by indirect immunofluorescence for the expression of the early neural markers nestin, A2B5 and N-CAM. Markers of endoderm (probably extraembryonic; low molecular weight (LMW) cytokeratin and laminin) and mesoderm (muscle specific actin and desmin) were examined after a week of differentiation. Immunofluorescence methods and source of antibodies are described below in section (C).

Figure 4:
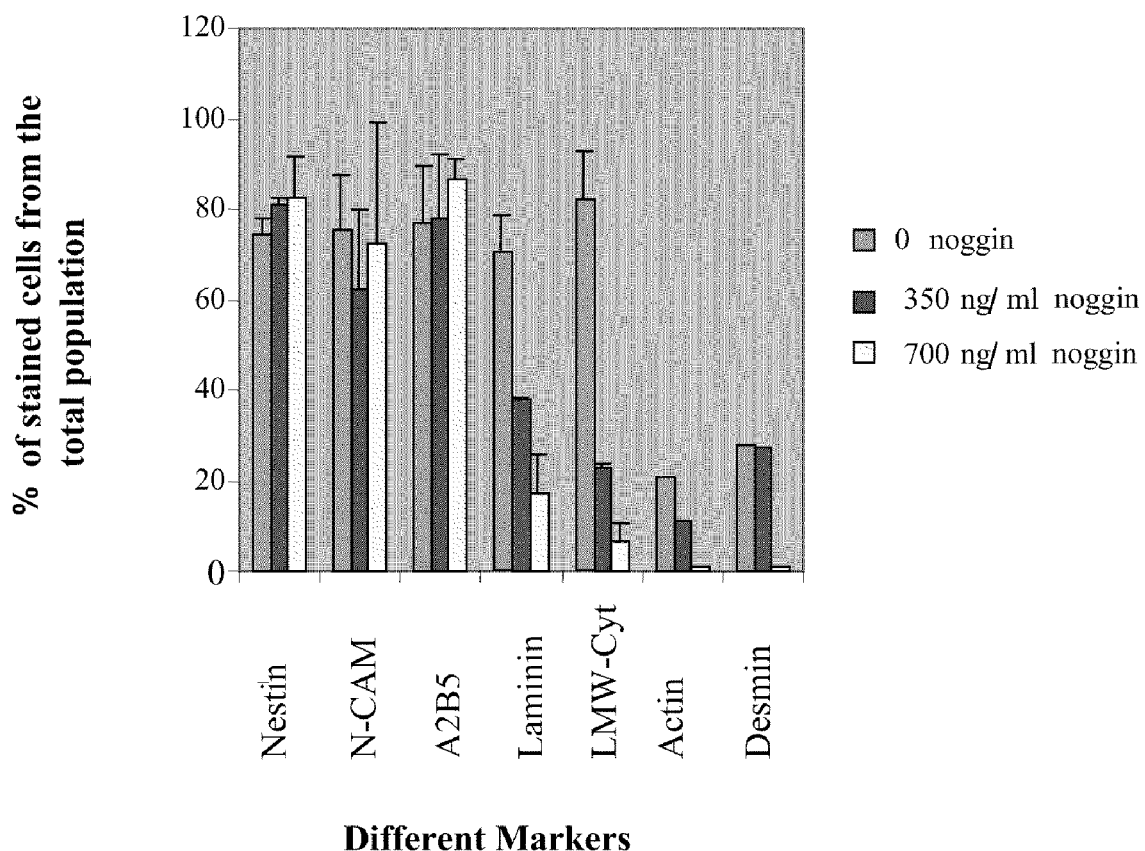

A high proportion (~75%) of the cells within the spheres expressed early neural markers. The percentage of cells expressing nestin and A2B5 was slightly higher in the noggin (700 ng/ml) treated spheres. Noggin treatment had a profound significant effect on the level of expression of endodermal and mesodermal markers. The proportion of cells expressing endodermal and mesodermal markers was significantly reduced after noggin treatment in a dose dependent manner (FIG. 4).

Figure 5:
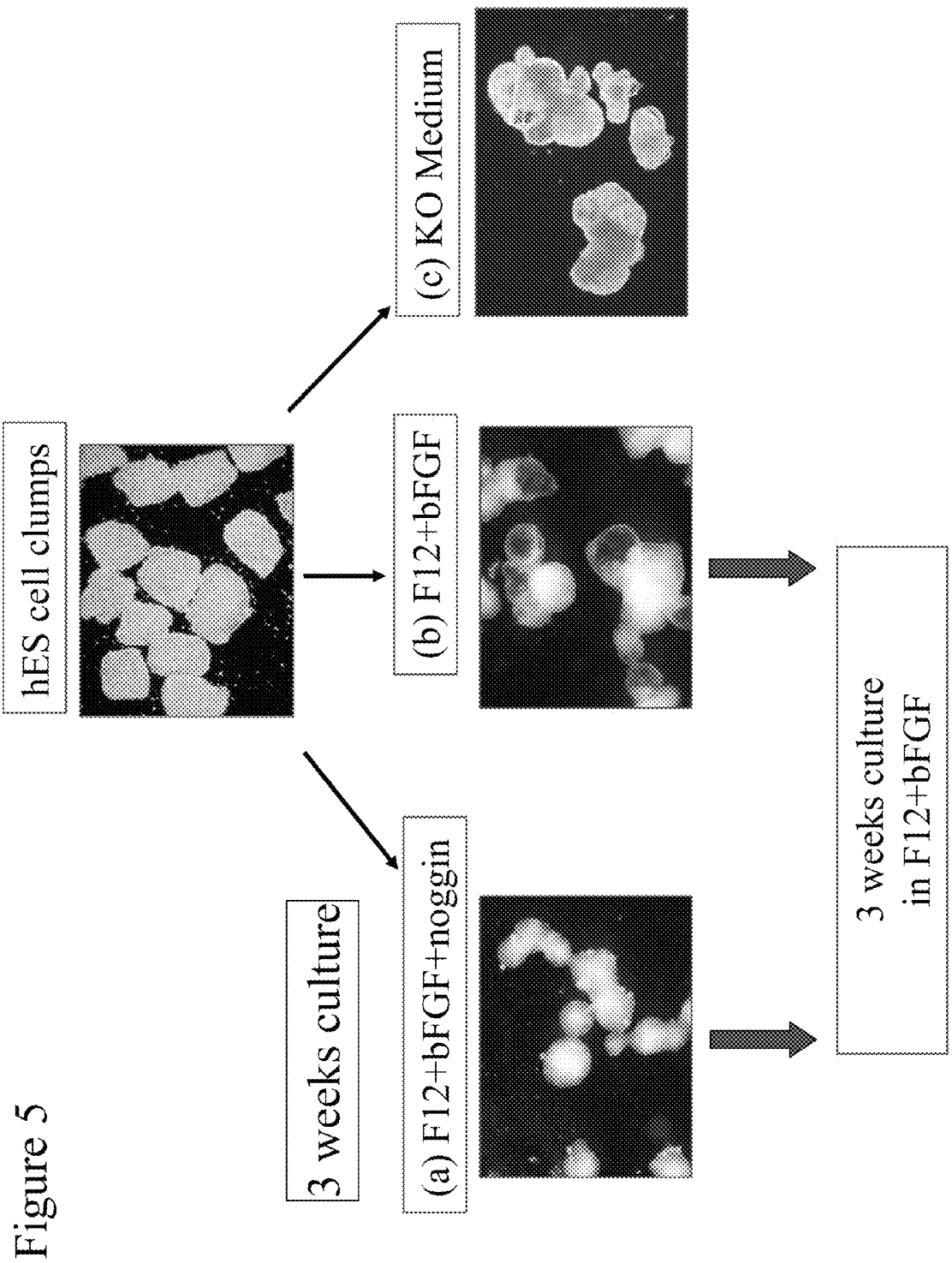
FIG. 5 shows dark field images of clumps of undifferentiated ES cells, and differentiated clumps after culture (3 weeks) in NPM supplemented with FGF2 and noggin (a), the same medium without noggin (b), and knockout medium (c). Clumps from groups a and b were further cultured 3 weeks in NPM supplemented with FGF2 in the absence of noggin.

To analyze and differentiate between the effect of NPM supplemented with FGF2 and noggin on the differentiation of the hES cell clusters we have characterized and compared the differentiation of these clusters following culture in three different media (FIG. 5): (a) NPM supplemented with b-FGF and noggin (700 ng/ml), (b) the same medium without noggin and (c) knockout (KO) medium. After three weeks of culture a significant difference in the morphology of the clusters was observed. Clusters that were cultured in KO medium had the typical morphology of embryoid bodies (EBs, FIG. 5c). Clusters that were cultured in NPM and FGF2 were characterized by cystic structures and areas of dense cells resembling neural spheres (FIG. 5b). Clusters that were cultured in the presence of noggin had the typical morphology of neural spheres without cystic structures (FIG. 5a).

Clusters that were cultured in NPM with (FIG. 5a) or without noggin (FIG. 5b) were further cultured for an additional 3 weeks in NPM supplemented with FGF2 in the absence of noggin (FIG. 5).

Figure 6:
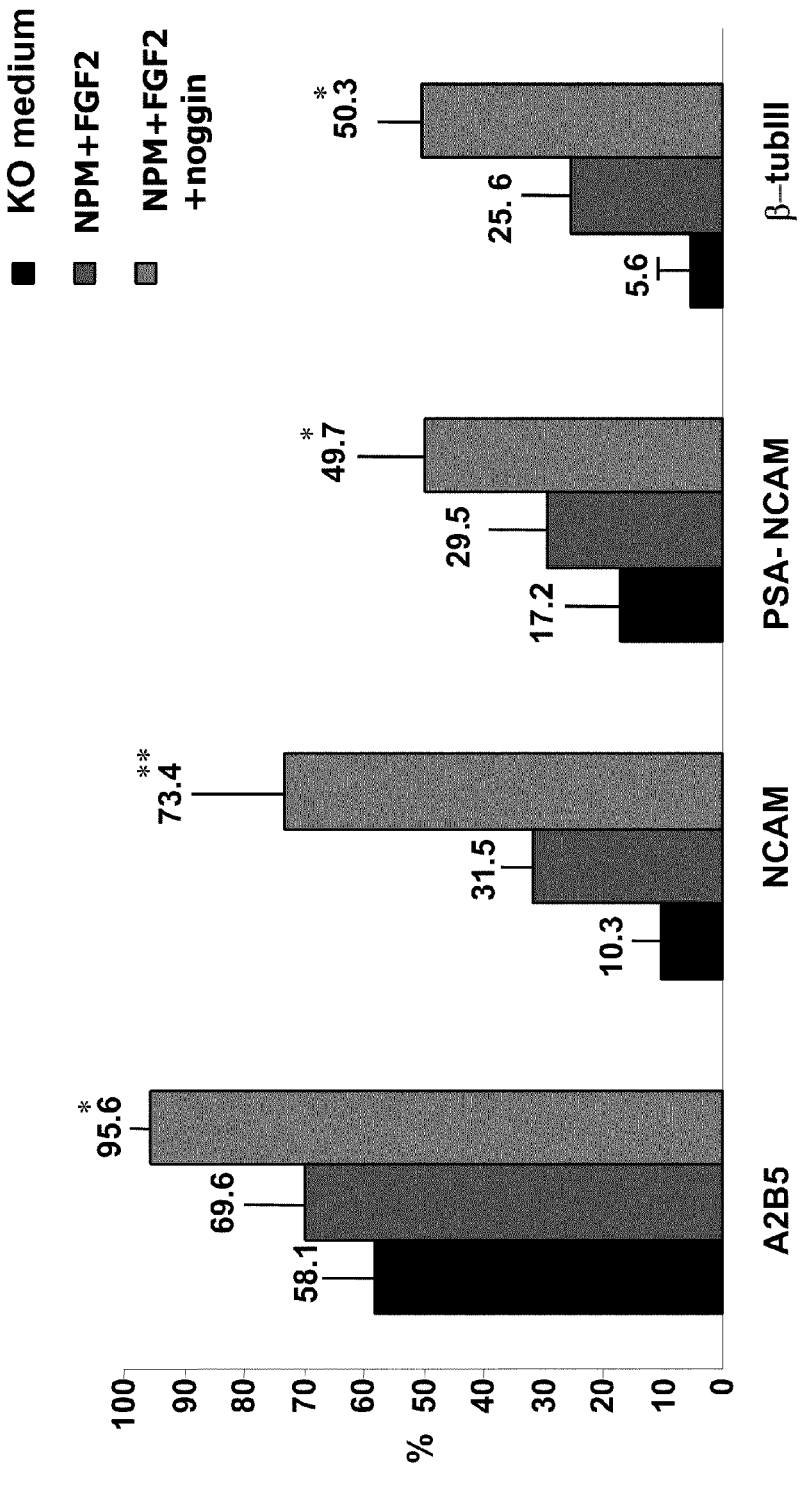
FIG. 6 shows indirect immunofluorescence analysis of the percentage of cells expressing neural markers within hES cell clumps after three weeks of culture in KO medium, NPM+FGF2 and NPM+FGF2+noggin.
Figure 7:
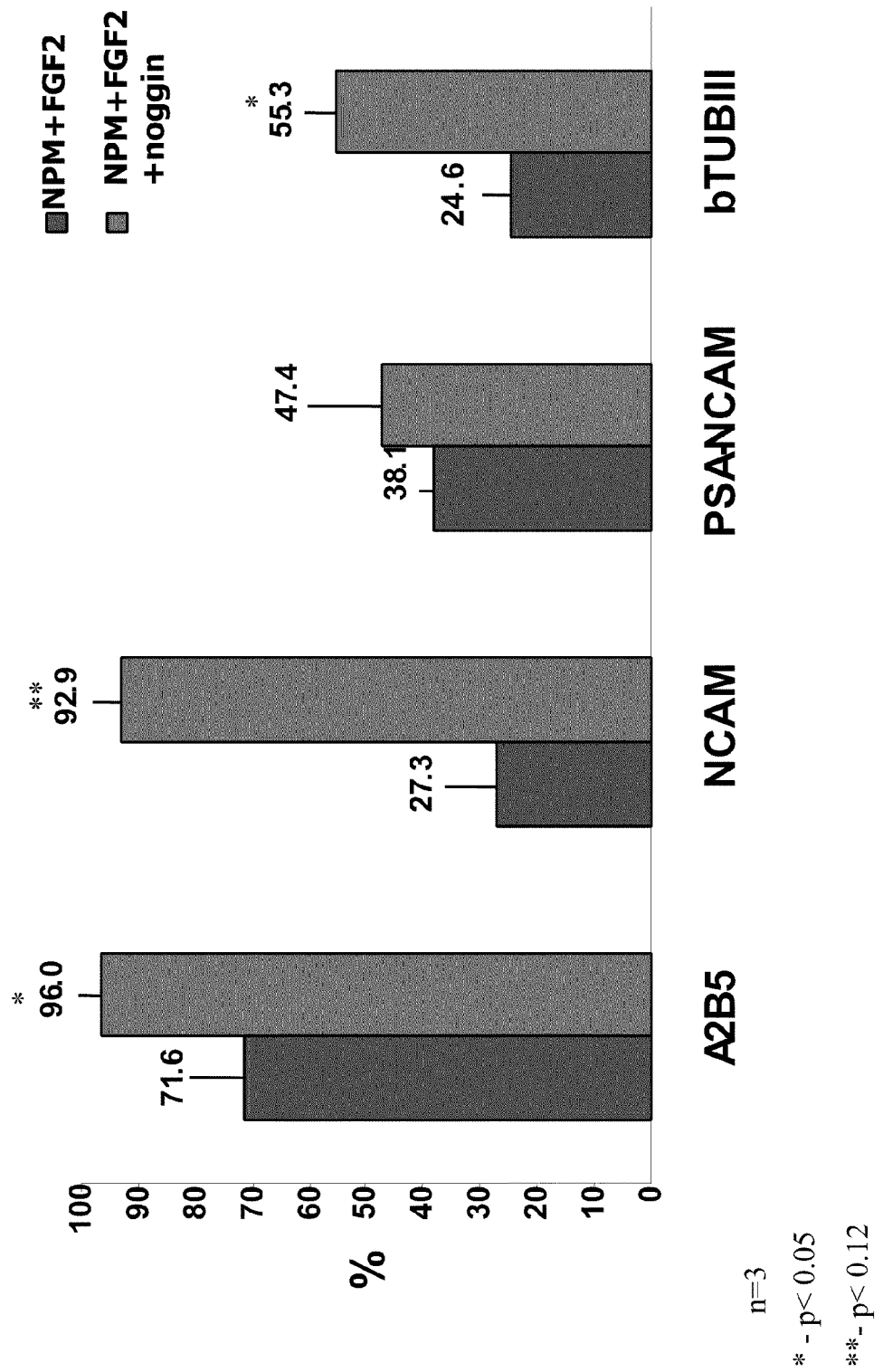
FIG. 7 shows indirect immunofluorescence analysis of the percentage of cells expressing neural markers within hES cell clumps that were cultured 3 weeks in NPM+FGF2 or NPM+FGF2+noggin followed by additional 3 weeks in NPM+FGF2.

To characterize and compare the phenotype of cells within the clusters following differentiation and propagation at the various culture conditions (FIG. 5), the clusters were disaggregated after 3 weeks in culture into single cells or small clumps that were plated, cultured for 4 hours on laminin, fixed and analyzed for the expression of the early neural markers nestin, A2B5, N-CAM, PSA-NCAM and β-tubulin III (FIG. 6). The same analysis was done after additional 3 weeks of culture in NPM supplemented with FGF2 (FIG. 7).

The percentage of cells expressing early neural markers was increased after three weeks culture in NPM+FGF2 in comparison to KO medium. Noggin treatment further significantly increased the percentage of cells expressing the neural markers (95.6% A2B5; 73% NCAM; FIG. 6). After additional 3 weeks of culture in NPM+FGF2 the percentage of cells expressing most of the neural markers was stable in both study groups. The major effect of the additional 3 week culture period was an increase in the percentage of cells expressing NCAM in the noggin treated clumps (from 73% to 93%).

Figure 8:
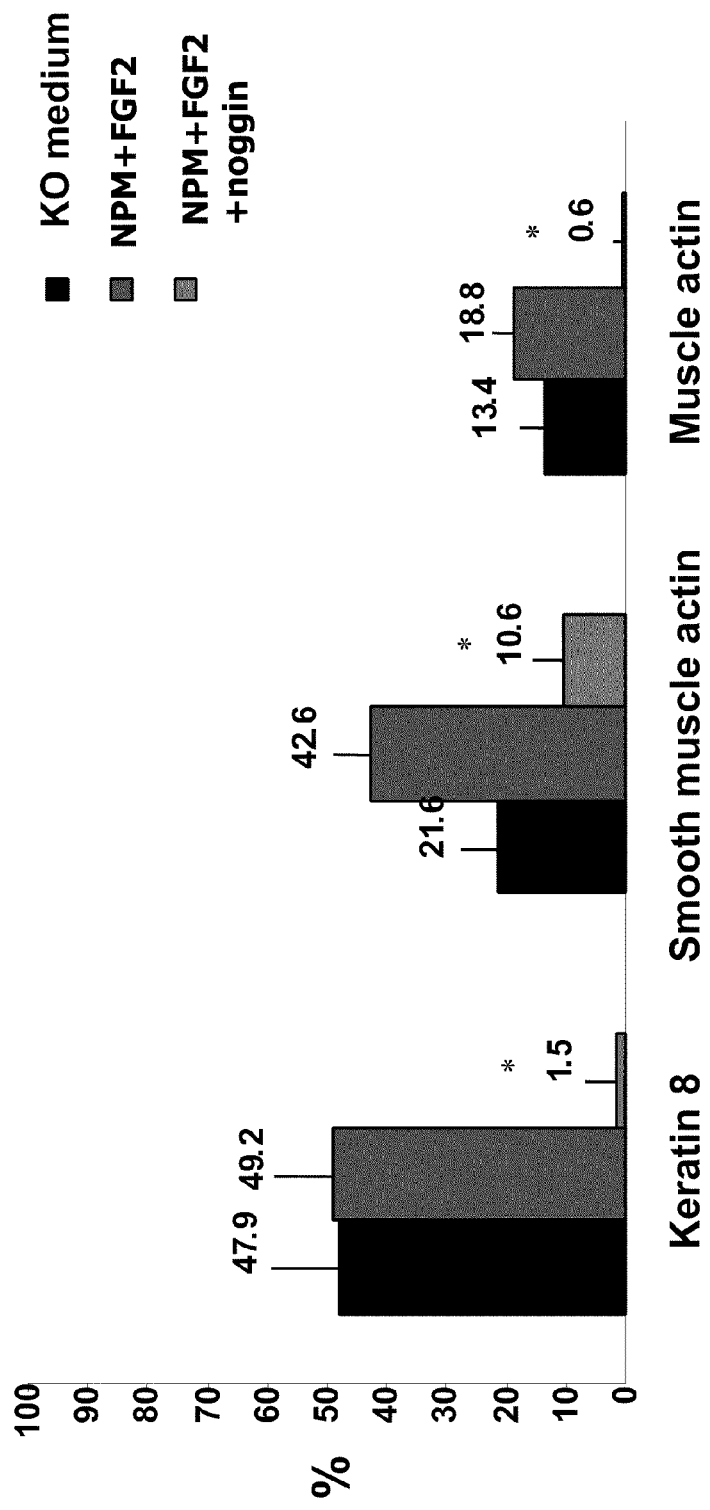
FIG. 8 shows indirect immunofluorescence analysis of the percentage of cells expressing endodermal (probably extraembryonic) and mesodermal markers within hES cell clumps after three weeks of culture in KO medium, NPM+FGF2 and NPM+FGF2+noggin.
Figure 9:
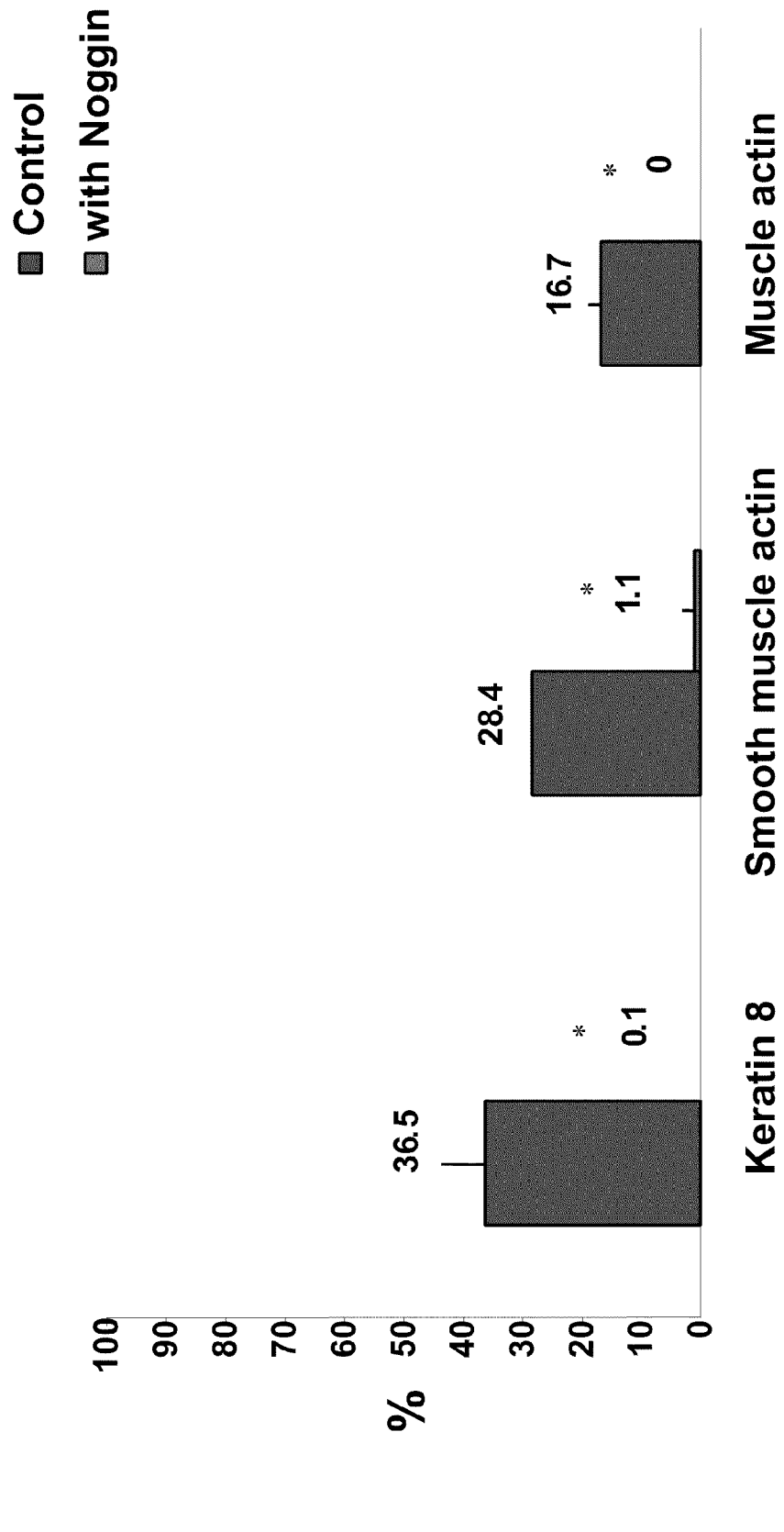
FIG. 9 shows indirect immunofluorescence analysis of the percentage of cells expressing endodermal (probably extraembryonic) and mesodermal markers within hES cell clumps that were cultured 3 weeks in NPM+FGF2 with or without noggin followed by additional 3 weeks in NPM+FGF2.

The percentage of cells within the clumps that expressed non-neural markers at 3 weeks (FIG. 8) and 6 weeks (FIG. 9) of the same floating cultures as above was analyzed. Indirect immuno fluorescence analysis of the expression of non-neural markers was performed following disaggregation of the clumps and one week of differentiation on laminin. The analysis showed a significant reduction in the percentage of cells expressing these markers in the noggin treated cultures after 3 weeks (FIG. 8). Cells expressing these markers were undetectable or rare after additional 3 weeks of culture in NPM+FGF2 (FIG. 9).

At the RNA level, RT-PCR analysis confirmed that in the noggin treated clumps the expression of the endodermal (probably extraembryonic) marker alpha-fetal protein was reduced/undetectable at 3 weeks. This marker was also undetectable at 6 weeks. The expression of the endodermal (probably extraembryonic) marker HNF3α was also reduced/undetectable at 6 weeks of culture. The expression of transcripts of the epidermal marker keratin-14 was significantly reduced at 3 weeks and undetectable at 6 weeks.

Collectively these data suggest that highly enriched cultures of neural progenitors are obtained when undifferentiated clumps of hES cells are cultured in NPM+FGF2 supplemented with noggin. The percentage of neural progenitors was higher after differentiation in NPM+FGF2 compared to KO medium. This is in line with our previous report (PCT/AU01/00278). Noggin treatment further significantly increased the process of neuralization and blocked the differentiation to extraembryonic endoderm (as previously described in PCT/AU01/00735) and epidermis. Either noggin or the culture conditions (NPM) or both reduced the differentiation and/or did not promote the survival of mesodermal cells.

C. Immunohistochemistry Studies

In general, for the immunophenotyping of disaggregated neural progenitor cells and differentiated neurons, fixation with 4% paraformaldehyde for 20 minutes at room temperature was used unless otherwise specified. It was followed by blocking with 5% heat inactivated goat serum (Dako) and permeabilization with 0.2% Triton X (Sigma) in PBS with 0.1% BSA for 30 minutes. Samples were incubated with the primary antibodies at room temperature for one hour. Cells were washed three times with PBS with 0.1% BSA, incubated with the secondary antibodies for 30-45 minutes, counterstained and mounted with Vectashield mounting solution with DAPI (Vector Laboratories, Burlingame, Calif.). Primary antibodies localization was performed by using mouse anti rabbit IgG and goat anti mouse IgG conjugated to Cy3 or FITC from Jackson Lab. West Grove, (PA: 1:100-1:500), or anti rabbit FITC and goat anti mouse FITC from Dako (1:20-

50). Proper controls for primary and secondary antibodies revealed neither non-specific staining nor antibody cross reactivity.

To characterize the immunophenotype of cells within the aggregates, spheres were mechanically disaggregated into single cells or small clumps and plated on poly-D-lysine and laminin in NPM. The cells were fixed after 1 (for analysis of the expression of neural markers) or—3-7 days (for non-neural markers) and examined for the expression of the following markers: laminin (Sigma mouse monoclonal 1:500) and low molecular weight cytokeratin ((cytokeratin 8, Beckon Dickinson, San Jose, Calif. ready to use) as markers of endoderm; muscle actin (Reubinoff et al., 2000), smooth muscle actin (Dako mouse IgG 1:50) and desmin (Dako mouse clone D33 1:50) for mesoderm; nestin (rabbit antiserum a kind gift of Dr. Ron McKay; 1:25 or from Chemicon rabbit anti human 1:100-200), N-CAM (Dako, Carpinteria, Calif.; mouse IgG 1:10-20), A2B5 (ATCC, Manassas, Va.; mouse clone105 1:10-20) and PSA-N-CAM (Developmental Studies Hybridoma Bank, mouse undiluted) as markers of neural progenitors; β-tubulin III (Sigma; mouse IgG 1:2000) for early neurons.

Two hundred cells were scored within random fields (at X200 and X400) for the expression of each of these markers and the experiments were repeated at least 3-5 times.

D. Marker Characterization by rt-pcr

RT-PCR was performed as previously described (Reubinoff et al., 2001). Primer sequences (forward and reverse) and the length of amplified products were as previously described (Reubinoff et al 2001) for alpha-feto-protein and HNF3α and as follows for keratin 8: ATGATTG-GCAGCGTGGAG (SEQ ID NO: 1), GTCCAGCTGT-GAAGTGCTTG (SEQ ID NO: 2) (390 bp).

Example 2

Directed Differentiation of hES Cell-derived Neural Progenitors Towards a Midbrain Fate Neurospheres that were generated from noggin treated ES cell colonies as described above (Example 1) were propagated 21-35 days in NPM supplemented with FGF-2 and EGF. At this point the spheres were chopped into small clumps (2000-3000 cells per clump). FGF-2 and EGF were removed from the medium and the progenitors were directed to take a midbrain fate by treatment with various factors for 6-8 days. During treatment with the various factors the clumps were either cultured in suspension or plated on poly-D-lysine and laminin. The factors included. FGF1, FGF8, FGF17 (R&D Systems) at concentrations of 100-200 ng/ml SHH (R&D Systems) at 0.5-1 µg/ml. Other signal transduction inducers: cAMP inducers: IBMX (Sigma, 0.25 mM), forskolin (Sigma 50 µM), PKC inducers PMA (Sigma 200 nM) and dopamine (Sigma 20 µM) were also used. The medium was also supplemented with the survival factors Ascorbic acid (AA) (Sigma) at concentration of 400-800 µM and NT4 (R&D Systems) at concentration of 20 ng/ml. The medium was changed every other day. To induce further differentiation into neurons, the spheres were again disaggregated into small clumps and plated on poly-D-lysine (30-70 kDa. 10 µg/ml, Sigma) and laminin (4 µg/ml, Sigma) and cultured in NPM in the absence of the factors and in the presence of AA with or without NT4 for 5-10 days. Differentiated cells were analyzed by indirect immunofluorescence (as described in example 1) for the expression of β-tubulin type III (Sigma, 1:1000-3000) Tyrosine hydroxylase (TH) (Sigma anti mouse monoclonal, 1:250-500 and Pel-Freez anti rabbit polyclonal, 1:50-100) dopamine transporter (DAT; _Chemicon; rabbit polyclobal 1:50-100) and Nurr1 (Santa Cruz, Calif.; rabbit poly clonal 1:100-200). The proportion of clumps of cells that were comprised of a significant number of TH+ cells (>50 cells) was scored. Double immunostaining for TH and β-tubulin type III was used to analyze the percentage of cells within clumps expressing TH from the total number of neurons (β-tubulin type III+cells). Multiple confocal microscopy images of consecutive planes through the clump were projected into one image for this analysis (FIG. 14) Ten-fifteen random fields were analyzed.

The proportion of cells that differentiated into TH+ neurons when the medium was not supplemented with midbrain fate inducers or survival factors was very poor (about 1%, PCT/AU01/00278, FIG. 11D, E) and TH+ clumps were not generated. The differentiation into TH+ neurons was poorer with high passage spheres as opposed to low passage ones and therefore low passage (30-35 days in culture) spheres were used in the in vitro studies).

Supplementation of the culture medium with ascorbic acid at the time of removal of FGF-2 and EGF as well as during differentiation of the progenitors on substrate gave rise to a significant number of TH+ neurons in 35% of the clumps (FIGS. 12 and 13 bar 6) At the cellular level, 45% of the neurons in these cultures expressed TH (FIG. 14, 15).

Treatment with FGF-8 (200 ng/ml) in combination with AA significantly increased the proportion of TH+ clumps to a level of 67%. (FIG. 10, 12). Analysis at the cellular level, using confocal microscopy, also showed an increase (to 77%) in the percentage of TH+ neurons from the total number of neurons (FIG. 15). In contrast SHH treatment had no effect on the proportion of TH+ clumps. The effect of SHH was evaluated in combination with AA or in combination with FGF-8 and AA and in both cases it did not increase the proportion of TH+ neurons (FIG. 12).

To demonstrate that the TH+ neuron enriched cultures that are generated following treatment with FGF8 and AA include dopaminergic neurons we have examined the expression of DAT. In vertebrates, DAT is exclusively expressed in DA neurons (Lee et al., 2000). Indirect immunofluorescence studies demonstrated cells expressing DAT within the cultures of differentiated TH+ cells (FIG. 16). This data suggested that the treatment with FGF8 and AA induced differentiation into dopaminergic neurons.

FGF-17 was also found to have the potential to induce differentiation towards a midbrain fate. Following treatment with the combination of FGF-17 and AA 60% of the clumps were comprised of a significant number of TH+ neurons (FIG. 12). The inductive effect of FGF-17 was not significantly different from the effect of FGF-8. Fluorescent images of clumps of differentiated neurons following treatment with FGF-17 and AA are demonstrated in FIG. 11. A significant proportion of the cells within these clumps express TH.

Directing the differentiation of hES cell derived neural progenitors towards TH+ neurons was also accomplished by using the combination of FGF-1, cAMP activators IBMX and Forskolin, Protein kinase C (PKC) activator PMA, dopamine and AA. Following treatment with this set of factors (FGF-1 at 200 ng/ml) 66-75% of the clumps of differentiated neurons contained a significant number of TH+ neurons (FIG. 13). The set of these factors was as efficient as FGF-8 and AA or FGF-17 and AA. It should be noted that a 55% proportion of TH+ clumps was obtained when the signal transduction activators (IBMX, Forskolin, PMA) dopamine and AA were used without FGF-1. In contrast to the effect of FGF-1 at 200 ng/ml, the addition of FGF-1 or FGF-8 at a concentration of 10 ng/ml to the set of these factors did not increase the proportion of TH+ clumps (FIG. 13). In these experiments the surviving factor NT4 was added to AA at the stage of final differentiation when the neurospheres were plated on laminin and cultured in NPM.

The transcriptional factor Nurr1 is required for the induction of midbrain DA neurons, which fail to develop in Nurr1-null mutant mice (Zetterstrom et al. 1997). Forced expression of the Nurr1 gene may be used to direct the differentiation of human ES cell-derived neural progenitors into DA neurons. We have developed a lentiviral vector transduction system for the introduction of stable genetic modifications into human ES cells (Gropp et al., 2003, patent application No. PCT/AU02/0175).

We have used this system to generate hES cells expressing Nurr1. The vector that we have used (pSIN18.cPPThEF-1α.Nurr1.hPGK.Puro.WPRE) include the mouse Nurr1 gene under the control of hEF1 α promoter followed by a selection marker gene (puromycine resistance element) under the control of hPGK promoter. Neural spheres were developed from the genetically modified hES cells, propagated and induced to differentiate in the presence of AA as detailed above. Indirect immunofluorescence analysis demonstrated neurons coexpressing Nurr1 and TH (FIG. 17). It should be noted that it was not possible to demonstrate by immunostaining the expression of Nurr1 by wild type hES cells following induction of differentiation according to the same protocol.

Example 3

Improvement of Behavioral Deficit in an Animal Model of Parkinson's Disease Following Transplantation of hES Cell Derived Neural Progenitors A Parkinson's disease model in rats was induced by stereotaxic injection of the neurotoxin 6-hydroxydopamine to cause unilateral nigrostriatal lesions. 8 µg/rat of 6-OH dopamine were injected in 4 µl into the right Substantia Nigra. Coordinate of injection were P=4.8, L=1.7, H=−8.6.

Two weeks after the injection of neurotoxin the disease severity was examined in each rat individually by administration of apomorphine (25 µg/100 g body weight) and quantification of contralateral rotational behavior by computerized rotameter system (San-Diego Instruments). It should be noted that in early experiments, rotations were counted by an observer 4 times every 12 minutes, for three minutes each time after apomorphine administration. Animals with strong baseline rotational behavior (>500 rotations/hour) were selected for transplantation. In these animals immunofluorescent studies of brain sections demonstrated that the injection of the neurotoxin resulted in complete loss of tyrosine-hydroxylase stained neurons in the ipsilateral striatum, as compared to preserved tyrosine-hydroxylase in the contralateral side (FIG. 18).

Human ES derived neural progenitors (as described in Example 1a) were used for transplantation. The phenotype of cells within the neural spheres was characterized prior to transplantation by immunocytochemical studies (as described in Example 1c) and RT-PCR.

For PT-PCR studies, total RNA was extracted from: (1) human ES cell colonies (one week after passage), (2) free-floating spheres after 6 weeks in culture, (3) differentiated cells growing from the spheres at 1 week after plating on laminin in the presence of AA 400 µM (Sigma) and the survival factors NT3 10 ng/ml, NT4 20 ng/ml and BDNF 10 ng/ml (all human recombinants from R&D). Total RNA was isolated using RNA STAT-60 solution (TEL-TEST, Inc., Friendswood Tex.) or TRI-reagent (Sigma) followed by treatment with RNase-free DNase (Ambion, The RNA company, Austin Tex.). The cDNA synthesis was carried out using Moloney murine leukemia virus (M-MLV) reverse transcriptase and oligo (dT) as a primer, according to the manufacturers' instructions (Promega, Madison Wis.). To analyze relative expression of different mRNA, the amount of cDNA was normalized based on the signal from GAPDH mRNA. Levels of marker mRNAs expressed by neural spheres and differentiated cells were compared to that in the undifferentiated hES cells. PCR was carried out using standard protocols with Taq DNA Polymerase (Gibco invitrogen corporation). Amplification conditions were as follows: denaturation at 94° C. for 15 seconds, annealing at 55-60 for 30 seconds, and extension at 72° C. for 45 seconds. The number of cycles varied between 18 and 40, depending on the particular mRNA abundance. Primer sequences (forward and reverse 5'-3') and the length of amplified products were as follows:

```
Oct4-CGTTCTCTTTGGAAAGGTGTTC,        (SEQ ID NO: 3)

ACACTCGGACCACGTCTTTC, 320 bp;       (SEQ ID NO: 4)

Otx2-CGCCTTACGCAGTCAATGGG,          (SEQ ID NO: 5)

CGGGAAGCTGGTGATGCATAG, 641 bp;      (SEQ ID NO: 6)

Pax2-TTTGTGAACGGCCGGCCCCTA,         (SEQ ID NO: 7)

CATTGTCACAGATGCCCTCGG, 300 bp;      (SEQ ID NO: 8)

Pax5-CCGAGCAGACCACAGAGTATTCA,       (SEQ ID NO: 9)

CAGTGACGGTCATAGGCAGTGG, 403 bp;     (SEQ ID NO: 10)

Lmx1B-TCCTGATGCGAGTCAACGAGTC,       (SEQ ID NO: 11)

CTGCCAGTGTCTCTCGGACCTT, 561 bp;     (SEQ ID NO: 12)

Nurr1-GCACTTCGGCAGAGTTGAATGA,       (SEQ ID NO: 13)

GGTGGCTGTGTTGCTGGTAGTT, 491 bp;     (SEQ ID NO: 14)

En1-CTGGGTGTACTGCACACGTTAT,         (SEQ ID NO: 15)

TACTCGCTCTCGTCTTTGTCCT, 357 bp;     (SEQ ID NO: 16)

En2-GTGGGTCTACTGTACGCGCT,           (SEQ ID NO: 17)

CCTACTCGCTGTCCGACTTG, 368 bp;       (SEQ ID NO: 18)

AADC-CTCGGACCAAAGTGATCCAT,          (SEQ ID NO: 19)

GGGTGGCAACCATAAAGAAA, 252 bp;       (SEQ ID NO: 20)

TH-GTCCCCTGGTTCCCAAGAAAAGT,         (SEQ ID NO: 21)

TCCAGCTGGGGGATATTGTCTTC, 331 bp;    (SEQ ID NO: 22)

β-actin-CGCACCACTGGCATTGTCAT,       (SEQ ID NO: 23)

TTCTCCTTGATGTCACGCAC, 200 bp;       (SEQ ID NO: 24)

GAPDH-AGCCACATCGCTCAGACACC,         (SEQ ID NO: 25)

GTACTCAGCGCCAGCATCG 301 bp;         (SEQ ID NO: 26)

Ptx3 (TGGGAGTCTGCCTGTTGCAG,         (SEQ ID NO: 27)

CAGCGAACCGTCCTCTGGG 372 bp)"        (SEQ ID NO: 28)
```

The hES cell-derived neural spheres were transplanted after partial mechanical dissociation of the spheres into small clumps into the striatum of the rats (400,000 cells/animal) with a hamilton syringe along 2 tracts per striatum, using a stereotaxic device. Coordinate for transplantation were A-P=0, L=3.5, H=−7.5 to −4.5 and A=1, L=2, H=−7.5 to −4. Neural spheres that were passaged for 6 weeks (with high potential of generating neurons and specifically dopaminergic neurons) and neural spheres that were passaged for 11 weeks (With a lower potential for generating dopaminergic cells) were transplanted. Control rats underwent sham operation and were injected with saline. Animals received Cyclosporin A treatment (10 mg/Kg) throughout the experiment.

At 2 weeks, 1 month, 2 months and 3 months after transplantation, the severity of the disease was scored by pharmacological and non-pharmacological tests and compared between hES cell transplanted and vehicle transplanted animals. Rotations were counted by a computerized rotameter system for 1 hour after S.C. Injection of apomorphine (25 μg/100 g body weight) and for 1 hour after I.P. d-amphetamine (4 mg/kg performed 2 days later) (in early experiments, rotations were counted by an observer as described above). Non-pharmacological tests included the stepping adjustments (Olsson et al., 1995) and forelimb placing (Lindner et al., 1997) tests. The number of stepping adjustments was counted for each forelimb during slow-sideway movements in forehand and backhand directions over a standard flat surface. The stepping adjustments test was repeated three times for each forelimb during three consecutive days. The forelimb placing test assesses the rats' ability to make directed forelimb movements in response to a sensory stimuli. Rats were held with their limbs hanging unsupported. They were then raised to the side of a table so that their whiskers made contact with the top surface while the length of their body paralleled the edge of the tabletop. Normally, rats place their forelimb on the tabletop almost every time. Each test included ten trials of placing of each forelimb and was repeated in three consecutive days. The results of both tests are expressed as percentage of forelimb stepping adjustments and placing in the lesioned side compared to the non-lesioned side. The mean number of rotations and the mean results (in percentage) of non-pharmacological tests were compared between the experimental groups using student t-test.

The rats were then sacrificed and their brains processed for immunohistochemical studies as previously described (Reubinoff et al., 2001) to determine the fate of the engrafted cells. Transplanted human cells were identified by immunohistochemistry for human specific markers, such as anti-human mitochondrial antibody and anti-human ribonucleic protein (Reubinoff et al 2001). Tyrosine-hydroxylase (TH) stains were performed on thick (20-40 micron) sections to quantify TH density in the striatum and substantia nigra as well as on standard 8 micron section to double stain and co-localize with the human specific markers.

A Rabbit anti TH antibody from Chemicon was used (at 1:100) followed by goat anti-rabbit IgG secondary antibody, conjugated to Cy3 (Jackson immunoresearch laboratory PA; 1:500). TH density was quantified using a computerized image analysis system. Graft survival was analyzed by the computerized image analysis system for staining of the human specific markers. Cell proliferation within the graft was analyzed by immunohistochemical evaluation of the percentage of cells that were decorated with anti PCNA (Chemicon, mouse monoclonal; 1:100) or anti Ki 67 (Novocastra Laboratories Ltd UK; rabbit polyclonal 1:100). Differentiation of transplanted cells into dopaminergic neurons was confirmed by immunohistochemical studies using anti human DAT (Chemicon; rat monoclonal 1:2000) followed by FITC conjugated goat anti rat (Molecular Probes)

Prior to implantation into Parkinsonian rats, the phenotype of the cells within spheres that were propagated 6 weeks in culture was characterized as well as their developmental potential to give rise to midbrain DA neurons. Indirect immunofluorescence analysis following disaggregation of the spheres demonstrated that >90% of the cells within the spheres expressed markers of neural progenitors (FIG. 19). Thus, as demonstrated above, the sphere cultures were highly enriched for neural progenitors.

Successful differentiation of the hES cell derived NPs into midbrain DA neurons probably require the induction of the same key regulatory genes that are expressed by neural progenitor cells during the development of the midbrain in vivo (Lee et al., 2000). Among these key genes are the OTX homeobox genes (OTX1 and OTX2) that are widely expressed at the early stages of neuroectoderm differentiation. Interactions between OTX genes are thought to specify the development of the midbrain and hindbrain (Simeone 1998; Acampora D and Simeone 1999). The genes Pax2, Pax5, Wnt1, En1 and En2 that are expressed further downstream during midbrain development and serve as early organizers surrounding the ventral midbrain progenitors neurons (Stoykova, & Gruss 1994; Rowitch & McMahon 1995). Lastly, the transcription factors Nurr1 and Lmx1b that are implicated in the final specification of the mesencephalic dopamine systems (Zetterstrom et al., 1997; Smidt et al., 2000). These regulatory genes were all expressed by the progenitors within the spheres. The level of expression of these regulatory genes was up regulated upon differentiation (FIG. 20). These findings suggested that the neural progenitors had the developmental potential to give rise to midbrain DA neurons. Some of the genes were also weakly expressed by cells within the hES cell cultures probably reflecting early background neural differentiation. It should be noted that Oct4 was not expressed by the sphere cultures suggesting that the spheres did not include undifferentiated hES cells.

In early experiments we have compared the rotational behavior of a limited number of rats following transplantation of early passage and late passage neural spheres.

In the experimental group that was transplanted with human neural spheres that were passaged for 11 weeks prior to transplantation there was a mild but statistically significant clinical effect at 3 months post-transplantation (FIG. 21). As compared to baseline apomorphine-induced rotational behavior, the control animals exhibited 100.25±9% rotation, while the transplanted animals developed 79±19% rotations (p=0.04).

In the experimental group that was transplanted with human neural spheres that were passaged for 6 weeks prior to transplantation, a clinical effect was observed as early as 1 month after transplantation. At this time point the rotational behavior in transplanted animals had already decreased to 72±14% of baseline (as compared to 102±18% in the control group, p=0.04). Moreover, the effect of apomorphine in the transplanted animals lasted a shorter length of time, with rotational behavior at 30 minutes after injection of apomorphine reducing to 65±12% of control (p=0.01). At 2 months after transplantation the rotational behavior, in transplanted rats decreased further to 58% of baseline (versus 102% in controls, p=0.006, student t-test). Again, the shortening of length of time of rotational behavior was evident, as after 40 minutes, the transplanted animals exhibited 43% rotations as compared to control (p=0.005, FIG. 22).

These results are in line with in-vitro studies and suggest that human neural spheres (of early passage) that have a higher potential to generate dopaminergic cells in-vitro also induce a stronger and more rapid clinical improvement in the Parkinsonian rats.

We have therefore transplanted in following experiments only early passage (6 weeks) spheres.

To further study the behavior of Parkinsonian rats after stem cell transplantation we have extended the number of transplanted and control animals, included analysis of rotation after administration of both apomorphine and amphetamine and evaluated the behavior of animals in non-pharmacological tests. It should be noted that non-pharmacological tests provide a more direct measure of motor deficits analogous to those found in human Parkinson's disease (Kim et al., 2002). The results of the pharmacological tests are presented in FIGS. 23 and 24. These tests demonstrated a significant reduction of rotational behavior in transplanted animals. Both the stepping adjustments and forelimb placing non-pharmacological tests also demonstrated a significant increase in mobility after stem cell therapy (FIG. 25). In conclusion, the results of both, the pharmacological and non-pharmacological tests, demonstrated a significant reduction of Parkinsonism following transplantation of human ES cell-derived neural progenitors.

The fate of the transplanted human neural progenitors was studied by immunohistochemistry and RT-PCR. The sites of transplants were identified on H&E stained coronal sections. The human cells were found in the striatum along the injection tracts, identified by immunostainings for human specific mitochondrial marker (FIG. 26), human specific ribonuclear protein and nestin (FIG. 27).

To evaluate the survival of the graft, sections were stained for human mitochondria. We compared the size of transplants at 24 hours and 3 months post transplantation. Since there was edema and free blood within and around the transplants at 24 hours, we measured the amount of human cells by quantifying the human-specific mitochondrial staining in low-power microscopic fields. This was calculated by multiplying the entire stained area with fluorescence intensity (above background). At the center of the transplant, the area of graft at 24 hours was 94+/−34 (arbitrary units; n=6) and at 12 weeks it was 43+/−18 units (n=5). This indicates approximately 45% graft survival at 12 weeks after transplantation.

Given the potential of ES cells to generate teratomas after transplantation, we have evaluated the percentage of proliferating cells within the grafts. At 24 hours post transplantation, the majority of cells (64.5%) were in a proliferative state as indicated by positive PCNA and ki67 staining. At 12 weeks, there were very rare (<0.2%) PCNA+ cells (FIG. 28). Ki-67+ or PCNA+ cells were not observed in the host striatal parenchyma near the graft. In addition, H&E stained sections, covering the entire brain did not reveal teratomas or any other tumor formation in transplanted rats.

Double staining with anti TH and anti human mitochondria at 12 weeks post-transplantation demonstrated that TH+ neurons were generated from the transplanted human cells (FIG. 29). The number of TH+ fibers counted in human mitochondria+ areas, relative to number of DAPI+ counterstained nuclei, indicated that 0.41+/−0.3% of human cells generated TH+ fibers (n=9). If approximately $4 \times 10^5$ viable cells were transplanted into each rat, it may be estimated, therefore, that the transplants generated on average 740 TH+ neurons at 12 weeks post-transplantation.

To support the acquisition of a dopaminergic fate by the engrafted human progenitors, we have demonstrated by immunohistochemistry the expression of human DAT within the lesioned striatum 12 weeks after transplantation (FIG. 29E). We have further demonstrated the expression of human specific transcripts of midbrain markers in brain samples from transplanted animals. Total RNA was extracted using the RNeasy kit (Qiagen) from midbrain samples that included the graft from stem cell (n=2) and vehicle transplanted (n=1) Parkinsonian rats. The RT-PCR reaction and the details of human specific primers are described above, Transcripts of human midbrain and dopaminergic neuron markers were expressed in samples from animals that received stem cell transplantation and were not detected in control animals (FIG. 30).

In conclusion the results of these experiments demonstrate the long-term survival of hES cell-derived neural progenitors after transplantation to the stratum of parkinsonian rats. Proliferation of the transplanted cells decayed with time, teratoma tumor formation was not observed and the engrafted progenitors differentiated in vivo into DA neurons that led to functional recovery of Parkinsonism.

Example 4

Transplantation of Human Embryonic Stem Cell-Derived Neural Progenitors Corrects Deficits in a Rat Parkinson Model Highly enriched cultures of neural progenitors from hES cells were grafted into the striatum of Parkinsonian rats. A significant fraction of the graft survived for at least 12 weeks, the transplanted cells stopped proliferating and teratoma tumors were not observed. The grafted cells differentiated in vivo into DA neurons though at prevalence (0.41%) similar to the one observed following spontaneous differentiation in vitro. Transplanted rats exhibited significant improvement in rotational behavior that was induced by d-amphetamine and by apomorphine, and in stepping and placing non-pharmacological behavioral tests. Long-term survival of the grafted cells, lack of teratoma tumor formation, and the spontaneous differentiation of a fraction of the transplanted cells into DA neurons that reduced motor asymmetries and improved behavioral deficits of Parkinsonian rats was demonstrated. This study indicates the potential of hES cells to induce functional recovery in an animal model of Parkinson's disease.

A Development and Characterization of hES Cell-derived NPs

Differentiation of hES cells into highly enriched cultures of proliferating NPs was accomplished according to our simple two-step protocol (Reubinoff et al., 2001) with some modifications. In the first step, hES cell colonies (FIG. 31A) were cultured for prolonged periods on feeders in the presence of the BMP antagonist noggin. Under these culture conditions, the hES cells in most of the colonies differentiated almost uniformly into tightly packed small progenitor cells. Briefly, human ES cells (HES-1 cell line, Reubinoff et al. 2000) with a stable normal (46XX) karyotype were cultured on mitomycin C treated mouse embryonic fibroblast feeder layer in gelatin-coated tissue culture dishes (FIG. 31A). To induce neural differentiation, clumps of undifferentiated hES cells were plated on fresh mitotically inactivated feeders and cultured for eight days in serum containing medium comprised of DMEM (Gibco, Gaithersburg, Md.), containing glucose 4500 mg/L without sodium pyruvate, supplemented with 10% fetal bovine serum (Hyclone, Logan, Utah), 0.1 mM beta-mercaptoethanol, 1% non-essential amino acids, 2 mM glutamine, 50 u/ml penicillin, 50 µg/ml streptomycin (Gibco) and 500 ng/ml noggin (R&D Systems Inc., Minneapolis, Minn.). The medium was replaced every other day. Noggin was then omitted and the cells were further cultured in the same medium for additional 6 days. At this time, 70%-90% of the colonies differentiated almost uniformly into tightly packed small cells with a uniform gray opaque appearance under dark field stereomicroscopy (FIG. 31B). In parallel, the colonies acquired a nearly uniform gray opaque appearance under dark field stereomicroscope (FIG. 3B).

In the second step, patches containing about 150 cells each were cut out from the gray opaque areas, using a razor blade (surgical blade #15), and replated in serum-free medium that consisted of DMEM/F12 (1:1), B27 supplementation (1:50), glutamine 2 mM, penicillin 50 u/ml and streptomycin 50 µg/ml (Gibco), and supplemented with 20 ng/ml human recombinant epidermal growth factor (EGF), and 20 ng/ml basic fibroblast growth factor (bFGF) (R & D Systems Inc.). The clusters of cells developed into round spheres that were sub-cultured once a week as previously described (Reubinoff et al., 2001) (FIG. 31C). The medium was replaced twice a week.

At this stage, prior to implantation into Parkinsonian rats, the phenotype of the cells within the spheres was characterized as well as their developmental potential to give rise to midbrain DA neurons. Indirect immunofluorescence analysis following disaggregation of the spheres demonstrated that >90% of the cells within the spheres expressed markers of neural progenitors (FIG. 32J). Thus, the sphere cultures were highly enriched for neural progenitors.

The regulatory genes (OTX1 AND OTX2, Pax2, Pax5, Wnt1, En1 and En2) and the transcription factors Nurr1 and Lmx1b were all expressed by the progenitors within the spheres suggesting that these neural progenitors had the developmental potential to give rise to midbrain DA neurons (FIG. 32). Some of the genes were also weakly expressed by cells within the undifferentiated hES cell cultures.

The phenotype of the neural progenitors following spontaneous differentiation in vitro has been characterized. Upon withdrawal of mitogens from the medium and plating on laminin, the spheres attached rapidly, and cells migrated out to form a monolayer of differentiated cells. The expression of transcripts of the regulatory genes of midbrain development and markers of DA neurons was up regulated in the differentiated progeny (FIG. 32). After 7 days of differentiation, immunocytochemical studies were performed. Standard protocols were used for the immunophenotyping of disaggregated progenitor cells and differentiated cells following fixation with 4% paraformaldehyde. Primary antibodies localization was performed by using swine anti-rabbit and goat anti-mouse immunoglobulins conjugated to fluorescein isothiocyanate (FITC) (Dako, A/S Denmark; 1:20-50), goat anti mouse IgM conjugated to FITC (Jackson Lab. West Grove, Pa.: 1:100), goat anti rabbit Ig conjugated to Texas Red (Jackson Lab, 1:100) and goat anti mouse IgG conjugated to $Cy^{TH}3$ (Jackson Lab., 1:500). Proper controls for primary and secondary antibodies revealed neither non-specific staining nor antibody cross reactivity.

To characterize the immunophenotype of cells within the aggregates, spheres that were cultivated for 6 weeks were mechanically partially disaggregated, and the resulting small clumps and single cells were plated in serum-free medium, as described above, on poly-D-lysine (30-70 kDa, 10 µg/ml, Sigma, St. Louis, Mo.) and laminin (4 µg/ml, Sigma). The cells were fixed after 24 hours and examined for the expression of N-CAM (Dako; mouse IgG 1:10), nestin (rabbit antiserum a kind gift of Dr. Ron McKay; 1:25; or from Chemicon, Temecula, Calif.; rabbit anti human 1:100-200), A2B5 (ATCC, Manassas, Va.; mouse clone 105 1:20), PSA-N-CAM (Developmental Studies Hybridoma Bank, Iowa city, Iowa; mouse undiluted, or from Chemicon Temecula, Calif. mouse 1:200). One-to-two hundred cells were scored within random fields (at X 400) for the expression of each of these markers and the experiments were repeated at least 3 times.

To induce differentiation, spheres that were 6 weeks in culture, were disaggregated into small clumps and plated on poly-D-lysine and laminin in serum-free growth medium (as described above) without supplementation of growth factors for 1 week. Differentiated cells were analyzed for the expression of GFAP (Dako; rabbit Ig 1:400), β-tubulin III (Sigma; mouse IgG 1:2000), serotonin (Sigma; rabbit 1:1000) and tyrosine hydroxylase (TH) (Pel-Freez anti Rabbit polyclonal, 1:100). To determine the percentage of neurons, 200-500 cells were scored within random fields of the outgrowth from differentiating clumps (at X400) and the experiments were repeated at least 3 times.

From the immunocytochemical studies, it was found that 30% of the cells were immunoreactive with anti β-tubulin III (a neuronal marker) (FIGS. 31J, H and I). Double labelling studies showed that about 0.5% of the cells in these cultures co-expressed β-tubulin III and tyrosine hydroxylase (TH) (FIG. 31H), and 0.8-1% co-expressed β-tubulin III and serotonin (FIG. 31I). These results suggested that under our culture conditions a low percentage (<11%) of the progenitors spontaneously differentiated in vitro into putative mid/hind brain neurons.

B Survival and Differentiation of Human NPs after Transplantation to Parkinsonian Rats The survival, differentiation and function of the hES cell-derived NPs in vivo after transplantation to the rat animal model of Parkinson's disease was analyzed.

A Parkinson's disease model was induced in adult Sprague-Dawley rats by stereotaxic injection of the neurotoxin 6-hydroxydopamine to cause unilateral nigrostriatal lesions. 8 µg/rat of 6-hydroxydopamine were Injected in 4 µl into the right Substantia Nigra. 6-hydroxydopamine was injected to the right substantia-nigra to deplete dopaminergic innervation in the ipsilateral stratum. Coordinates of injection were P=4.8, L=1.7, H=−8.6. Preliminary experiments confirmed this resulted in the complete loss of TH+ stained neurons in the ipsilateral striatum, whereas TH expression in the contralateral side was preserved.

At 18 days after the lesion, Parkinsonian rats with >350 rotations per hour after S.C. injection of apomorphine (25 mg/100 gr body weight) were selected for the transplantation experiment.

At 3 weeks after the lesion, hES-cell derived neural spheres that had been passaged for 6 weeks were grafted (along two tracts, $4 \times 10^5$ cells/animal) into the right striatum of rats that were preselected for apomorphine-induced high rotational activity. Two days after selection of Parkinsonian rats, animals were stereotaxically injected with either neurospheres or medium into 2 sites of the right striatum. The hES-derived neural spheres (passaged for 6 weeks) were mechanically dissociated into small clumps and transplanted (about 400,000 cells in 12-14 µl/animal) with a hamilton syringe, along 2 tracts per striatum, using a stereotaxic device. Coordinates for transplantation were: anteromedial tract—A-P=0, L=3.5, H=−7.5 to −4.5 and posterolateral tract—A=1, L=2, H=−7.5 to −4. Control rats underwent sham operation and were injected with vehicle solution. To prevent rejection of grafted human cells, all rats (transplanted and controls) received daily I.P injection of 10 mg/kg cyclosporine A (Sandimmune, Sandoz).

The rats were sacrificed for histopathological analysis of the graft 24 hours after transplantation (n=6), and after behavioral follow up of 12 weeks (21 sphere and 17 vehicle grafted rats).

At the end of follow-up and behavioral studies, rats were euthanized by pentobarbital overdose and perfused with saline and 4% paraformaldehyde. Serial 8 μm coronal frozen sections were prepared and every seventh section was stained with hematoxylin and eosin (H&E) to identify the graft in the brain. In areas in which a graft was identified, the sections were post fixated with 4% formaldehyde. Immunofluorescent stainings were performed with the following primary antibodies; human-specific mitochondrial antibody (mouse IgG, Chemicon; 1:20), tyrosine hydroxylase (TH rabbit IgG, Chemicon 1:100), nestin (antibody as detailed above; 1:50), neurofilament heavy chain (NF-200 mouse IgG, Sigma; 1:100), β III-tubulin (antibody as detailed above; 1:50), neuronal nuclei marker (NeuN mouse IgG Chemicon 1:50).

Sections that were post fixated with acetone were stained with human-specific ribonuclear protein antibody (RNP, mouse IgM, Chemicon; 1:20). Sections that were post fixated with methanol were stained with Proliferating Cell Nuclear Antigen (PCNA mouse IgG Chemicon 1:100), Ki67 Antigen (Rabbit polyclonal, Novocastra laboratories 1:100), vesicular monoamine transporter 2 (VMAT2, rabbit Pel-Freez 1:50-100), human dopamine transporter (rat monoclonal, Chemicon 1:2000). Goat anti mouse IgG conjugated to Alexa 488 or Cy3, goat anti mouse IgM conjugated to texas red, goat anti rabbit IgG conjugated to Alexa 488 or to texas red (Jackson; 1:100) and goat anti rat IgG conjugated to Alexa 488 (Molecular Probes 1:500) were used where appropriate for detection of primary antibodies. Double stains were performed by using primary antibodies of different species or Ig subtype, followed by non-cross-reactive secondary antibodies. Double labeling for TH and human mitochondria was used to evaluate the percentage of TH+ neurons within the grafts. At least 3 high power microscopic fields per section and 3 sections per animal were counted for TH+ cells within the graft. Images were taken by a fluorescent microscope (Nikon E600) or confocal microscope (Zeiss), using channels for Alexa 488 fluorescence, Cy3 and Cy5 fluorescence and Nomarsky optics.

The grafts were easily identified on H&E stained sections and by fluorescent DAPI nuclear counterstaining. At 12 weeks after transplantation, a graft was found in 17 animals. In each of these animals, two grafts were found, most often as a tubular mass of cells along the needle tract within the striatum. In five animals one of the two grafts was ectopic and was observed as a round mass in the cortex.

Anti human-specific mitochondria antibodies to specifically identify human cells in transplanted rat brain sections (FIG. 33A) were used. Identification of human cells was confirmed by staining for human-specific ribo-nuclear protein (FIG. 33B). At 24 hours post-transplantation, there was widespread expression of nestin in the graft (FIG. 33C). At 12 weeks post-transplantation, the positive human mitochondria cells were found only at the site of transplantation, and there was no indication for cell migration to neighboring regions.

To evaluate graft survival, estimations of the number of transplanted cells at 24 hours and 3 months post-transplantation were compared. Since actual counting of the grafted cells was not practical an approach that allowed rough estimation and comparison of the number of cells within the grafts was used. A coronal section along and through the center of the tubular transplants was identified and chosen from serial H&E stained coronal sections. Assuming that the graft had a symmetrical tubular structure, the area of the graft in the section was proportional to the volume of the graft. Since there was edema and some free blood within and around the transplants at 24 hours, and the density of human cells differed between grafts, the area of the grafts in the selected coronal sections was not representative of the number of cells. To overcome this problem an adjacent section was stained for human mitochondria and the amount of human cells by quantifying the human-specific mitochondrial staining was measured. This was calculated by multiplying the entire stained area (in low-power microscopic fields) with fluorescence intensity above background. Twenty-four hours after transplantation, the overall graft mitochondrial staining in sections through the center of the transplants was 94+/−34 (arbitrary units; n=6) and at 12 weeks it was 43+/−18 units (n=5). This indicated approximately 45% graft survival at 12 weeks after transplantation.

Double staining with human specific markers and neuronal markers, indicated the generation of human mitochondria+, neurofilament+ (FIG. 33D) and human ribonuclear protein+, Neun+ (FIG. 33E) neurons from transplanted cells. Double staining for human mitochondria and tyrosine-hydroxylase (TH) showed the presence of graft-derived TH+ cells and fibers (FIG. 33F-H). The vehicle-grafted animals showed no TH staining in the ipsilateral substantia nigra or the striatum. At 12 weeks post-transplantation, the number of TH+ cells in the human mitochondria stained areas, relative to the number of DAPI+ counterstained nuclei, indicated that 0.41+/−0.3% of the human cells generated TH+ neurons (n=9 animals). Since $4 \times 10^5$ cells were transplanted into each rat, it may be estimated, therefore, that the graft generated approximately 740 TH+ neurons.

Cells that were decorated with an antibody directed against human dopamine transporter were identified within the graft and were undetectable in the striatum of medium-grafted controls (FIG. 33I). In addition, an antibody directed against human vesicular monoamine transporter (V-MAT2), a dopaminergic neuronal marker (Miller et al., 1999), decorated graft-derived cells that co-labeled with the human anti mitochondrial antibody (FIG. 33J,K). V-MAT2+ cells were not observed in the striatum of sham operated animals.

To confirm the expression of human dopaminergic neuronal markers in the transplanted brains, RT-PCR analysis of striatal samples from vehicle and neural progenitor grafted rats was performed (as in Example 3). Transcripts of human midbrain and dopaminergic neuron markers were expressed in samples from animals that received stem cell transplantation (n=3) and were not detected in vehicle-transplanted animals (n=2). The expression of these human-specific mRNA transcripts was found only in the transplanted side, and not in the non-lesioned side of the same animals (FIG. 34).

Given the potential of ES cells to generate teratomas after transplantation, we evaluated the percentage of proliferating cells within the grafts. At 24 hours post-transplantation, the majority of cells (64.5%) were in a proliferative state as indicated by positive PCNA (FIG. 33L) and ki67 staining (not shown). At 12 weeks, there were very rare (<0.2%) PCNA+ cells (FIG. 33M). In addition, H&E stained sections covering the entire brain, did not reveal teratomas or any other tumor formation in transplanted rats.

C. Functional Recovery in Parkinsonian Rats after Transplantation of hES-derived Neural Spheres.

At 2 weeks, 1 month, 2 months, and 3 months after transplantation, the severity of the disease was scored by pharmacological tests and compared between hES cell transplanted and vehicle transplanted animals. Rotations were counted for 1 hour after S.C. injection of apomorphine (25 μg/100 g body weight) and for 1 hour after I.P. d-amphetamine (4 mg/kg, performed 2 days later) by a computerized rotometer system (San-Diego Instruments, Inc).

Pharmacological-induced rotational behavior was measured in rats that were transplanted with spheres or with medium at 2 weeks (Baseline), 4 weeks, 8 weeks and 12 weeks after engraftment (FIG. 35). The 2 rats in which no graft was found did not exhibit any improvement in motor function. In transplanted rats (n=10 rats in which a graft was found), amphetamine-induced rotations decreased from 607±200/hour at baseline to 334±130/hour at 12 weeks (45% decrease, p=0.001, FIG. 35A). It should be noted that the difference was already statistically significant at 8 weeks. Amphetamine-induced rotations increased in the control group (n=10 rats) from 480±210/hour to 571±235/hour at 12 weeks. Apomorphine-induced rotations decreased in the transplanted group (n=19 rats) from an average of 624±220/hour at baseline to 423±158 rotations/hour at 12 weeks (31% decrease, p=0.0015, FIG. 35B). The difference between the groups was significant already at 8 weeks. The control group (n=17) rotated 567±169 times per hour at baseline and 571±112 after 12 weeks.

Non-pharmacological tests were performed at 2 weeks and 3 months after transplantation. These included stepping adjustments (Olsson et al., 1995) and forelimb placing (Lindner et al., 1997) tests. The number of stepping adjustments was counted for each forelimb during slow-sideway movements in forehand and backhand directions over a standard flat surface. The stepping adjustments test was repeated three times for each forelimb during three consecutive days. The forelimb-placing test assesses the rats' ability to make directed forelimb movements in response to a sensory stimulus. Rats were held with their limbs hanging unsupported. They were then raised to the side of a table so that their whiskers made contact with the top surface while the length of their body paralleled the edge of the tabletop. Normally, rats place their forelimb on the tabletop almost every time. Each test included ten trials of placing of each forelimb and was repeated in three consecutive days. The results of both tests are expressed as percentage of forelimb stepping adjustments and placing in the lesioned side as compared to the non-lesioned side. The mean number of rotations and the mean results (in percentage) of non-pharmacological tests were compared between the experimental groups using the student t-test.

The behavioral analysis was extended to include also the stepping adjustments (Olsson et al., 1995) and forelimb placing (Lindner et al 1997) non-pharmacological tests. Non-pharmacological tests provide a more direct measure of motor deficits analogous to those found in human Parkinson's disease (Kim et al., 2002). Stepping and placing were examined at baseline (2 weeks) and at 12 weeks after transplantation. At 2 weeks the transplanted rats did not make any stepping or placing in the lesioned side. At 12 weeks there was a significant improvement in both non-pharmacological tests as compared to baseline and to control rats (FIG. 35 C, D).

Values in the behavioral tests are given as mean±standard error. Statistical analysis for the pharmacological tests was performed by one-tailed analysis of variance (ANOVA), followed by Bonferroni post hoc test. In the non-pharmacological tests the groups were compared by the student's t-test. A statistical significant difference was considered when p<0.05.

This study shows that transplantation of hES cell-derived neural spheres improves the motor function in rats in an experimental model of Parkinson's disease.

A simple two-step protocol to direct the differentiation of hES cells in-vitro into highly enriched cultures of proliferating NPs has been used. The NPs expressed transcripts of key regulatory genes of midbrain development as well as markers of dopaminergic neurons supporting their potential to differentiate into midbrain dopaminergic neurons. Following transplantation, a significant clinical effect was evident by all four different behavioral tests. Functional recovery in the pharmacological behavioral tests was evident and significant at 8 and 12 weeks after transplantation. The functional recovery in the lesioned rats was correlated by the demonstration of transplant-derived dopaminergic cells, as indicated by immunofluorescent stainings and RT-PCR. At the RNA level, human specific transcripts of key regulatory genes of midbrain development as well as markers of DA neurons were observed in brain samples from the location of the graft. At be protein level, human cells decorated with antibodies against dopamine neuron specific markers including DAT (Kim et al 2002) and VMAT2 (Miller et al., 1999) were observed within the grafts. Collectively this data suggest that the behavioral recovery that we have observed Was related to the differentiation of the grafted NPs into functional DA neurons. However, further studies are required to confirm that hES cells can differentiate into DA neurons with phenotype, function and interaction with host neurons that are identical to those of authentic midbrain DA neurons.

These findings suggest that commitment of the human cells to a dopaminergic fate prior to their transplantation is a prerequisite to obtain a larger number of graft-derived dopaminergic neurons.

Transplantation of low dose of undifferentiated mouse ES cells into parkinsonian rats resulted in the formation of teratomas in a high percentage of animals (Bjorklund et. al., 2002). Here, the human ES cells were directed to differentiate in-vitro into neural progenitors prior to transplantation and ceased to express the transcription factor Oct-4, a marker of undifferentiated ES cells. The human grafts did not produce teratomas or non-neural tissue in the rat brains. In correlation, the transplanted cells ceased to express markers of proliferating cells. Nevertheless, additional extensive long-term studies are required to determine the safety of human ES derived neural progeny transplantation and to rule out potential hazards such as tumor formation or the development of cells from other lineages.

This study shows for the first time that human ES cell-derived NPs can induce functional recovery in an experimental model of Parkinson's disease. The therapeutic effect, demonstrated in this study, indicate the potential of hES cells for transplantation therapy and encourage further efforts that may eventually allow the use of hES cells for the treatment of neurological disorders.

REFERENCES

Acampora D and Simeone A. Understanding the roles of Otx1 and Otx2 in the control of brain morphogenesis. Trends Neuroscience 1999; 22: 116-122.

Ben-Hur T, Einstein O, Mizrachi-Kol R, Ben-Menachem O, Reinhartz E, Karussis D, Abramsky O. Transplanted multipotential neural precursor cells migrate into the inflamed white matter in response to experimental autoimmune encephalomyelitis. Glia 2003; 41: 73-80.

Bjorklund A and Lindvall O. Cell replacement therapies for central nervous system disorders. Nature Neuroscience 2000; 3: 537-544.

Bjorklund L M, Sanchez-Pernaute R, Chung S, Andersson T, Chen I Y McNaught K S, Brownell A L, Jenkins B G, Wahlestedt C, Kim K S, Isacson O. Embryonic stem cells develop into functional dopaminergic neurons after transplantation in a Parkinson rat model. Proc Nati Acacd Sci USA. 2002 Feb. 19; 99(4):2344-9.

Freed C R et al. Transplantation of embryonic dopamine neurons for severe Parkinson's disease. N Engl J Med 2001; 344: 710-9.

Gropp M, Itsykson P, Singer O, Ben-Hur T, Reinhartz E, Galun E, Reubinoff B E. Stable genetic modification of human embryonic stem cells by lentiviral vectors. Molecular Therapy 2003; 7: 281-287.

Heikinheimo M, Lawshe A, Shackleford G M, Wilson D B, NacArthur C A. FGF-8 expression in the post gastrulation mouse suggests roles in the development of the face, limbs, and central nervous system. Mach Dev 1994; 48: 129-38.

Hoshikawa M, Ohbayashi N, Yonamine A, Konishi M, Ozaki K, Fukui S, Itoh N. Structure and expression of a novel fibroblast growth factor, FGF-17, preferentially expressed in the embryonic brain. Biochem Biophys Res Commun 1998 Mar. 6; 244.

Isacson O and Deacon T. Neural transplantation studies reveal the brains capacity for continuous reconstruction. Trends Neurosci 1997; 477-82.

Kawasaki H et al. Induction of midbrain dopaminergic neurons from ES cells by stromal cell derived inducing activity. Neuron 2000; 28: 31-40.

Kim J H et al. Dopamine neurons derived from embryonic stem cells function in an animal model of Parkinson's disease. Nature 2002; 418: 50-6.

Lee S H et al. Efficient generation of midbrain and hindbrain neurons from mouse embryonic stem cells. Nature Biotechnology 2000; 18: 675-679.

Lindvall O. Neural transplantation: a hope for patients with Parkinson's disease. Neuroreport 1997; 8(14): iii-x.

Lindner M D et al. Rats with partial striatal dopamine depletions exhibit robust and long-lasting behavioral deficits in a simple fixed-ratio bar-pressing task. Behav Brain Res 1997; 86: 25-40.

Miller G W, Erickson J D, Perez J T, Penland S N, Mash D C, Rye D B, Levey A I. Immunochemical analysis of vesicular monoamine transporter (VMAT2) protein in Parkinson's disease. Exp Neurol. 1999; 156:138-48.

Olsson M et al. Forelimb akinesia in the rat Parkinson model: differential effects of dopamine agonists and nigral transplants as assessed by a new stepping test. J Neurosci 1995; 15: 3863-75.

Pera M F et al. Human embryonic stem cells. J Cell Sci. 2000; 113: 5-10.

Pluchino S, Quattrini A, Brambilla E, Gritti A, Salani C, Dina G, Galli R, Del Carro U, Amadio S, Bergami A, Furlan R, Comi G, Vesovi A L, Martino G. injection of adult neurospheres induces recovery in a chronic model of multiple sclerosis. Nature 2003; 422: 688-94

Reubinoff B E, Pera M F, Fong C Y, Trounson A, Bongso A. Embryonic stem cell lines from human blastocysts: somatic differentiation in vitro. Nat Biotechnol 2000; 18(4):399-404.

Reubinoff B E, Itsykson P, Turetsky T, Pera M F, Reinhart E, Itzik A, Ben-Hur T. Neural progenitors from human embryonic stem cells. Nat Biotechnol 2001 December; 19(12):1134-40

Rowitch D H & McMahon A P. Pax-2 expression in the murine neural plate precedes and encompasses the expression domains of Wnt-1 and En-1. Mech Dev 1995; 52: 3-8.

Sanchez-Pernaute R, Studer L, Bankiewicz K S, Major E O, and McKay R D. In vitro generation and transplantation of precursors-derived human dopamine neurons. J Neurosci. Res. 2001; 65: 284-288.

Simeone A. Otx1 and Otx2 in the development and evolution of the mammalian brain. EMBO 1998; 17: 6790-6798.

Smidt M P et al. A second independent pathway for development of mesencephalic dopaminergic neurons requires Lmx1b. Nat Neurosci 2000; 3: 337-41.

Stoykova A & Gruss P. Roles of Pax genes in developing and adult brain as suggested by expression patterns. J Neuroscience 1994; 14:1395-1412.

Studer L, Tabar V, McKay R D. Transplantation of expanded mesencephalic precursors leads to recovery in parkinsonian rats. Nature Neuroscience 1998; 1: 290-295.

Stull N D & Lacovitti L. Sonic hedgehog and FGF8: inadequate signals for the differentiation of a dopamine phenotype in mouse and human neurons in culture. Exp Neurol. 2001; 169: 36-43.

Xu J, Lawshe A, MacArthur G A, Ornitz D M. Genomic structure, mapping, activity and expression of FGF-17. Mech Dev 1999; 83: 165-78.

Xu J, Liu Z, Ornitz D M. Temporal and spatial gradients of FGF-8 and FGF-17 regulate proliferation and differentiation of midline cerebellar structures. Development 2000; 127: 1833-43.

Zetterstrom R H et al. Dopamine neuron agenesis in Nurr1-deficient mice. Science 1997; 276: 248-50

Finally it is to be understood that various other modifications and/or alterations may be made without departing from the spirit of the present invention as outlined herein.

The invention claimed is:

1. A method of generating neural progenitor cells in vitro, comprising
   (a) culturing undifferentiated human embryonic stem (ES) cells in a serum free medium comprising FGF-2 and noggin to generate neural progenitor cells; and
   (b) further differentiating said neural progenitor cells in a serum free medium comprising FGF2 for three weeks, said serum free medium being devoid of noggin, thereby generating neural progenitor cells.

2. The method of claim 1, wherein said FGF-2 is approximately 20 ng/ml.

3. The method of claim 1, wherein a concentration of said noggin is in the range of 350 to 700 ng/ml.

4. The method of claim 1, wherein said culturing is in suspension.

5. The method of claim 1, wherein said serum free medium comprising FGF and noggin is devoid of leukemia inhibitory factor (LIF).

6. A method of generating neural progenitor cells in vitro, the method culturing undifferentiated human embryonic stem (ES) cells in a serum free medium comprising FGF-2 and noggin, said medium being devoid of LIF, thereby generating neural progenitor cells.

7. The method of claim 6, wherein said FGF-2 is approximately 20 ng/ml.

8. The method of claim 6, wherein a concentration of said noggin is in the range of 350 to 700 ng/ml.

9. The method of claim 6, wherein said culturing is in suspension.

* * * * *

SEQUENCE LISTING

<160> NUMBER OF SEQ ID NOS: 28

<210> SEQ ID NO 1
<211> LENGTH: 18
<212> TYPE: DNA
<213> ORGANISM: Artificial sequence
<220> FEATURE:
<223> OTHER INFORMATION: Single strans DNA oligonucleotide

<400> SEQUENCE: 1
atgattggca gcgtggag                                                 18

<210> SEQ ID NO 2
<211> LENGTH: 20
<212> TYPE: DNA
<213> ORGANISM: Artificial sequence
<220> FEATURE:
<223> OTHER INFORMATION: Single strans DNA oligonucleotide -continued

```
<400> SEQUENCE: 2
gtccagctgt gaagtgcttg                                           20

<210> SEQ ID NO 3
<211> LENGTH: 22
<212> TYPE: DNA
<213> ORGANISM: Artificial sequence
<220> FEATURE:
<223> OTHER INFORMATION: Single strans DNA oligonucleotide

<400> SEQUENCE: 3
cgttctcttt ggaaaggtgt tc                                        22

<210> SEQ ID NO 4
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 4
acactcggac cacgtctttc                                           20

<210> SEQ ID NO 5
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 5
cgccttacgc agtcaatggg                                           20

<210> SEQ ID NO 6
<211> LENGTH: 21
<212> TYPE: DNA
<213> ORGANISM: Artificial sequence
<220> FEATURE:
<223> OTHER INFORMATION: Single strans DNA oligonucleotide

<400> SEQUENCE: 6
cgggaagctg gtgatgcata g                                         21

<210> SEQ ID NO 7
<211> LENGTH: 21
<212> TYPE: DNA
<213> ORGANISM: Artificial sequence
<220> FEATURE:
<223> OTHER INFORMATION: Single strans DNA oligonucleotide

<400> SEQUENCE: 7
tttgtgaacg gccggcccct a                                         21

<210> SEQ ID NO 8
<211> LENGTH: 21
<212> TYPE: DNA
<213> ORGANISM: Artificial sequence
<220> FEATURE:
<223> OTHER INFORMATION: Single strans DNA oligonucleotide

<400> SEQUENCE: 8
cattgtcaca gatgccctcg g                                         21

<210> SEQ ID NO 9
<211> LENGTH: 23
<212> TYPE: DNA
```

```
<213> ORGANISM: Artificial sequence
<220> FEATURE:
<223> OTHER INFORMATION: Single strans DNA oligonucleotide

<400> SEQUENCE: 9
ccgagcagac cacagagtat tca                                              23

<210> SEQ ID NO 10
<211> LENGTH: 22
<212> TYPE: DNA
<213> ORGANISM: Artificial sequence
<220> FEATURE:
<223> OTHER INFORMATION: Single strans DNA oligonucleotide

<400> SEQUENCE: 10
cagtgacggt cataggcagt gg                                               22

<210> SEQ ID NO 11
<211> LENGTH: 22
<212> TYPE: DNA
<213> ORGANISM: Artificial sequence
<220> FEATURE:
<223> OTHER INFORMATION: Single strans DNA oligonucleotide

<400> SEQUENCE: 11
tcctgatgcg agtcaacgag tc                                               22

<210> SEQ ID NO 12
<211> LENGTH: 22
<212> TYPE: DNA
<213> ORGANISM: Artificial sequence
<220> FEATURE:
<223> OTHER INFORMATION: Single strans DNA oligonucleotide

<400> SEQUENCE: 12
ctgccagtgt ctctcggacc tt                                               22

<210> SEQ ID NO 13
<211> LENGTH: 22
<212> TYPE: DNA
<213> ORGANISM: Artificial sequence
<220> FEATURE:
<223> OTHER INFORMATION: Single strans DNA oligonucleotide

<400> SEQUENCE: 13
gcacttcggc agagttgaat ga                                               22

<210> SEQ ID NO 14
<211> LENGTH: 22
<212> TYPE: DNA
<213> ORGANISM: Artificial sequence
<220> FEATURE:
<223> OTHER INFORMATION: Single strans DNA oligonucleotide

<400> SEQUENCE: 14
ggtggctgtg ttgctggtag tt                                               22

<210> SEQ ID NO 15
<211> LENGTH: 22
<212> TYPE: DNA
<213> ORGANISM: Artificial sequence
<220> FEATURE:
<223> OTHER INFORMATION: Single strans DNA oligonucleotide

<400> SEQUENCE: 15
ctgggtgtac tgcacacgtt at                                               22
```

-continued

```
<210> SEQ ID NO 16
<211> LENGTH: 22
<212> TYPE: DNA
<213> ORGANISM: Artificial sequence
<220> FEATURE:
<223> OTHER INFORMATION: Single strans DNA oligonucleotide

<400> SEQUENCE: 16
tactcgctct cgtctttgtc ct                                              22

<210> SEQ ID NO 17
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 17
gtgggtctac tgtacgcgct                                                 20

<210> SEQ ID NO 18
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 18
cctactcgct gtccgacttg                                                 20

<210> SEQ ID NO 19
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 19
ctcggaccaa agtgatccat                                                 20

<210> SEQ ID NO 20
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 20
gggtggcaac cataaagaaa                                                 20

<210> SEQ ID NO 21
<211> LENGTH: 23
<212> TYPE: DNA
<213> ORGANISM: Artificial sequence
<220> FEATURE:
<223> OTHER INFORMATION: Single strans DNA oligonucleotide

<400> SEQUENCE: 21
gtcccctggt tcccaagaaa agt                                             23

<210> SEQ ID NO 22
<211> LENGTH: 23
<212> TYPE: DNA
<213> ORGANISM: Artificial sequence
<220> FEATURE:
<223> OTHER INFORMATION: Single strans DNA oligonucleotide
```

-continued

```
<400> SEQUENCE: 22
tccagctggg ggatattgtc ttc                                             23

<210> SEQ ID NO 23
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 23
cgcaccactg gcattgtcat                                                 20

<210> SEQ ID NO 24
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 24
ttctccttga tgtcacgcac                                                 20

<210> SEQ ID NO 25
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 25
agccacatcg ctcagacacc                                                 20

<210> SEQ ID NO 26
<211> LENGTH: 19
<212> TYPE: DNA
<213> ORGANISM: Artificial sequence
<220> FEATURE:
<223> OTHER INFORMATION: Single strans DNA oligonucleotide

<400> SEQUENCE: 26
gtactcagcg ccagcatcg                                                  19

<210> SEQ ID NO 27
<211> LENGTH: 20
<212> TYPE: DNA
<213> ORGANISM: Artificial sequence
<220> FEATURE:
<223> OTHER INFORMATION: Single strans DNA oligonucleotide

<400> SEQUENCE: 27
tgggagtctg cctgttgcag                                                 20

<210> SEQ ID NO 28
<211> LENGTH: 19
<212> TYPE: DNA
<213> ORGANISM: Artificial sequence
<220> FEATURE:
<223> OTHER INFORMATION: Single strans DNA oligonucleotide

<400> SEQUENCE: 28
cagcgaaccg tcctctggg                                                  19
```